US006506733B1

(12) United States Patent
Buysse et al.

(10) Patent No.: US 6,506,733 B1
(45) Date of Patent: Jan. 14, 2003

(54) COMPOUNDS AND COMPOSITIONS AS PROTEASE INHIBITORS

(75) Inventors: Ann M. Buysse, Carmel, IN (US); Rohan V. Mendonca, Millbrae, CA (US); James T. Palmer, Corte Madera, CA (US); Zong-Qiang Tian, Fremont, CA (US); Shankar Venkatraman, Foster City, CA (US)

(73) Assignee: Axys Pharmaceuticals, Inc., So. San Francisco, CA (US)

( * ) Notice: Subject to any disclaimer, the term of this patent is extended or adjusted under 35 U.S.C. 154(b) by 0 days.

(21) Appl. No.: 09/526,300

(22) Filed: Mar. 15, 2000

Related U.S. Application Data
(60) Provisional application No. 60/124,529, filed on Mar. 15, 1999.

(51) Int. Cl.[7] .................... A61K 38/05; A61K 38/06; C07C 271/00; C07K 5/06; C07K 5/08
(52) U.S. Cl. ................... 514/18; 514/19; 514/102; 514/107; 514/108; 514/255.01; 514/315; 514/331; 514/601; 514/602; 514/605; 514/613; 514/617; 514/625; 564/83; 564/84; 564/95; 564/152; 564/155; 564/159; 564/161; 564/182; 564/183; 564/192; 530/331; 544/388; 546/215
(58) Field of Search ................... 514/18, 19, 20, 514/102, 107, 108, 255, 315, 331, 601, 602, 605, 613, 617, 625, 255.01; 530/331, 345; 544/388; 546/245; 564/83, 84, 95, 152, 155, 159, 161, 182, 183, 192

(56) References Cited

U.S. PATENT DOCUMENTS

| 5,424,325 A | * 6/1995 | Ando et al. .................. 514/357 |
| 5,486,623 A | * 1/1996 | Zimmerman et al. ....... 549/417 |
| 5,498,616 A | * 3/1996 | Mallano et al. ............. 514/300 |
| 5,998,390 A | * 12/1999 | Ramamurthy et al. ........ 514/94 |

FOREIGN PATENT DOCUMENTS

| EP | 0 272 671 A2 | 6/1988 |
| JP | 06 192199 | 7/1994 |
| WO | WO 96/21655 | 7/1996 |
| WO | WO 98/49190 | 11/1996 |
| WO | WO96/40647 | 12/1996 |
| WO | WO 96/40744 | 12/1996 |
| WO | WO96/41638 | 12/1996 |
| WO | WO97/03679 | 2/1997 |

OTHER PUBLICATIONS

Billson et al. The Design and Synthesis of Inhibitors of the Cysteinyl . . . Bioorg. Med. Chem. Lett. vol. 8, pp. 993–998, 1998.*
Bromme et al. Potent Inactivation of Cathepsins S and L . . . . Biol. Chem. Hoppe—Seyler. vol. 375, No. 5, pp. 343–347, 1994.*
Krantz et al. Peptidyl (Acyloxy)methyl Ketones and the Quiescent . . . Biochemistry. vol. 30, pp. 4678–4687, 1991.*
Pliura et al. Comparative behavior of colpain and cathepsin B . . . Biochem. J. vol. 288, pp. 759–762, 1992.*
Smith et al. New Inhibitors of Cysteine Proteinases, J. Am. Chem. Soc. vol. 110, No. 13, pp. 4429–4431, 1988.*
Derwent Abstract of Japanese Patent Application 06–192199 (Jul. 12, 1994).*
Marquis, R. W. et al., "Potent dipeptidylketone inhibitors of the cysteine protease cathepsin", *Chemical Abstracts*, 7:4 581–588 (1999).
Harris et al., "Characteristics of a continuous fluorogenic assay for calpain I. Kinetic evaluation of peptide aldehydes, halomethyl ketones and )achalasia) methyl ketones as inhibitors of the enzyme", *Chemical Abstracts*, 110:7, Bioorg. Med. Chem. Lett, 5(4) 393–398 (1995).
Suave et al., Carboxylmodified amino acids and peptides, I An efficient method for the synthesis of monofuctionalized enamines and monofuntionalized methyl ketone derivatives fom thioamides via episulfides and thioiminium salts, *Tetrahedron Lett*, 29:19 2295–2298 (1988).
Ogilvie W. et al.: "Peptidomimetic inhibitors of the human cytomegalovirus protease" Journal of Medicinal Chemistry vol. 40 No. 25 (1997).

* cited by examiner

*Primary Examiner*—Jeffrey E. Russel
(74) *Attorney, Agent, or Firm*—Townsend and Townsend and Crew LLP

(57) ABSTRACT

Compounds of the formula:

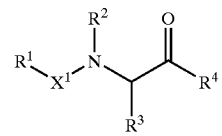

are provided, and are useful as cysteine protease inhibitors, particularly in the treatment of diseases such as osteoporosis or autoimmune disorders in which cathepsins K or S contribute to the pathology or symptomatolgy of the disease.

18 Claims, No Drawings

COMPOUNDS AND COMPOSITIONS AS PROTEASE INHIBITORS

This application claims the benefit under 35 U.S.C. Sec. 119 (e)(1) of prior filed U.S. Provisional Application No. 60/124,529 filed Mar. 15, 1999.

THE INVENTION

This application relates to compounds and compositions for treating diseases associated with cysteine protease activity, particularly diseases associated with activity of cathepsins B, K, L or S.

DESCRIPTION OF THE FIELD

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increase expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. For example, increased cathepsin B levels and redistribution of the enzyme are found in tumors; thus, suggesting a role for the enzyme in tumor invasion and metastasis. In addition, aberrant cathepsin B activity is implicated in such disease states as rheumatoid arthritis, osteo arthritis, pneumocystis caninii, acute pancreatitis, inflammatory airway disease and bone and joint disorders.

The prominent expression of cathepsin K in osteoclasts and osteoclast-related multinucleated cells and its high collagenolytic activity suggest that the enzyme is involved in ososteoclast-mediated bone resorption and, hence, in bone abnormalities such as occurs in osteoporosis. In addition, cathepsin K expression in the lung and its elastinolytic activity suggest that the enzyme plays a role in pulmonary disorders as well.

Cathepsin L is implicated in normal lysosomal proteolysis as well as several disease states, including, but not limited to, metastasis of melanomas. Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogeneic immune responses, including, but not limited to, rejection of organ transplants or tissue grafts.

In view of the number of diseases wherein it is recognized that an increase in cysteine protease activity contributes to the pathology and/or symptomatology of the disease, molecules which are shown to inhibit the activity of this class of enzymes, in particular molecules which are inhibitors of cathepsins B, K, L and/or S, will be useful as therapeutic agents.

SUMMARY OF THE INVENTION

This Application relates to protease inhibitors of Formula I:

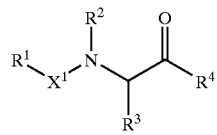

in which:

$X^1$ is a bond or a divalent group of Formula (a) or (b):

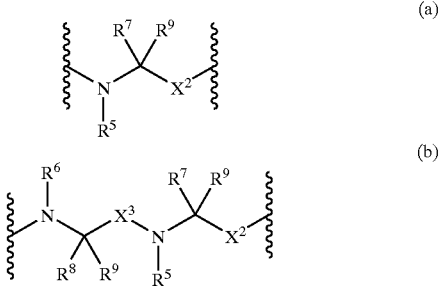

wherein:

$X^2$ and $X^3$ independently are —C(O)— or —CH$_2$S(O)$_2$—;

$R^7$ and $R^8$ are independently (i) (C$_{1-6}$)alkyl optionally substituted with cyano, halo, nitro, —NR$^{10}$R$^{10}$, —NR$^{10}$C(O)OR$^{10}$, —NR$^{10}$C(O)NR$^{10}$R$^{10}$, —NR$^{10}$C(NR$^{10}$)NR$^{10}$R$^{10}$, —OR$^{10}$, —SR$^{10}$, —C(O)OR$^{10}$, —C(O)NR$^{10}$R$^{10}$, —S(O)$_2$NR$^{10}$R$^{10}$, —P(O)(OR$^{10}$)OR$^{10}$, —OP(O)(OR$^{10}$)OR$^{10}$, —NR$^{10}$C(O)R$^{11}$, —S(O)R$^{11}$, —S(O)$_2$R$^{11}$, —C(O)R$^{11}$, —OR$^{12}$, —SR$^{12}$, —S(O)R$^{12}$, —S(O)$_2$R$^{12}$, —C(O)R$^{12}$, —C(O)OR$^{12}$, —OC(O)R$^{12}$, —NR$^{12}$R$^{13}$, NR$^{13}$C(O)R$^{12}$, —NR$^{13}$C(O)OR$^2$, —C(O)N$^{12}$R$^{13}$, —S(O)$_2$NR$^{12}$R$^{13}$, —NR$^{13}$C(O)NR$^{12}$R$^{13}$ or —NR$^{13}$C(NR$^{13}$)NR$^{12}$R$^{13}$, wherein R$^{10}$ at each occurrence independently is hydrogen, (C$_{1-6}$)alkyl or halo-substituted (C$_{1-3}$)alkyl, R$^{11}$ is (C$_{1-6}$)alkyl or halo-substituted (C$_{1-3}$)alkyl, R$^{12}$ is (C$_{3-12}$)cycloalkyl(C$_{0-3}$)alkyl, hetero(C$_{3-12}$)cycloalkyl(C$_{0-3}$)alkyl, (C$_{6-12}$)aryl(C$_{0-3}$)alkyl or hetero(C$_{5-12}$)aryl(C$_{0-3}$)alkyl and R$^{13}$ is hydrogen or (C$_{1-6}$)alkyl, and wherein within R$^{12}$ said cycloalkyl, heterocycloalkyl, aryl, heteroaryl, polycycloaryl or heterpolycycloaryl ring optionally is substituted by a group selected from —R$^{14}$, —X$^4$OR$^{14}$, —X$^4$SR$^{14}$, —X$^4$S(O)R$^{14}$, —X$^4$S(O)$_2$R$^{14}$, —X$^4$C(O)R$^{14}$, —X$^4$C(O)OR$^{14}$, —X$^4$OC(O)R$^{14}$, —X$^4$NR$^{14}$R$^{15}$, —X$^4$NR$^{15}$C(O)R$^{14}$, —X$^4$NR$^{15}$C(O)OR$^{14}$, —X$^4$C(O)NR$^{14}$R$^{15}$, —X$^4$S(O)$_2$NR$^{14}$R$^{15}$, X$^4$NR$^{15}$C(O)NR$^{14}$R$^{15}$ or —X$^4$NR$^{15}$C(NR$^{15}$)NR$^{14}$R$^{15}$, wherein X$^4$ is a bond or (C$_{1-6}$)alkylene, R$^{14}$ is hydrogen or (C$_{1-6}$)alkyl and R$^{15}$ is (C$_{3-12}$)cycloalkyl(C$_{0-6}$)alkyl, hetero(C$_{3-12}$)cycloalkyl(C$_{0-6}$)alkyl, (C$_{6-12}$)aryl(C$_{0-6}$)alkyl, hetero(C$_{5-12}$)aryl(C$_{0-6}$)alkyl, (C$_{9-12}$)polycycloaryl(C$_{0-6}$)alkyl or hetero(C$_{8-12}$)polycycloaryl(C$_{0-6}$)alkyl, or (ii) (C$_{3-12}$)cycloalkyl(C$_{0-3}$)alkyl, heterocyclo(C$_{3-12}$)alkyl(C$_{0-3}$)alkyl, (C$_{6-12}$)aryl(C$_{0-3}$)alkyl, hetero(C$_{5-12}$)aryl(C$_{0-3}$)alkyl, (C$_{9-12}$)polycycloaryl(C$_{0-3}$)alkyl or hetero(C$_{8-12}$)polycycloaryl(C$_{0-3}$)alkyl, wherein within R$^{15}$ said cycloalkyl, heterocycloalkyl, aryl, heteroaryl, polycycloaryl or heterpolycycloaryl ring optionally is substituted by a group selected from —$R^{14}$, —$X^4OR^{14}$, —$X^4SR^{14}$, —$X^4S(O)R^{14}$, —$X^4S(O)_2R^{14}$, —$X^4C(O)R^{14}$, —$X^4C(O)OR^{14}$, —$X^4OC(O)R^{14}$, —$X^4NR^{14}R^{15}$, —$X^4NR^{15}C(O)R^{14}$, —$X^4NR^{15}C(O)OR^{14}$, —$X^4C(O)NR^{14}R^{15}$, —$X^4S(O)_2NR^{14}R^{15}$, —$X^4NR^{15}C(O)NR^{14}R^{15}$ or —$X^4NR^{15}C(NR^{15})NR^{14}R^{15}$, wherein $X^4$, $R^{14}$ and $R^{15}$ are as defined above; wherein within $R^7$ and/or $R^8$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^4NR^{10}R^{10}$, —$X^4NR^{10}C(O)OR^{10}$, —$X^4NR^{10}C(O)NR^{10}R^{10}$, —$X^4NR^{10}C(NR^{10})NR^{10}R^{10}$, —$X^4SR^{10}$, —$X^4C(O)OR^{10}$, —$X^4C(O)R^{10}R^{10}$, —$X^4S(O)_2NR^{10}R^{10}$, —$X^4P(O)(OR^4)OR^{10}$, —$X^4OP(O)(OR^4)OR^{10}$, —$X^4NR^{10}C(O)R^{11}$, —$X^4S(O)R^{11}$, —$X^4S(O)_2R^{11}$ and —$X^4C(O)R^{11}$, wherein $X^4$ is a bond or $(C_{1-6})$alkylene and $R^{10}$ and $R^{11}$ are as defined above, or $R^7$ taken together with $R^5$ and/or $R^8$ taken together with $R^6$ forms trimethylene, tetramethylene or phenylene-1,2-dimethylene, optionally substituted with hydroxy or oxo;

$R^9$ at each occurrence is hydrogen or $(C_{1-6})$alkyl; and $R^5$ and $R^6$ are independently hydrogen, $(C_{1-6})$alkyl or as defined above; and $R^1$ is —$X^6X^7R^{16}$, wherein $X^6$ is —$C(O)$—, —$C(O)C(O)$— or —$S(O)_2$—, $X^7$ is a bond, —$O$— or —$NR^{17}$—, wherein $R^{17}$ is hydrogen or $(C_{1-6})$alkyl, and $R^{16}$ is (i) $(C_1{}_6)$alkyl optionally substituted by cyano, halo, nitro, —$NR^{10}R^{10}$, —$NR^{10}C(O)OR^{10}$, —$NR^{10}C(O)NR^{10}R^{10}$, —$NR^{10}C(NR^{10})NR^{10}R^{10}$, —$OR^{10}$, —$SR^{10}$, —$C(O)OR^{10}$, —$C(O)NR^{10}R^{10}$, —$S(O)_2NR^{10}R^{10}$, —$P(O)(OR^{10})OR^{10}$, —$OP(O)(OR^{10})OR^{10}$, —$NR^{10}C(O)R^{11}$, —$S(O)R^{11}$, —$S(O)_2R^{11}$, —$C(O)R^{11}$, —$OR^{18}$, —$SR^{18}$, —$S(O)R^{18}$, —$S(O)_2R^{18}$, —$C(O)R^{18}$, —$C(O)OR^{18}$, —$C(O)NR^{18}R^{19}$, —$NR^{18}R^{19}$, —$NR^{19}C(O)R^{18}$, —$NR^{19}C(O)OR^{18}$, —$NR^{19}C(O)NR^{18}R^{19}$ or —$NR^{19}C(NR^{19})NR^{18}R^{19}$, wherein $R^{10}$ and $R^{11}$ are as defined above, $R^{18}$ is $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$polycycloaryl$(C_{0-6})$alkyl or hetero$(C_{8-12})$polycycloaryl$(C_{0-6})$alkyl and $R^{19}$ at each occurrence independently is hydrogen or $(C_{1-6})$alkyl, and wherein within $R^{18}$ said cycloalkyl, heterocycloalkyl, aryl, heteroaryl, polycycloaryl or heterpolycycloaryl ring optionally is substituted by a group selected from —$R^{14}$, —$X^4OR^{14}$, —$X^4SR^{14}$, —$X^4S(O)R^{14}$, —$X^4S(O)_2R^{14}$, —$X^4C(O)R^{14}$, —$X^4C(O)OR^{14}$, —$X^4OC(O)R^{14}$, —$X^4N^{14}R^{15}$, —$X^4NR^{15}C(O)R^{14}$, —$X^4NR^{15}C(O)OR^{14}$, —$X^4C(O)NR^{14}R^{15}$, —$X^4S(O)_2NR^{14}R^{15}$, $X^4NR^5C(O)NR^{14}R^{15}$ or —$X^4NR^{15}C(NR^{15})NR^{14}R^{15}$, wherein $X^4$, $R^{14}$ and $R^{15}$ are as defined above, or (ii) $(C_{3-14})$cycloalkyl$(C_{0-6})$alkyl, hetero$(C_{3-14})$cycloalkyl$(C_{0-6})$alkyl, $(C_{6-14})$aryl$(C_{0-6})$alkyl, diphenyl$(C_{0-6})$alkyl, hetero$(C_{5-14})$aryl$(C_{0-6})$alkyl, heterodi$(C_{5-6})$aryl$(C_{0-6})$alkyl, $(C_{9-12})$polycycloaryl$(C_{0-6})$alkyl or hetero$(C_{9-14})$polycyclo$(C_{8-14})$aryl$(C_{0-6})$alkyl, wherein said cycloalkyl, heterocycloalkyl, aryl, heteroaryl, polycycloaryl or heterpolycycloaryl ring optionally is substituted by a group selected from —$R^{14}$, —$X^4OR^{14}$, —$X^4SR^{14}$, —$X^4S(O)R^{14}$, —$X^4S(O)_2R^{14}$, —$X^4C(O)R^{14}$, —$X^4C(O)OR^{14}$, —$X^4OC(O)R^{14}$, —$X^4NR^{14}R^{15}$, —$X^4NR^{15}C(O)R^{14}$, —$X^4NR^{15}C(O)OR^{14}$, —$X^4C(O)$ $NR^{14}R^{15}$, —$X^4S(O)_2NR^{14}R^{15}R$, —$X^4NR^{15}C(O)R^{14}R^{15}$ or —$X^4NR^{15}C(NR^{15})NR^{14}R^{15}$, wherein $X^4$, $R^{14}$ and $R^{15}$ are as defined above; wherein within $R^1$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^4NR^{10}R^{10}$, —$X^4NR^{10}C(O)OR^{10}$, —$X^4NR^{10}C(O)NR^{10}R^{10}$, —$X^4NR^{10}C(NR^{10})NR^{10}R^{10}$, —$X^4OR^{10}$, —$X^4SR^{10}$, —$X^4C(O)OR^{10}$, —$X^4C(O)NR^{10}R^{10}$, —$X^4S(O)_2NR^{10}R^{10}$, —$X^4P(O)(OR^4)OR^{10}$, —$X^4OP(O)(OR^4)OR^{10}$, —$X^4NR^{10}C(O)R^{11}$, —$X^4S(O)R^{11}$, —$X^4S(O)_2R^{11}$ and —$X^4C(O)R^{11}$, wherein $X^4$, $R^{10}$ and $R^{11}$ are as defined above; or when $X_1$ is a divalent group of Formula (a) or (b) then $R^1$ may also represent hydrogen;

$R^2$ is hydrogen or $(C_{1-6})$alkyl;

$R^3$ is hydrogen or $(C_{1-6})$alkyl wherein said alkyl optionally is substituted with —$OR^{20}$, —$NR^{21}C(O)OR^{20}$, —$C(O)NR^{20}R^{21}$, —$S(O)_{20}R^{21}$, wherein $R^{20}$ is $(C_{0-6})$alkyl or $(C_{6-10})$aryl$(C_{0-6})$alkyl and $R^{21}$ is hydrogen or $(C_{1-6})$alkyl, or (ii) $(C_{6-10})$aryl$(C_{1-6})$alkyl or $(C_{5-10})$heteroaryl$(C_{1-6})$alkyl or;

$R^3$ taken together with $R^2$ forms trimethylene, tetramethylene or phenylene-1,2-dimethylene, optionally substituted with hydroxy or oxo; wherein within $R^3$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^4NR^{10}R^{10}$, —$X^4NR^{10}C(O)OR^{10}$, —$X^4NR^{10}C(O)NR^{10}R^{10}$, —$X^4NR^{10}C(NR^{10})NR^{10}R^{10}$, —$X^4OR^{10}$, —$X^4SR^{10}$, —$X^4C(O)OR^{10}$, —$X^4C(O)NR^{10}R^{10}$, —$X^4S(O)_2NR^{10}R^{10}$, —$X^4P(O)(OR^4)OR^{10}$, —$X^4OP(O)(OR^4)OR^{10}$, —$X^4NR^{10}C(O)R^{11}$, —$X^4S(O)R^{11}$, —$X^4S(O)_2R^{11}$ and —$X^4C(O)R^{11}$, wherein $X^4$, $R^{10}$ and $R^{11}$ are as defined above; and $R^4$ is nitromethyl, 1-hydroxy-1-methylethyl or —$CH_2OR^{22}$, wherein $R^{22}$ is hydrogen, $(C_{1-6})$alkyl, $(C_{6-12})$aryl$(C_{0-6})$alkyl, hetero$(C_{8-12})$polycycloaryl$(C_{0-6})$alkyl, $(C_{1-6})$alkylcarbonyl or $(C_{6-12})$arylcarbonyl wherein within $R^{22}$ any alicyclic or aromatic ring system present may be substituted further by 1 to 5 radicals independently selected from $(C_{1-6})$alkyl, $(C_{1-6})$alkylidene, cyano, halo, halo-substituted $(C_{1-4})$alkyl, nitro, —$X^4NR^{10}R^{10}$, —$X^4NR^{10}C(O)OR^{10}$, —$X^4NR^{10}C(O)NR^{10}R^{10}$, —$X^4NR^{10}C(NR^{10})NR^{10}R^{10}$, —$X^4OR^{10}$, —$X^4SR^{10}$, —$X^4C(O)OR^{10}$, —$X^4C(O)NR^{10}R^{10}$, —$X^4S(O)_2NR^{10}R^{10}$, —$X^4P(O)(OR^4)OR^{10}$, —$X^4OP(OR^4)OR^{10}$, —$X^4NR^{10}C(O)R^{11}$, —$X^4S(O)R^{11}$, —$X^4S(O)_2R^{11}$ and —$X^4C(O)R^{11}$, wherein $X^4$, $R^{10}$ and $R^{11}$ are as defined above; and the N-oxide derivatives, prodrug derivatives, protected derivatives, individual isomers and mixtures of isomers; and the pharmaceutically acceptable salts thereof.

A second aspect of this invention is a pharmaceutical composition which contains a compound of Formula I or a N-oxide derivative, prodrug derivative, individual isomer or mixture of isomers or a pharmaceutically acceptable salt thereof in admixture with one or more suitable excipients.

A third aspect of this invention is a method of treating a disease in an animal in which inhibition of a cysteine protease can prevent, inhibit or ameliorate the pathology and/or symptomatology of the disease, which method comprises administering to the animal a therapeutically effective amount of compound of Formula I or a N-oxide derivative, prodrug derivative, individual isomer or mixture of isomers or a pharmaceutically acceptable salt thereof.

A fourth aspect of this invention is the processes for preparing compounds of Formula I and the N-oxide derivatives, prodrug derivative, protected derivatives, individual isomers and mixtures of isomers, and the pharmaceutically acceptable salts thereof as set forth in "Detailed Description of the Invention".

A fifth aspect of this invention is a process for preparing a compound of Formula II:

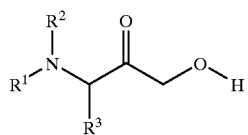

in which $R^1$ is peptidyl, $R^2$ is hydrogen or $(C_{1-6})$alkyl, $R^3$ is an amino acid side and $R^4$ is $(C_{1-6})$alkyl or $(C_{6-12})$aryl$(C_{1-6})$alkyl.

DETAILED DESCRIPTION OF THE INVENTION

Definitions

Unless otherwise stated, the following terms used in the specification and claims are defined for the purposes of this Application and have the meanings given this Section:

"Alicyclic" means a moiety characterized by arrangement of the carbon atoms in closed non-aromatic ring structures having properties resembling those of aliphatics and may be saturated or partially unsaturated with two or more double or triple bonds.

"Aliphatic" means a moiety characterized by straight or branched chain arrangement of the constituent carbon atoms and may be saturated or partially unsaturated with two or more double or triple bonds.

"Alkenyl" means alkyl, as defined in this Application, provided that the radical is comprised of at least one double bond. Hence, optionally substituted $(C_{2-6})$alkenyl as used in this Application to define $R^3$ includes 2-bromovinyl (—CH=CHBr), buta-1,3-dienyl (—CH=CH—CH=CH$_2$), 2-chloro-1-methylpropenyl (—C(CH$_3$)=CCl—CH$_3$), 2-chlorovinyl (—CH=CHCl), 4-isopropenyl (—C(CH$_3$)=CH$_2$), 1-methylpropenyl (—C(CH$_3$)=CH—CH$_3$), 2-methylpropenyl (—CH=C(CH$_3$)$_2$), 2-nitrovinyl (—CH=CHNO$_2$), propenyl (—CH=CH—CH$_3$), 2-trifluoromethylvinyl (—CH=CH—CF$_3$), trifluorovinyl (—CF=CF$_2$), vinyl (—CH=CH$_2$), and the like).

"Alkoxy" means the radical —OR, wherein R is alkyl as defined in this Application, having the number of carbon atoms indicated (e.g., $(C_{1-4})$alkoxy includes the radicals methoxy, ethoxy, propoxy, isopropoxy, butoxy, sec-butoxy, isobutoxy, tert-butoxy, vinyloxy, allyloxy, 1-propenyloxy, isopropenyloxy, 1-butenyloxy, 2-butenyloxy, 3-butenyloxy, 2-methylallyloxy, ethynyloxy, 1-propynyloxy, 2-propynyloxy, and the like).

"Alkyl" represented by itself means a straight or branched, saturated or unsaturated, aliphatic radical having the number of carbon atoms indicated (e.g. $(C_{1-6})$alkyl includes methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g. as in arylalkyl) means a straight or branched, saturated or unsaturated aliphatic divalent radical having the number of atoms indicated or when no atoms are indicated means a bond (e.g. $(C_{6-12})$aryl$(C_{0-6})$alkyl includes phenyl, benzyl, phenethyl, 1-phenylethyl 3-phenylpropyl, and the like).

"Alkylene", unless indicated otherwise, means a straight or branched, saturated or unsaturated, aliphatic, divalent radical having the number of carbon atoms indicated (e.g. $(C_{1-6})$alkylene includes methylene (—CH$_2$—), ethylene (—CH$_2$CH$_2$—), trimethylene (—CH$_2$CH$_2$CH$_2$—), 2-methyltrimethylene (—CH$_2$CH(CH$_3$)CH$_2$—), tetramethylene (—CH$_2$CH$_2$CH$_2$CH$_2$—), 2-butenylene (—CH$_2$CH=CHCH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like). For example, a group of Formula (a), wherein $R^{11}$ is hydrogen and $R^{12}$ taken together with $R^9$ forms optionally substituted trimethylene is depicted by the following illustration:

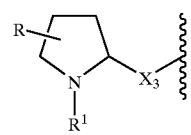

in which R is an optional hydroxy or oxo group and $X^3$ and $R^1$ are as defined in the Summary of the Invention for Formula I. Straight, saturated $(C_{2-5})$alkylene includes ethylene, trimethylene, tetramethylene and pentamethylene. For example, instances wherein $R^3$ and $R^4$ taken together form straight, saturated $(C_{2-5})$alkylene, wherein within said alkylene any one to two carbon atoms optionally is replaced by a heteroatom selected from —O—, —S— or —NR$^{28}$— wherein $R^{28}$ is hydrogen or $(C_{1-6})$alkyl, may be represented by, but are not limited to, the following illustrations:

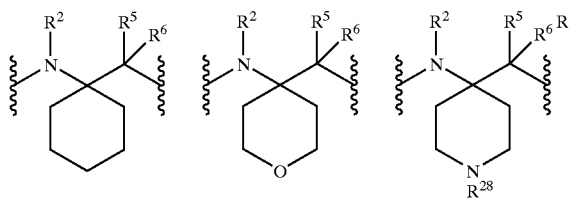

wherein $R^2$, $R^5$, $R^6$ and $R^{28}$ are as defined in the Summary of the Invention for Formulae I and II.

"Alkylidene" means a straight or branched saturated or unsaturated, aliphatic, divalent radical having the number of carbon atoms indicated (e.g. $(C_{1-6})$alkylidene includes methylene (=CH$_2$), ethylidene (=CHCH$_3$), isopropylidene (=C(CH$_3$)$_2$), propylidene (=CHCH$_2$CH$_3$), allylidene (=CHCH=CH$_2$), and the like).

"Amino" means the radical —NH$_2$. Unless indicated otherwise, the compounds of the invention containing amino moieties include protected derivatives thereof. Suitable protecting groups for amino moieties include acetyl, tert-butoxycarbonyl, benzyloxycarbonyl, and the like.

"Animal" includes humans, non-human mammals (e.g. dogs, cats, rabbits, cattle, horses, sheep, goats, swine, deer, or the like) and non-mammals (e.g. birds, or the like).

"Aryl" means a monocyclic or bicyclic ring assembly (fused or linked by a single bond) containing the total number of ring carbon atoms indicated, wherein each ring is comprised of 6 ring carbon atoms and is aromatic or when fused with a second ring forms an aromatic ring assembly. For example, $(C_{6-12})$aryl as used in this Application to define $R^1$ includes phenyl, naphthyl and biphenylyl.

"Aromatic" means a moiety wherein the constituent atoms make up an unsaturated ring system, all atoms in the ring system are sp2 hybridized and the total number of pi electrons is equal to 4n+2.

"Carbamoyl" means the radical —C(O)NH$_2$. Unless indicated otherwise, the compounds of the invention containing carbamoyl moieties include protected derivatives thereof. Suitable protecting groups for carbamoyl moieties include acetyl, tert-butoxycarbonyl, benzyloxycarbonyl, and the like and both the unprotected and protected derivatives fall within the scope of the invention.

"Carboxy" means the radical —C(O)OH. Unless indicated otherwise, the compounds of the invention containing carboxy moieties include protected derivatives thereof. Suitable protecting groups for carboxy moieties include benzyl, tert-butyl, and the like. For example, a compound of Formula I wherein $R^7$ contains a carboxy moiety may exist as either the unprotected or a protected derivative, e.g. wherein $R^7$ is methoxycarbonyl, and both the unprotected and protected derivatives fall within the scope of the invention.

"Cycloalkyl" means a saturated or partially unsaturated, monocyclic ring, bicyclic ring assembly (directly linked by a single bond or fused) or bridged polycyclic ring assembly containing the number of ring member carbon atoms indicated, and any carbocyclic ketone, thioketone or iminoketone derivative thereof (e.g. ($C_{3-12}$)cycloalkyl includes cyclopropyl, cyclobutyl, cyclopentyl, cyclohexyl, cyclohexenyl, 2,5-cyclohexadienyl, bicyclohexylyl, cyclopentylcyclohexyl, bicyclo[2.2.2]octyl, adamantan-1-yl, decahydronaphthalenyl, oxocyclohexyl, dioxocyclohexyl, thiocyclohexyl, 2-oxobicyclo[2.2.1]hept-1-yl, and the like).

"Disease" specifically includes any unhealthy condition of an animal or part thereof and includes an unhealthy condition which may be caused by, or incident to, medical or veterinary therapy applied to that animal, i.e., the "side effects" of such therapy.

"Guanidino" means the radical —NHC(NH)NH$_2$. Unless indicated otherwise, the compounds of the invention containing guanidino moieties include protected derivatives thereof. Suitable protecting groups for amino moieties include acetyl, tert-butoxycarbonyl, benzyloxycarbonyl, and the like and both the unprotected and protected derivatives fall within the scope of the invention.

"Halo" means fluoro, chloro, bromo or iodo.

"Halo-substituted alkyl", as a group or part of a group, means "alkyl" substituted by one or more "halo" atoms, as such terms are defined in this Application. Halo-substituted alkyl includes haloalkyl, dihaloalkyl, trihaloalkyl, perhaloalkyl and the like (e.g. halo-substituted ($C_{1-3}$)alkyl includes chloromethyl, dicloromethyl, difluoromethyl, trifluromethyl, 2,2,2-trifluoroethyl, perfluoroethyl, 2,2,2-trifluoro-1,1-dichloroethyl, and the like).

"Heteroaryl" means aryl, as defined herein, provided that one or more of the ring member carbon atoms indicated, is replaced by heteroatom moiety selected from —N=, —NR—, —O— or —S—, wherein R is hydrogen, ($C_{1-6}$) alkyl or a protecting group, and each ring contained therein is comprised of 5 to 6 ring member atoms. For example, hetero($C_{5-12}$)aryl as used in this Application includes benzofuryl, benzooxazolyl, benzothiazolyl, [2,4'] bipyridinylyl, carbazolyl, carbolinyl, chromenyl, cinnolinyl, furazanyl, furyl, imidazolyl, indazolyl, indolyl, indolizinyl, isobenzofuryl, isochromenyl, isooxazolyl, isoquinolyl, isothiazolyl, naphthyridinyl, oxazolyl, perimidinyl, 2-phenylpyridyl, phthalazinyl, pteridinyl, purinyl, pyrazinyl, pyradazinyl, pyrazolyl, pyridyl, pyrimidinyl, pyrrolizinyl, pyrrolidinyl, pyrrolyl, pyranyl, quinazolinyl, quinolizinyl, quinolyl, quinoxalinyl, tetrazolyl, thiazolyl, 4-thiazol-4-ylphenyl, thienyl, xanthenyl, and the like.

"Heteroatom moiety" includes —N=, —NR—, —O— or —S—, wherein R is hydrogen, ($C_{1-6}$)alkyl or a protecting group.

"Heterocycloalkyl" means cycloalkyl, as defined herein, provided that one or more of the ring member carbon atoms indicated is replaced by heteroatom moiety selected from —N=, —NR—, —O— or —S—, wherein R is hydrogen, ($C_{1-6}$)alkyl or a protecting group, and any carbocyclic ketone, thioketone or iminoketone derivative thereof (e.g. the term heterocyclo($C_{5-12}$)alkyl includes [1,4'] bipiperidinylyl, dihydrooxazolyl, morpholinyl, 1-morpholin-4-ylpiperidinyl, piperazinyl, piperidyl, pirazolidinyl, pirazolinyl, pyrrolinyl, pyrrolidinyl, quinuclidinyl, and the like). Suitable protecting groups include tert-butoxycarbonyl, benzyloxycarbonyl, benzyl, 4-methoxybenzyl, 2-nitrobenzyl, and the like. For example, a compound of Formula I wherein $R^1$ is piperidin-4-ylcarbonyl may exist as either the unprotected or a protected derivative, e.g. wherein $R^1$ is 1-tert-butoxycarbonylpiperidin-4-ylcarbonyl, and both the unprotected and protected derivatives fall within the scope of the invention.

"Heteropolycycloaryl" means polycycloaryl, as defined herein, except one or more of the ring member carbon atoms indicated are replaced by a heteroatom moiety selected from —N=, —NR—, —O— or —S—, wherein R is hydrogen, ($C_{1-6}$)alkyl or a protecting group, and any carbocyclic ketone, thioketone or iminoketone derivative thereof. For example, hetero($C_{8-12}$)polycycloaryl includes 1',2'-dihydro-2H-[1,4']bipyridinylyl, chromanyl, imidazolinyl, indolinyl, isochromanyl, isoindolinyl, and the like.

"Hydroxy" means the radical —OH. Unless indicated otherwise, the compounds of the invention containing hydroxy radicals include protected derivatives thereof. Suitable protecting groups for hydroxy moieties include benzyl and the like and both the unprotected and protected derivatives fall within the scope of the invention.

"Iminoketone derivative" means a derivative containing the moiety —C(NR)—, wherein R is hydrogen or ($C_{1-6}$) alkyl.

"Isomers" mean compounds of Formula I having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g. see "Advanced Organic Chemistry", 3rd edition, March, Jerry, John Wiley & Sons, New York, 1985). It is understood that the names and illustration used in this Application to describe compounds of Formula I are meant to be encompassed all possible stereoisomers and any mixture, racemic or otherwise, thereof.

"Ketone derivative" means a derivative containing the moiety —C(O)—.

"Nitro" means the radical —NO$_2$.

"Optional" or "optionally" means that the subsequently described event or circumstance may or may not occur, and that the description includes instances where the event or circumstance occurs and instances in which it does not. For example, the phrase "(C$_{1-6}$)alkyl optionally substituted with cyano, halo, nitro," means that the alkyl group referred to may or may not be substituted in order to fall within the scope of the invention.

"Oxalo" means the radical —C(O)C(O)OH.

"N-oxide derivatives" means a derivatives of compound of Formula I in which nitrogens are in an oxidized state (i.e., O←N) and which possess the desired pharmacological activity.

"Oxo" means the radical =O.

"Pathology" of a disease means the essential nature, causes and development of the disease as well as the structural and functional changes that result from the disease processes.

"Peptidyl" means a peptide residue, for example, of the general formula:

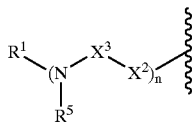

in which n is 1 or greater and each $X^2$, $X^3$, $R^1$ and $R^5$ are as defined in the Summary of the Invention for Formula I or any other peptide residue comprised of 1 or more contiguous natural or non-natural occurring amino acid moieties.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula I which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic hi acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, ammonium hydroxide, aluminum hydroxide and calcium hydroxide. Acceptable organic bases include ethanolamine, diethanolamine, triethanolamine, tromethamine, N-methylglucamine and the like.

"Phenylene-1,2-dimethylene" means the divalent radical —CH$_2$C$_6$H$_4$CH$_2$—, wherein the methylene moieties are attached at the 1- and 2-positions of the phenylene moiety. For example, a group of Formula (a), wherein $X^4$ is —CHR$^{12}$— in which R$^{12}$ together with R$^9$ forms optionally substituted phenylene-1,2-dimethylene is illustrated by the following formula:

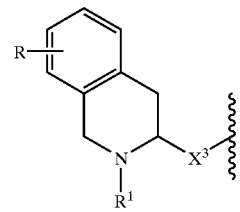

in which R is an optional hydroxy group and $X^3$ and $R^1$ are as defined in the Summary of the Invention for Formulae I and II.

"Polycycloaryl" means a bicyclic ring assembly (directly linked by a single bond or fused) containing the number of ring member carbon atoms indicated, wherein at least one, but not all, of the fused rings comprising the radical is aromatic, and any carbocyclic ketone, thioketone or iminoketone derivative thereof (e.g. (C$_{9-12}$)polycycloaryl includes indanyl, indenyl, 1,2,3,4-tetrahydronaphthalenyl, 1,2-dihydronaphthalenyl, cyclohexylphenyl, phenylcyclohexyl, 2,4-dioxo-1,2,3,4-tetrahydronaphthalenyl, and the like).

"Prodrug" means a compound which is convertible in vivo by metabolic means (e.g. by hydrolysis) to a compound of Formula (I). For example an ester of a compound of Formula (I) containing a hydroxy group may be convertible by hydrolysis in vivo to the parent molecule. Alternatively an ester of a compound of Formula (I) containing a carboxy group may be convertible by hydrolysis in vivo to the parent molecule. Suitable esters of compounds of Formula (I) containing a hydroxy group, are for example acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulphonates, ethanesulphonates, benzenesulphonates, p-toluenesulphonates, cyclohexylsulphamates and quinates. Suitable esters of compounds of Formula (I) containing a carboxy group, are for example those described by F. J. Leinweber, Drug Metab. Res., 1987, 18, page 379. An especially useful class of esters of compounds of Formula (I) containing a hydroxy group, may be formed from acid moieties selected from those described by Bundgaard et. al., J. Med. Chem., 1989, 32, page 2503–2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

"Protected derivatives" means derivatives of compounds of Formula I in which a reactive site or sites are blocked with protective groups. Protected derivatives of compounds of Formula I are useful in the preparation of compounds of Formula I or in themselves may be active cysteine protease inhibitors. A comprehensive list of suitable protective groups can be found in T. W. Greene, *Protective Groups in Organic Synthesis*, John Wiley & Sons, Inc. 1981.

"Sulfamoyl" means the radical —S(O)$_2$NH$_2$. Unless indicated otherwise, the compounds of the invention containing sulfamoyl radicals include protected derivatives thereof. Suitable protecting groups for sulfamoyl radicals include acetyl, tert-butoxycarbonyl, benzyloxycarbonyl, and the like and both the unprotected and protected derivatives fall within the scope of the invention.

"Therapeutically effective amount" means that amount which, when administered to an animal for treating a disease, is sufficient to effect such treatment for the disease.

"Thioketone derivative" means a derivative containing the moiety —C(S)—.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

"Trimethylene" means the divalent radical —CH$_2$CH$_2$CH$_2$—. For example, a group of Formula (a), wherein X$^3$ is —CHR$^7$— in which R$^7$ together with R$^1$ forms optionally substituted trimethylene is illustrated by the following formula:

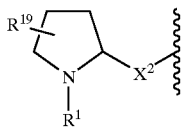

in which R$^{19}$ is an optional hydroxy or oxo group and X$^2$ and R$^1$ are as defined in the Summary of the Invention for Formula I.

"Ureido" means the radical —NHC(O)NH$_2$. Unless indicated otherwise, the compounds of the invention containing ureido moieties include protected derivatives thereof. Suitable protective groups for ureido moieties include acetyl, tert-butoxycarbonyl, benzyloxycarbonyl, and the like. For example, a compound of Formula I wherein the R$^1$ contains an ureido radical may exist as either the unprotected or a protected derivative and both the unprotected and protected derivatives fall within the scope of the invention.

Specific Embodiments

While the broadest definition of this invention is set forth in the Summary of the Invention, certain aspects of the invention are preferred. Preferred are compounds of Formula I in which:

X$^1$ is a bond or a divalent group of Formula (a) wherein:
  R$^5$ is hydrogen or together with R$^7$ forms phenylene-1,2-dimethylene; and
    R$^7$ is (i) (C$_{1-6}$)alkyl optionally substituted with —OR$^{10}$, —C(O)OR$^{10}$, —C(O)NR$^{10}$R$^{10}$, wherein R$^{10}$ at each occurrence independently is hydrogen or (C$_{1-6}$)alkyl or (ii) (C$_{6-12}$)aryl(C$_{0-3}$)alkyl, cyclo(C$_{3-12}$)alkyl(C$_{0-3}$)alkyl or (C$_{6-12}$)aryl(C$_{0-3}$)alkyl or (iii) together with R$^5$ is phenylenedimethylene; wherein within R$^7$ any alicyclic or aromatic ring system present may be substituted further by 1 to 5 radicals independently selected from (C$_{1-6}$)alkyl, (C$_{1-6}$)alkylidene, cyano, halo, halo-substituted (C$_{1-4}$)alkyl, nitro, —X$^4$NR$^{10}$R$^{10}$, —X$^4$NR$^{10}$C(O)OR$^{10}$, —X$^4$NR$^{10}$C(O)NR$^{10}$R$^{10}$, —X$^4$NR$^{10}$C(NR$^{10}$)NR$^{10}$R$^{10}$, —X$^4$OR$^{10}$, —X$^4$SR$^{10}$, —X$^4$C(O)OR$^{10}$, —X$^4$C(O)NR$^{10}$R$^{10}$, —X$^4$S(O)$_2$NR$^{10}$R$^{10}$, —X$^4$P(O)(OR$^4$)OR$^{10}$, —X$^4$OP(O)(OR$^4$)OR$^{10}$, —X$^4$NR$^{10}$C(O)R$^{11}$, —X$^4$S(O)R$^{11}$, —X$^4$S(O)$_2$R$^{11}$ and —X$^4$C(O)R$^{11}$, wherein X$^4$ is a bond or (C$_{1-6}$)alkylene, R$^{10}$ at each occurrence independently is hydrogen, (C$_{1-6}$)alkyl or halo-substituted (C$_{1-3}$)alkyl and R$^{11}$ is C$_{1-6}$)alkyl or halo-substituted (C$_{1-3}$)alkyl;

R$^1$ is —X$^6$X$^7$R$^{16}$, wherein X$^6$ is —C(O)— or —S(O)$_2$—, X$^7$ is a bond, —O— or —NR$^{17}$—, wherein R$^{17}$ is hydrogen or (C$_{1-6}$)alkyl, and R$^{16}$ is (i) (C$_{1-6}$)alkyl optionally substituted with —C(O)OR$^{10}$, —NR$^{10}$R$^{10}$ or —NR$^{10}$C(O)OR$^{10}$, wherein R$^{10}$ at each occurrence independently is hydrogen or (C$_{1-6}$)alkyl or (ii) hetero(C$_{3-14}$)cycloalkyl(C$_{0-6}$)alkyl, (C$_{6-14}$)aryl(C$_{0-6}$)alkyl, diphenyl(C$_{0-6}$)alkyl, or hetero(C$_{5-14}$)aryl (C$_{0-6}$)alkyl; wherein within R$^7$ any alicyclic or aromatic ring system present may be substituted further by 1 to 5 radicals independently selected from (C$_{1-6}$)alkyl, (C$_{1-6}$)alkylidene, cyano, halo, halo-substituted (C$_{1-4}$)alkyl, nitro, —X$^4$NR$^{10}$R$^{10}$, —X$^4$NR$^{10}$C(O)OR$^{10}$, —X$^4$NR$^{10}$C(O)NR$^{10}$R$^{10}$, —X$^4$NR$^{10}$C(NR$^{10}$)NR$^{10}$R$^{10}$, —X$^4$OR$^{10}$, —X$^4$SR$^{10}$, —X$^4$C(O)OR$^{10}$, —X$^4$C(O)NR$^{10}$R$^{10}$, —X$^4$S(O)$_2$NR$^{10}$R$^{10}$, —X$^4$P(O)(OR$^4$)OR$^{10}$, —X$^4$OP(O)(OR$^4$)OR$^{10}$, —X$^4$NR$^{10}$C(O)R$^{11}$, —X$^4$S(O)R$^{11}$, —X$^4$S(O)R$^{11}$, —X$^4$S(O)$_2$R$^{11}$ and —X$^4$C(O)R$^{11}$, wherein X$^4$, R$^{10}$ and R$^{11}$ are as defined above;

R$^2$ is hydrogen;

R$^3$ is (i) hydrogen or (C$_{1-6}$)alkyl optionally substituted with —OR$^{20}$, —NR$^{21}$C(O)OR$^{20}$, —C(O)NR$^{20}$R$^{21}$, —S(O)$_2$R$^{20}$, wherein R$^{20}$ is (C$_{0-6}$)alkyl or (C$_{0-10}$)aryl (C$_{0-6}$)alkyl and R$^{21}$ is hydrogen or (C$_{1-6}$)alkyl, or (ii) (C($_{6-10}$)aryl(C$_{1-6}$)alkyl or (C$_{5-10}$)heteroaryl(C$_{1-6}$)alkyl or (ii) together with R$^2$ forms trimethylene or phenylene-1,2-dimethylene; wherein within R$^7$ any alicyclic or aromatic ring system present may be substituted further by 1 to 5 radicals independently selected from (C$_{1-6}$)alkyl, (C$_{1-6}$)alkylidene, cyano, halo, halo-substituted (C$_{1-4}$)alkyl, nitro, —X$^4$NR$^{10}$R$^{10}$, —X$^4$NR$^{10}$C(O)OR$^{10}$, —X$^4$NR$^{10}$C(O)NR$^{10}$R$^{10}$, —X$^4$NR$^{10}$C(NR$^{10}$)NR$^{10}$R$^{10}$, —X$^4$OR$^{10}$, —X$^4$SR$^{10}$, —X$^4$C(O)OR$^{10}$, —X$^4$C(O)NR$^{10}$R$^{10}$, —X$^4$S(O)$_2$NR$^{10}$R$^{11}$, —X$^4$P(O)(OR$^4$)OR$^{10}$, —X$^4$OP(O)(OR$^4$)OR$^{10}$, —X$^4$NR$^{10}$C(O)R$^{11}$, —X$^4$S(O)R$^{11}$, —X$^4$S(O)$_2$R$^{11}$ and —X$^4$C(O)R$^{11}$, wherein X$^4$, R$^{10}$ and R$^{11}$ are as defined above; and R$^4$ is nitromethyl, 1-hydroxy-1-methylethyl or —CH$_2$OR$^{22}$, wherein R$^{22}$ is hydrogen, (C$_{1-6}$)alkyl, (C$_{6-12}$)aryl(C$_{0-6}$)alkyl, heteropolycyclo(C$_{8-12}$)aryl(C$_{0-6}$)alkyl, (C$_{1-6}$)alkylcarbonyl or (C$_{6-12}$)arylcarbonyl, wherein within R$^4$ any aromatic ring present may be substituted further by 1 to 3 radicals independently selected from halo, —OR$^{10}$, —C(O)NR$^{10}$R$^{10}$, —S(O)$_2$NR$^{10}$R$^{10}$ or —X$^4$NR$^{10}$R$^{10}$, wherein X$^4$, R$^{10}$ and R$^{11}$ are as defined above; and the N-oxide derivatives, prodrug derivatives, protected derivatives, individual isomers and mixtures of isomers; and the pharmaceutically acceptable salts thereof.

Preferred are compounds of Formula I in which within Formula (a):

R⁵ is hydrogen or as defined below; and

R⁷ is (i) butyl, ethyl, methyl, 1-methylethyl, 1-methylpropyl or 2-methylpropyl optionally substituted with —OR¹⁰, —C(O)OR¹⁰, —NR¹⁰R¹⁰, —NR¹⁰C(O)OR¹⁰ or —C(O)NR¹⁰R¹⁰, wherein R¹⁰ is hydrogen or (C₁₋₆)alkyl, or (ii) benzyl, benzyloxycarbonylmethyl, biphenyl-4-ylmethyl, cyclohexyl, cyclohexylmethyl, naphth-2-ylmethyl, phenylcarbamoylmethyl or phenylethyl or (iii) together with R⁵ is phenylenedimethylene; wherein within R⁷ any alicyclic or aromatic ring system present may be substituted further by 1 to 3 radicals independently selected from nitro and amino;

R¹ is hydrogen, acetyl, 3-aminobenzoyl, 4-aminobutyryl, 3-aminopropionyl, 6-aminohexanoyl, 3-aminomethylbenzoyl, 4-aminomethylbenzoyl, benzoyl, benzylcarbamoyl, 4-benzyloxybenzoyl, benzyloxycarbonyl, tert-butoxycarbonyl, 3-tert-butoxycarbonylaminobenzoyl, 4-tert-butoxycarbonylaminobutyryl, 6-tert-butoxycarbonylaminohexanoyl, 3-tert-butoxycarbonylaminomethylbenzoyl, 4-tert-butoxycarbonylaminomethylbenzoyl, 1-tert-butoxycarbonylpiperidin-4-ylcarbonyl, 1-tert-butoxycarbonylpyrrolidin-2-ylcarbonyl, 3-carbamoylbenzoyl, 3-cyanobenzoyl, dibenzofur-2-ylsulfonyl, 3-[N',N"-di(tert-butoxycarbonyl)guanidino]benzoyl, 4-dimethylaminobenzoyl, 2,2-dimethylpropionyl, 3-diphenylpropionyl, 3-fluorobenzoyl, 3-guanidinobenzoyl, 3-hydroxybenzoyl, 1H-indol-3-ylacetyl, 3-methoxycarbonylbenzoyl, 3-methoxycarbonylpropionyl, 3-methoxyphenylcarbamoyl 4-methylpiperazin-1-ylcarbonyl, morpholin-4-ylcarbonyl, naphth-1-ylcarbonyl, naphth-2-ylcarbonyl naphth-2-ylsulfonyl, 3-nitrophenylacetyl, phenoxyacetyl, phenylcarbamoyl, 3-phenylpropionyl, piperidin-4-ylcarbonyl, 1-piperidin-1-ylpiperidin-1-ylcarbonyl, pyrid-3-ylacetyl, pyrid-4-ylacetyl, pyrid-3-ylcarbonyl, pyrid-4-ylcarbonyl, pyrrolidin-2-ylcarbonyl, pyrazinylcarbonyl or 3-ureidobenzoyl;

R² is hydrogen or as defined below;

R³ is hydrogen, benzyl, 2-benzyloxyethyl, 4-benzyloxycarbonylaminobutyl, benzyloxymethyl, butyl, 2-(4-hydroxyphenyl)ethyl, 1H-indol-3-ylmethyl, 4-methoxybenzyl, methyl, 2-methylsulfonylethyl, 2-methylpropyl, phenethyl, 2-phenylcarbamoylethyl or together with R² forms tetramethylene or phenylenedimethylene; and R⁴ is acetoxymethyl, benzo[1,3]dioxol-5-yloxy, benzyloxymethyl, 4-carbamoylphenoxymethyl, 4-chlorophenoxymethyl, 2,5-dichlorobenzoyloxymethyl, 2,6-dichlorobenzoyloxymethyl, 3-dimethylaminophenoxymethyl, ethoxymethyl, hydroxymethyl, 1-hydroxy-1-methylethyl, 4-(1H-imidazol-1-yl)phenoxymethyl, methoxymethyl, 3-methoxyphenoxymethyl, 4-methoxyphenoxymethyl, 4-sulfamoylphenoxymethyl or phenoxymethyl; and the N-oxide derivatives, prodrug derivatives, protected derivatives, individual isomers and mixtures of isomers; and the pharmaceutically acceptable salts thereof.

Preferred are compounds of Formula I in which within Formula (a), R⁵ is hydrogen and R⁷ is butyl, 1-methylethyl, 1-methylpropyl, 2-methylpropyl or naphth-2-ylmethyl; R¹ is 3-aminobenzoyl, 3-aminomethylbenzoyl, 4-aminomethylbenzoyl, benzoyl, benzylcarbamoyl, benzyloxycarbonyl, tert-butoxycarbonyl, 3-tert-butoxycarbonylaminobenzoyl, 4-tert-butoxycarbonylaminomethylbenzoyl, 3-[N',N"-di(tert-butoxycarbonyl)guanidino]benzoyl, 4-dimethylaminobenzoyl, 3-guanidinobenzoyl 4-methylpiperazin-1-ylcarbonyl, naphth-1-ylcarbonyl, naphth-2-ylcarbonyl or piperidin-4-ylcarbonyl; R² is hydrogen; R³ is hydrogen, 4-benzyloxycarbonylaminobutyl, butyl or phenethyl; and R⁴ is benzyloxymethyl, hydroxymethyl, 2,5-dichlorobenzoyloxymethyl, ethoxymethyl, 1-hydroxy-1-methylethyl or phenoxymethyl; and the N-oxide derivatives, prodrug derivatives, protected derivatives, individual isomers and mixtures of isomers; and the pharmaceutically acceptable salts thereof.

Pharmacology and Utility

The compounds of the invention are cysteine protease inhibitors, in particular the compounds of the invention inhibit the activity of cathepsins B, L, K and/or S and, as such, are useful for treating diseases in which cathepsin B, L, K and/or S activity contributes to the pathology and/or symptomatology of the disease. For example, the compounds of the invention are useful in treating tumor invasion and metastasis, in particular as anti-angiogenic agents, rheumatoid arthritis, osteo arthritis, pneumocystis carinii, acute pancreatitis, inflammatory airway disease and bone and joint disorders. Furthermore, the compounds of the invention are useful in treating bone resorption disorders, e.g., osteoporosis. The compounds of the invention also are useful in treating autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis, allergic disorders, including, but not limited to asthma, and allogeneic immune reponses, including, but not limited to, organ transplants or tissue grafts.

The cysteine protease inhibitory activities of the compounds of the invention can be determined by methods known to those of ordinary skill in the art. Suitable in vitro assays for measuring protease activity and the inhibition thereof by test compounds are known. Typically, the assay measures protease induced hydrolysis of a peptide based substrate. Details of assays for measuring protease inhibitory activity are set forth in Examples 7, 8, 9 and 10, infra.

Nomenclature

The compounds of Formula I and the intermediates and starting materials used in their preparation are named in accordance with IUPAC rules of nomenclature in which the characteristic groups have decreasing priority for citation as the principle group as follows: acids, esters, amides, etc. For example, a compound of Formula I in which X¹ is a divalent group of Formula (a), wherein X² is —C(O)—, R⁷ is isobutyl and R⁵ and R⁹ both are hydrogen; R¹ is benzyloxycarbonyl; R² is hydrogen; R³ is phenethyl; and R⁴ is methoxymethyl; that is, a compound having the following structure:

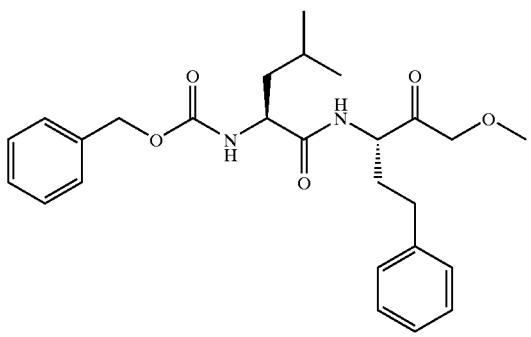

is named benzyl 1S-(3-hydroxy-2-oxo-1S-phenethylpropylcarbamoyl)-3-methylbutylcarbamate; and a compound of Formula I in which $X^1$ is a divalent group of Formula (a), wherein $X^2$ is —C(O)—, $R^7$ is isobutyl and $R^5$ and $R^9$ both are hydrogen; $R^1$ is benzyloxycarbonyl; $R^2$ is hydrogen; $R^3$ is phenethyl; and $R^4$ is 2,5-dichlorobenzoyl; that is, a compound having the following structure:

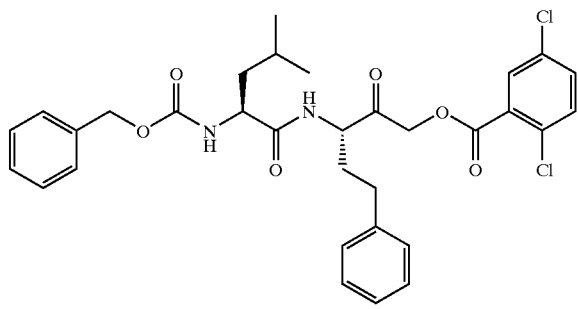

is named 3S-(2S-benzyloxycarbonylamino-4-methylpentanoylamino)-2-oxo-5-phenylpenyl 2,5-dichlorobenzoate; and a compound of Formula I in which $X^1$ is a divalent group of Formula (a), wherein $X^2$ is —C(O)—, $R^7$ is 1-methylpropyl and $R^5$ and $R^9$ both are hydrogen; $R^1$ is 3-aminomethylbenzoyl; $R^2$ is hydrogen; $R^3$ is phenethyl; and $R^4$ is hydroxymethyl; that is, a compound having the following structure:

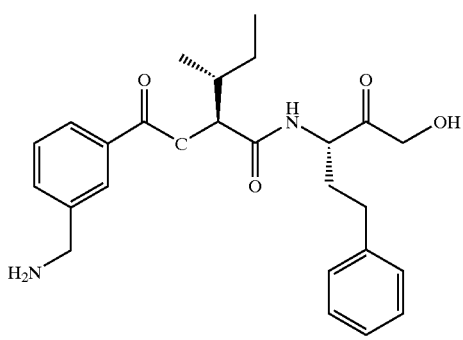

is named 3-aminomethyl-N-[1S-(3-hydroxy-2-oxo-1S-phenethylpropylcarbamoyl)-2-methylbutyl]benzamide.

Administration and Pharmaceutical Compositions

In general, compounds of Formula I will be administered in therapeutically effective amounts via any of the usual and acceptable modes known in the art, either singly or in combination with another therapeutic agent. A therapeutically effective amount may vary widely depending on the severity of the disease, the age and relative health of the subject, the potency of the compound used and other factors. For example, therapeutically effective amounts of a compound of Formula I may range from 0.1 micrograms per kilogram body weight (μg/kg) per day to 10 milligram per kilogram body weight (mg/kg) per day, typically to 1 μg/kg/day to 1 mg/kg/day. Therefore, a therapeutically effective amount for a 80 kg human patient may range from 10 μg/day to 100 mg/day, typically 0.1 mg/day to 10 mg/day. In general, one of ordinary skill in the art, acting in reliance upon personal knowledge and the disclosure of this Application, will be able to ascertain a therapeutically effective amount of a compound of Formula I for treating a given disease.

The compounds of Formula I can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, or the like). Preferred liquid carriers, particularly for injectable solutions, include water, saline, aqueous dextrose and glycols.

The amount of a compound of Formula I in the composition may vary widely depending upon the type of formulation, size of a unit dosage, kind of excipients and other factors known to those of skill in the art of pharmaceutical sciences. In general, a composition of a compound of Formula I for treating a given disease will comprise from 0.01%w to 10%w, preferably 0.3%w to 1%w, of active ingredient with the remainder being the excipient two or excipients. Preferably the pharmaceutical composition is administered in a single unit dosage form for continuous treatment or in a single unit dosage form ad libitum when relief of symptoms is specifically required. Representative pharmaceutical formulations containing a compound of Formula I are described in Example 11.

The compounds of Formula I can be administered alone or in combination with other compounds of Formula I or in combination with one or more other active ingredient(s). For example, the compounds of Formula I can be administered in combination with a therapeutically active amount of a bisphosphonic acid or acid ester derivative or any pharmaceutically acceptable salt thereof. Suitable bisphosphonic acids and acid ester derivatives include compounds corresponding to the following formula:

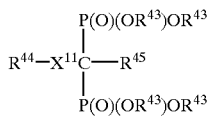

wherein $X^{11}$ is a bond or $(C_{1-7})$alkylene, each $R^{43}$ independently is hydrogen or $(C_{1-30})$alkyl, $R^{44}$ and $R^{45}$ are selected independently from a group consisting of hydrogen, halo, optionally substituted $(C_{1-30})$alkyl, $(C_{3-30})$cycloalkyl, hetero $(C_{5-30})$cycloalkyl, optionally substituted $(C_{6-10})$aryl, hetero $(C_{6-10})$aryl, —$NR^{46}R^{46}$, —$OR^{46}$, —$SR^{46}$, wherein each $R^{46}$ independently is hydrogen, $(C_{1-10})$alkyl, $(C_{3-10})$cycloalkyl, optionally substituted $(C_{6-10})$aryl, provided that both $R^{44}$ and $R^{45}$ are not selected from hydrogen or hydroxy when $X^{11}$ is a bond; or $R^{44}$ and $R^{45}$ taken together form $(C_{2-9})$ alkylene; wherein $(C_{3-10})$cycloalkyl includes adamantyl and the like, hetero$(C_{5-10})$cycloalkyl includes pyrrolidinyl and the like, $(C_{6-10})$aryl includes phenyl and naphthyl, and hetero$(C_{6-10})$aryl includes quinolyl, isoquinolyl, pyridyl, furyl, imidazolyl, imidazopyridyl and the like.

Instances wherein $R^{44}$ and/or $R^{45}$ are substituted $(C_{1-30})$ alkyl may include, but are not limited to, $(C_{1-30})$alkyl substituted by hetero$(C_{5-10})$cycloalkyl, $(C_{6-10})$aryl, hetero $(C_{6-10})$aryl, —$NR^{47}R^{47}$, —$OR^{47}$ and —$SR^{47}$, wherein each $R^{47}$ is independently hydrogen or $(C_{6-10})$alkyl; wherein hetero$(C_{5-10})$cycloalkyl includes pyrrolidinyl and the like, $(C_{6-10})$aryl includes phenyl and naphthyl, and hetero$(C_{6-10})$ aryl includes quinolyl, isoquinolyl, pyridyl, furyl, imidazolyl, imidazopyridyl and the like. Suitable optionally substituted aryl groups include, but are not limited to, halo-substituted phenyl.

A non-limiting class of bisphosphonic acids and acid ester derivatives thereof suitable for administration in combination with compounds of Formula I include those in which $R^4$ is selected from the group consisting of hydrogen, hydroxy or halo, and $R^{45}$ is selected from the group consisting of optionally substituted $(C_{1-30})$alkyl, halo and —$SR^{46}$, wherein $R^{46}$ is $(C_{1-10})$alkyl or phenyl.

A non-limiting subclass of bisphosphonic acids and acid ester derivatives thereof suitable for administration in combination with compounds of Formula I include those in which $R^{44}$ is selected from the group consisting of hydrogen, hydroxy and chloro and $R^{45}$ is selected from the group consisting of optionally substituted $(C_{1-30})$alkyl, chloro and chlorophenylthio.

A non-limiting example of a bisphosphonic acid suitable for administration in combination with compounds of Formula I include that in which $X^{11}$ is a bond, each $R^{43}$ is hydrogen, $R^{44}$ is hydroxy and $R^{45}$ is 3-aminopropyl, namely 4-amino-1-hydroxybutylidene-1,1-bisphosphonic acid (aka alendronic acid), or the monosodium trihydrate salt thereof, namely 4-amino-1-hydroxybutylidene-1,1-bisphosphonate monosodium trihydrate (aka alendronate monosodium trihydrate), described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which patents are incorporated by reference herein in their entirety.

Further non-limiting examples of bisphosphonic acids suitable for administration in combination with compounds of Formula I include the following:

cycloheptylaminomethylene-1,1-bisphosphonic acid (aka cimadronic acid), described in U.S. Pat. No. 4,970,335, to Isomura et al., issued Nov. 13, 1990;

1,1-dichloromethylene-1,1-diphosphonic acid (aka clodronic acid) and the disodium salt thereof, namely clodronate disodium, described in Belgium Patent 672,205 (1966) and *J. Org. Chem* 32, 4111 (1967);

1-hydroxy-3-pyrrolidin-1-ylpropylidene-1,1-bisphosphonic acid (aka EB-1053);

1-hydroxyethylidene-1,1-diphosphonic acid (aka etidronic acid);

1-hydroxy-3-(N-methyl-N-pentylamino)propylidene-1,1-bisphosphonic acid (aka ibandronic acid), described in U.S. Pat. No. 4,927,814, issued May 22, 1990;

6-amino-1-hydroxyhexylidene-1,1-bisphosphonic acid (aka neridronic acid);

3-(dimethylamino)-1-hydroxypropylidene-1,1-bisphosphonic acid (aka olpadronic acid);

3-amino-1-hydroxypropylidene-1,1-bisphosphonic acid (aka pamidronic acid);

2-pyrid-2-ylethylidene-1,1-bisphosphonic acid (aka piridronic acid), described in U.S. Pat. No. 4,761,406;

1-hydroxy-2-pyrid-3-ylethylidene-1,1-bisphosphonic acid (aka risedronic acid);

4-chlorophenylthiomethylenebisphosphonic acid (aka tiludronic acid), described in U.S. Pat. No. 4,876,248, to Breliere et al., Oct. 24, 1989; and 1-hydroxy-2-(1H-midazol-1-yl)ethylidene-1,1-bisphosphonic acid (aka zoledronic acid); all of which patents and other documents referred to above are incorporated by reference herein in their entirety.

A non-limiting subclass of bisphosphonic acids suitable for administration in combination with compounds of Formula I include those selected from the group consisting of alendronic acid, cimadronic acid, clodronic acid, tiludronic acid, etidronic acid, ibandronic acid, risedronic acid, piridronic acid, pamidronic acid, zolendronic acid, pharmaceutically acceptable salts thereof, and mixtures thereof. A further example of a bisphosphonic acid suitable for administration in combination with compounds of Formula I is alendronic acid or a pharmaceutically acceptable salt thereof, and mixtures thereof. A further non-limiting example is alendronate monosodium trihydrate.

Compounds of Formula I can be administered in combination with a therapeutically active amount of an estrogen receptor agonist. Non-limiting examples of estrogen receptor agonists suitable for administration in combination with the compounds of Formula I include naturally occurring estrogens such as estradiol, estrone and estroil, or synthetic estrogen receptor agonists such as [6-hydroxy-2-(4-hydroxyphenyl)benzo[b]thien-3-yl][4-(2-piperidin-1-ylethoxy)phenyl]methanone (aka raloxifene) and {2-[4-(1, 2-diphenylbut-1-enyl)phenoxy]ethyl}dimethylamine (aka tamoxifen). A non-limiting subclass of estrogen receptor agonists suitable for administration in combination with the compounds of Formula I include estrogen receptor partial agonists (i.e., estrogen receptor agonists with mixed agonist/antagonist properties), sometimes referred to as estrogen receptor modulators. Estrogen receptor partial agonists can exert tissue-selective estrogen agonist effects. Tamoxifen, for example, selectively exerts an estrogen agonist effect on the bone, in humans. Additional suitable estrogen receptor partial agonists are described in Tissue-Selective Actions Of Estrogen Analogs, Bone Vol. 17, No. 4, October 1995, 181S–190S. Certain 3-[4-(2-phenylindol-1-ylmethyl) phenyl]acrylamides, described in U.S. Pat. No. 5,985,910 to Miller et al., Nov. 16, 1999; benzothiphene compounds, described in U.S. Pat. No. 5,985,897 to Meuhl et al., Nov.

16, 1999; naphthyl compounds, described in U.S. Pat. No. 5,952,350 to Cullinan et al., Sep. 14, 1999; substituted benzothiophene compounds, described in U.S. Pat. No. 5,962,475 to Schmid et al., Oct. 4, 1999, are suitable estrogen receptor partial agonists for administration with the compounds of Formula I; all of which patents and other documents referred to above are incorporated by reference herein in their entirety.

More particularly a pharmaceutical composition of this invention may comprise a therapeutically effect amount of a compound of Formula I in combination with one or more active ingredient(s) selected from the group consisting of (i) a therapeutically effect amount of a bisphosphonic acid or acid ester thereof or a pharmaceutically acceptable salt thereof and (ii) a therapeutically effect amount of an estrogen receptor agonist or a pharmaceutically acceptable salt thereof; and one or more pharmaceutically acceptable excipient(s). Non-limiting examples of such bisphosphonic acids include 1,1-dichloromethylene-1,1-diphosphonic acid, 1-hydroxy-3-pyrrolidin-1-ylpropylidene-1,1-bisphosphonic acid, 1-hydroxyethylidene-1,1-diphosphonic acid, 1-hydroxy-3-(N-methyl-N-pentylamino)propylidene-1,1-bisphosphonic acid, 6-amino-1-hydroxyhexylidene-1,1-bisphosphonic acid, 3-(dimethylamino)-1-hydroxypropylidene-1,1-bisphosphonic acid, 3-amino-1-hydroxypropylidene-1,1-bisphosphonic acid, 2-pyrid-2-ylethylidene-1,1-bisphosphonic acid, 1-hydroxy-2-pyrid-3-ylethylidene-1,1-bisphosphonic acid, 4-chlorophenylthiomethylenebisphosphonic acid and 1-hydroxy-2-(1H-imidazol-1-yl)ethylidene-1,1-bisphosphonic acid or acid ester thereof or a pharmaceutically acceptable salt thereof; particularly 1,1-dichloromethylene-1,1-diphosphonic acid or a pharmaceutically acceptable salt thereof and preferably 1,1-dichloromethylene-1,1-diphosphonate monosodium trihydrate.

Chemistry

Processes for Making Compounds of Formula I:

Compounds of Formula I in which $R^4$ is nitromethyl or —$CH_2OR^{18}$ can be prepared by proceeding as in the following Scheme 1:

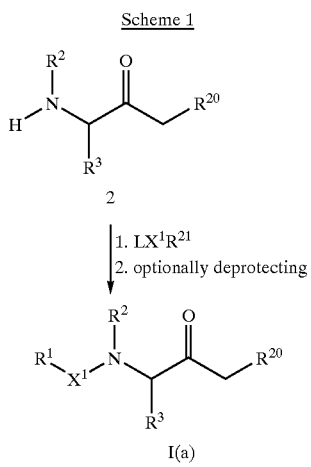

in which L is a leaving group, $R^{20}$ is —$OR^{22}$, wherein $R^{22}$ is a hydroxy protecting group or optionally substituted $(C_{1-6})$alkyl, $(C_{6-12})$aryl$(C_{0-6})$alkyl, heteropolycyclo$(C_{8-12})$aryl$(C_{0-6})$alkyl, $(C_{1-6})$alkylcarbonyl or $(C_{6-12})$arylcarbonyl, $R^{21}$ is $R^1$ or a protecting group and each $X^1$, $R^1$, $R^2$ and $R^3$ are as defined in the Summary of the Invention for Formula I.

Compounds of Formula I in which $R^{14}$ is nitromethyl or —$CH_2OR^{18}$ (Formula I(a)) can be prepared by condensing a compound of Formula 2 with a compound of the formula $LX^1R^{21}$, and then removing one or more protecting groups if necessary. The compound of Formula 2 may be in a free base or an acid addition salt form, preferably an acid addition salt form (e.g., p-toluenesulfonic acid salt, or the like). Typically the condensation reaction is carried out under nitrogen in the presence of a suitable condensing agent (e.g., isobutyl chloroformate, or the like), a base (e.g., 4-methylmorpholine, triethylamine, or the like) and a suitable solvent (e.g., tetrahydrofuran (THF), or the like), at −20 to 0° C., preferably at about −10° C., and requires 45 minutes to 4 hours to complete. A detailed description of the condensation reaction is found in Example 2, infra. Deprotection can be effected by any means which removes the protective group and gives the desired product in reasonable yield. A detailed description of a deprotection procedure is found in Example 3, infra.

Compounds of Formula I in which $R^4$ is —$CH_2OR^{18}$ can be prepared by proceeding as in the following reaction Scheme 2:

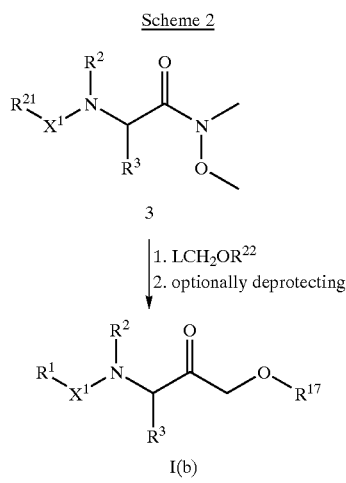

in which L is a leaving group, $R^{22}$ is a hydroxy protecting group or optionally substituted $(C_{1-6})$alkyl, $(C_{6-12})$aryl$(C_{0-6})$alkyl, heteropolycyclo$(C_{8-12})$aryl$(C_{0-6})$alkyl, $(C_{1-6})$alkylcarbonyl or $(C_{6-12})$arylcarbonyl, $R^{20}$ is $R^1$ or a protecting group and each $X^1$, $R^1$, $R^2$, $R^3$ and $R^{17}$ are as defined in the Summary of the Invention for Formula I.

Compounds of Formula I in which $R^4$ is —$CH_2OR^{18}$ (Formula I(b)) can be prepared by condensing a compound of Formula 3 with a compound of the formula $LCH_2OR^{22}$ and then removing one or more protecting groups if necessary. Typically the condensation reaction is carried out under nitrogen in a suitable solvent (e.g., THF) at −60 to 25° C. and requires 10 to 20 hours to complete. A detailed description of the preparation of a compound of Formula I(c) is found in Example 1, infra.

Compounds of Formula I in which $R^4$ is 1-hydroxy-1-methylethyl can be prepared by proceeding as in the following reaction Scheme 3:

Scheme 3

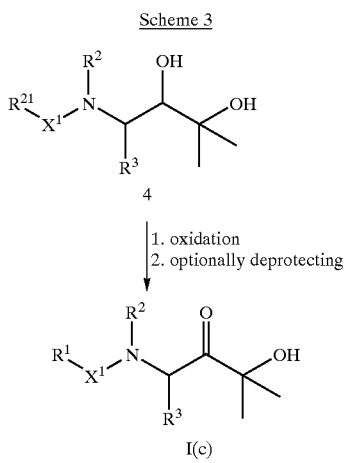

in which $R^{21}$ is $R^1$ or a protecting group and each $X^1$, $R^1$, $R^2$ and $R^3$ are as defined in the Summary of the Invention for Formula I.

Compounds of Formula I in which $R^4$ is 1-hydroxy-1-methylethyl (Formula I(c)) can be prepared by oxidizing a compound of Formula 4 and then deprotecting if necessary. Typically the oxidation is carried out with a suitable oxidizing agent (e.g., Dess-Martin periodinate, or the like) in a suitable solvent (e.g., methylene chloride, or the like) at 15 to 25° C. and requires 10 to 20 hours to complete. A detailed description of the preparation of a compound of Formula I(c) is found in Example 4, infra.

Compounds of Formula I in which $R^4$ is nitromethyl can be prepared by proceeding as in the following Scheme 4:

Scheme 4

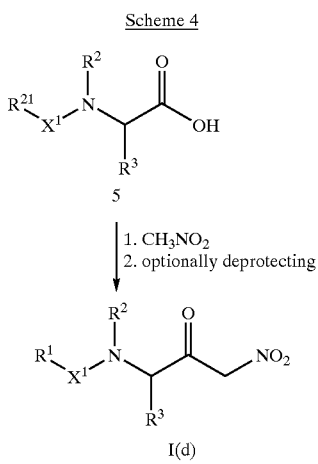

in which $R^{21}$ is $R^1$ or a protecting group and each $X^1$, $R^1$, $R^2$ and $R^3$ are as defined in the Summary of the Invention for Formula I.

Compounds of Formula I in which $R^4$ is nitromethyl (Formula I(d)) can be prepared by reacting a compound of Formula 5 with nitromethane and then deprotecting if necessary. Typically the reaction with the nitromethane is carried out under nitrogen in the presence of a coupling agent (e.g., 1,1'-carbonyldiimidazole, or the like) and in a suitable solvent (e.g., TBF) at −10 to 25° C. and requires 10 to 20 hours to complete.

Additional Processes for Preparing Compounds of Formula I:

A compound of Formula I can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula I can be prepared by reacting the free acid form of the compound with a pharmaceutically acceptable inorganic or organic base. Inorganic and organic acids and bases suitable for the preparation of the pharmaceutically acceptable salts of compounds of Formula I are set forth in the definitions section of this application. Alternatively, the salt forms of the compounds of Formula I can be prepared using salts of the starting materials or intermediates.

The free acid or free base forms of the compounds of Formula I can be prepared from the corresponding base addition salt or acid addition salt form. For example, a compound of Formula I in an acid addition salt form can be converted to the corresponding free base by treating with a suitable base (e.g., ammonium hydroxide solution, sodium hydroxide, or the like). A compound of Formula I in a base addition salt form can be converted to the corresponding free acid by treating with a suitable acid (e.g., hydrochloric acid, etc).

The N-oxides of compounds of Formula I can be prepared by methods known to those of ordinary skill in the art. For example, N-oxides can be prepared by treating an unoxidized form of the compound of Formula I with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as methylene chloride) at approximately 0° C. Alternatively, the N-oxides of the compounds of Formula I can be prepared from the N-oxide of an appropriate starting material.

Compounds of Formula I in unoxidized form can be prepared from N-oxides of compounds of Formula I by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds of Formula I can be prepared by methods known to those of ordinary skill in the art (e.g., for further details see Saulnier et al. (1994), *Bioorganic and Medicinal Chemistry Letters*. 4:1985). For example, appropriate prodrugs can be prepared by reacting a non-derivatized compound of Formula I with a suitable carbamylating agent (e.g., 1,1'-acyloxyalkylcarbonochloridate, para-nitrophenyl carbonate, or the like).

Protected derivatives of the compounds of Formula I can be made by means known to those of ordinary skill in the art. A detailed description of the techniques applicable to the creation of protective groups and their removal can be found in T. W. Greene, *Protective Groups in Organic Synthesis*, John Wiley & Sons, Inc. 1981.

Compounds of Formula I can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diasteromeric derivatives of compounds of Formula I, dissociable complexes are preferred (e.g., crystalline diastereoisomeric salts). Diastereomers have distinct physical properties (e.g., melting points, boiling points, solubilities, reactivity, and the like) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, Honh Wiley & Sons, Inc. (1981).

In summary, an aspect of this invention is a process for preparing a compound of Formula I, which process comprises:

(A) reacting a compound of Formula 2:

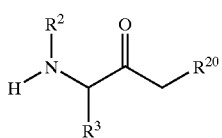

2 with a compound of the formula $LX^1R^{21}$, in which L is a leaving group, $R^{20}$ is $-NO_2$ or $-OR^{22}$, wherein $R^{22}$ is a hydroxy protecting group or optionally substituted $(C_{1-6})$alkyl, $(C_{6-12})$aryl$(C_{0-6})$alkyl, heteropolycyclo$(C_{8-12})$aryl$(C_{0-6})$alkyl, $(C_{1-6})$alkylcarbonyl or $(C_{6-12})$arylcarbonyl, $R^{21}$ is $R^1$ or a protecting group and each $X^1$, $R^1$, $R^2$ and $R^3$ are as defined in the Summary of the Invention for Formula I, and then removing one or more protective groups if necessary to provide a compound of Formula I in which $R^4$ is nitromethyl or $-CH_2OR^{17}$;

(B) reacting a compound of Formula 3:

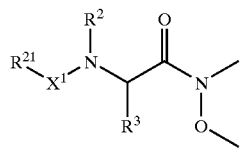

3 with a compound of the formula $LCH_2OR^{22}$, in which L is a leaving group, $R^{22}$ is a hydroxy protecting group or optionally substituted $(C_{1-6})$alkyl, $(C_{6-12})$aryl$(C_{0-6})$alkyl, heteropolycyclo$(C_{8-12})$aryl$(C_{0-6})$alkyl, $(C_{1-6})$alkylcarbonyl or $(C_{6-12})$arylcarbonyl, $R^{20}$ is $R^1$ or a protecting group and each $X^1$, $R^1$, $R^2$, $R^3$ and $R^{17}$ are as defined in the Summary of the Invention for Formula I, and then removing one or more protective groups if necessary to provide a compound of Formula I in which $R^4$ is $-CH_2OR^{17}$;

(C) oxidizing a compound of Formula 4:

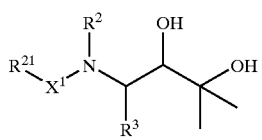

4 in which $R^{21}$ is $R^1$ or a protecting group and each $X^1$, $R^1$, $R^2$ and $R^3$ are as defined in the Summary of the Invention for Formula I, and then deprotecting if necessary to provide a compound of Formula I in which $R^4$ is 1-hydroxy-1-methylethyl;

(D) reacting a compound of Formula 5:

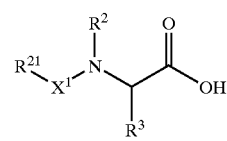

5 with nitromethane, in which $R^{21}$ is $R^1$ or a protecting group and each $X^1$, $R^1$, $R^2$ and $R^3$ are as defined in the Summary of the Invention for Formula I, and then deprotecting if necessary to provide a compound of Formula I in which $R^4$ is nitromethyl;

(E) optionally dealkylating a compound of Formula I in which $R^4$ is $-CH_2OR^{18}$, wherein $R^{18}$ is $(C_{1-6})$alkyl or $(C_{6-12})$aryl$(C_{1-6})$alkyl to provide a compound of Formula I in which $R^{18}$ is hydrogen;

(F) optionally converting a compound of Formula I into a pharmaceutically acceptable salt;

(G) optionally converting a salt form of a compound of Formula I to non-salt form;

(H) optionally converting an unoxidized form of a compound of Formula I into a pharmaceutically acceptable N-oxide;

(I) optionally converting an N-oxide form of a compound of Formula I its unoxidized form;

(K) optionally converting a non-derivatized compound of Formula I into a pharmaceutically prodrug derivative; and (L) optionally converting a prodrug derivative of a compound of Formula I to its non-derivatized form.

Processes for Making the Intermediates used in Making Compounds of Formula I:

Compounds of Formula 2 in which $R^{20}$ is $-OR^{22}$ can be prepared by condensing an α-aminoketone of Formula 6:

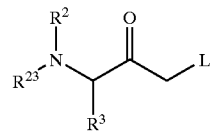

6 in which L is a leaving group and $R^{23}$ is an amino protective group, with a compound of the formula $HOR^{22}$ and then selectively removing the amino protective group. The condensation reaction is carried out in the presence of potassium fluoride and a suitable solvent (N,N-dimethylformamide (DMF), or the like) at 20 to 30° C., preferably at about −25° C., and requires 1 to 3 hours to complete. The α-aminoketone of Formula 3 is prepared from a corresponding α-amino-α'-diazoketone derivative. For example, a compound of Formula 3 in which L is bromo is prepared by treating a corresponding α-amino-α'-diazoketone derivative with hydrogen bromide in a suitable solvent (e.g., ether, or the like) at −20 to 0° C., typically at about −10° C., and requires approximately 30 minutes to 1 hour to complete. The α-amino-α'-diazoketone derivative is prepared by treating a corresponding α-aminocarboxylic acid with diazomethane in the presence of a suitable condensing agent (e.g., isobutyl chloroformate, or the like) and base (e.g., 4-methylmorpholine, triethylamine, or the like) and in a suitable solvent (e.g., tetrahydrofuran (THF), or the like) at −10 to 0° C., preferably at about −10° C., and requires approximately 30 minutes to complete. Deprotection is conveniently effected by treating the protected intermediate with acid (e.g., p-toluenesulfonic acid) to provide the compound of Formula 2 in an acid addition salt form.

Compounds of Formula 2 in which $R^{20}$ is —$OR^{22}$ can be prepared by condensing a α-amino-N-methoxy-N-methylcarboxamide of Formula 7:

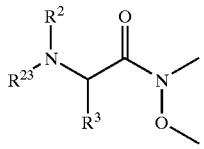

7 in which $R^{23}$ is an amino protective group, with a compound of the formula $LCH_2OR^{22}$ and then selectively removing the amino protective group. Typically the reaction is carried out under nitrogen in a suitable solvent (e.g., THF) at −60 to 25° C. and requires 10 to 20 hours to complete. Compounds of Formula 7 are prepared by reacting a corresponding α-aminocarboxylic acid with N,O-dimethylhydroxylamine hydrochloride.

Compounds of Formula 2 in which $R^{20}$ is —$NO_2$ can be prepared by reacting a α-aminocarboxylic acid of Formula 8:

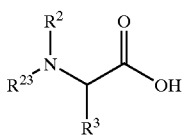

8 in which $R^{23}$ is an amino protective group, with nitromethane and then selectively removing the amino protecting group. Typically the reaction with the nitromethane is carried out under nitrogen in the presence of a coupling agent (e.g., 1,1'-carbonyldiimidazole, or the like) and in a suitable solvent (e.g., TBF) at −10 to 25° C. and requires 10 to 20 hours to complete. Detailed descriptions for the preparation of compounds of Formula 2 are found in References 1, 2 and 3, supra.

Compounds of Formula 3 are prepared by reacting a corresponding carboxylic acid with N,O-dimethylhydroxylamine hydrochloride. Compounds of Formula 4 can be prepared by oxidizing a corresponding N-(3-methylbut-2-enyl) derivative. Typically the oxidation of the N-(3-methylbut-2-enyl) derivative is carried out with a suitable oxidizing agent (e.g., osmium tetroxide, or the like) in a suitable solvent (e.g., acetonitrile, or the like) at approximately 0° C. and requires 10 to 20 hours to complete. The N-(3-methylbut-2-enyl) derivative is prepared from a corresponding N-(2-oxoethyl) derivative via a Wittig reaction.

Process for Making Compounds of Formula II:

A process for preparing a compound of Formula II:

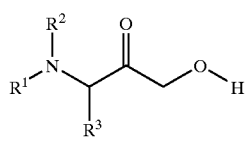

II which process comprises hydrogenating a compound of Formula 9:

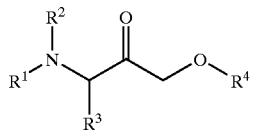

9 in which $R^1$ is peptidyl, $R^2$ is hydrogen or $(C_{1-6})$alkyl, $R^3$ is an amino acid side chain and $R^4$ is $(C_{1-6})$alkyl or $(C_{6-12})$aryl$(C_{1-6})$alkyl, in the presence of a catalytic amount of 20% palladium hydroxide on carbon. The hydrogenation can be effected with hydrogen gas or an effective amount of cyclohexene. The hydrogenation may be carried out in cyclohexene alone or along with a suitable solvent (e.g., ethanol, or the like) at 80 to 90° C. and requires 1 to 2 hours to complete. Preferably, the process is carried out in an excess amount of cyclohexene, typically 100 times the molar amount of the compound of Formula II, in a 1:2 mixture of cyclohexene:ethanol. The process is particularly useful in preparing the individual (R)- or (S)-isomers of the compounds of Formula II. Thus, by proceeding as set forth above, the individual isomers of the compounds of Formula I in which $R^4$ is hydroxymethyl can be prepared by dealkylating a compound of Formula I in which $R^1$ is —$CH_2OR^{18}$, wherein $R^{18}$ is $(C_{1-6})$alkyl or $(C_{6-12})$aryl$(C_{1-6})$alkyl. A detailed description of this process is found in Example 5, infra.

EXAMPLES

Reference 1

(S)-3-Amino-2-oxo-5-phenylpentyl 2,5-Dichlorobenzoate Toluenesulfonic Acid Salt (a) A solution comprised of (S)-2-tert-butoxycarbonylamino-4-phenylbutyric acid (7.82 g, 28 mmol) in TBF (35 mL) was cooled to −10° C. and 4-methylmorpholine (3.08 mL, 28 mmol) and isobutyl chloroformate (3.63 mL, 28 mmol) were added. The mixture was stirred for 5 minutes and filtered. The solids were washed with THF (15 mL) and the combined filtrates were transferred to the receiving flask of a Diazald© kit (Aldrich). Diazomethane, prepared by ethanolic potassium hydroxide cleavage of an ethereal solution of Diazald© (10 g, 46 mmol/100 mL diethyl ether), was distilled into the mixed anhydride over 30 minutes and then acetic acid was added to quench the reaction. Ethyl acetate (100 mL) was added and the mixture was washed with saturated aqueous sodium bicarbonate, dried ($MgSO_4$), filtered, and concentrated to provide tert-butyl(S)-3-diazo-2-oxo-1-phenethylpropylcarbamate (8.44 g, 27.7 mmol).

(b) A solution comprised of tert-butyl(S)-3-diazo-2-oxo-1-phenethylpropylcarbamate (7.09 g, 23.4 mmol) in ether (100 mL) was cooled to −10° C. and a solution comprised of hydrogen bromide/acetic acid (4.66 mL, 30% by weight) in ether (30 mL) was added dropwise. The mixture was stirred for 30 minutes and then ether (200 mL) was added. The mixture was washed with brine (50 mL), saturated aqueous sodium bicarbonate (150 mL), brine (50 mL), dried ($MgSO_4$), filtered, and concentrated. Product was crystallized from hexane, to provide tert-butyl (S)-3-bromo-2-oxo-1-phenethylpropylcarbamate (5.29 g, 14.7 mmol). $^1$H NMR ($CDCl_3$): δ 1.44 (9H, s, t-Bu), δ 1.86 (1H, m, one $CH_2CH_2C_6H_5$), δ 2.18 (1H, m, other $CH_2CH_2C_6H_5$), δ 2.67 (2H, t, J=7.7 Hz, $CH_2CH_2C_6H_5$), δ 3.99 (2H, 2×d, J=13 Hz, $CH_2Br$), δ 4.53 (1H, m, CHNH), δ 5.08 (1H, br.D, 5 Hz, NH), δ 7.17–7.29 (5H, m, aromatic H).

(c) Potassium fluoride (0.326 g, 5.61 mmol) was added to a mixture of the tert-butyl (S)-3-bromo-2-oxo-1-phenethylpropylcarbamate (1.00 g, 2.81 mmol) and 2,5-dichlorobenzoic acid (1.07 g, 5.61 mmol) in DMF (10 mL). The mixture was stirred for 2 hours at room temperature and then ethyl acetate (75 mL) was added. The solution was washed with 1M hydrochloric acid (20 mL), saturated aqueous sodium bicarbonate (20 mL), dried (MgSO$_4$), filtered, and evaporated to dryness to provide crude (S)-3-tert-butoxycarbonylamino-2-oxo-5-phenylpentyl 2,5-dichlorobenzoate.

(d) The crude (S)-3-tert-butoxycarbonylamino-2-oxo-5-phenylpentyl 2,5-dichlorobenzoate was dissolved in ether (5 mL) and a solution of azeotropically dried p-toluenesulfonic acid (1.31 g, 7.7 mmol) in ether (5 mL) was added. The mixture was stirred at room temperature for approximately 12 hours and then ether (200 mL) was added to provide a solid material. The solid material was broken up, filtered, washed with ether (2×50 mL) and dried in vacuo to provide (S)-3-amino-2-oxo-5-phenylpentyl 2,5-dichlorobenzoate toluenesulfonic acid salt (1.24 g, 2.3 mmol).

Reference 2

3-Amino-1-benzyloxy-5-phenylpentan-2-one p-Toluenesulfonic Acid Salt (a) Magnesium turnings (7.3 g, 300.29 mmol), previously dried in an oven at 100° C. for approximately 12 hours, and mercuric chloride (1.2 g, 4.42 mmol) were weighed into a dry flask. The flask was purged with nitrogen for 10–15 minutes and then anhydrous THF (200 mL) was added under nitrogen. The mixture was cooled to −40° C. and stirred while chloromethoxymethylbenzene (42.9 g, 273.93 mmol) was added via syringe. The mixture was stirred under nitrogen for 6 hours while the temperature was allowed to warm to 3 to 5° C.

(b) The mixture was cooled to −60° C. and stirred under nitrogen while a solution comprised of tert-butyl 1-(N-methoxy-N-methylcarbamoyl)-3-phenylpropylcarbamate (17 g, 52.73 mmol) in anhydrous THF was added via syringe and the mixture was stirred until the reaction was complete. The reaction was quenched slowly with ammonium chloride solution and the mixture was stirred for 15–30 minutes. The mixture was extracted with ethyl acetate (3×7 mL) and the combined extract was dried (Mg$_2$SO$_4$), filtered and concentrated. Product was purified from the residue by flash column chromatography using silica gel 60 to provide tert-butyl 3-benzyloxy-2-oxo-1-phenethylpropylcarbamate (17.15 g, 44.72 mmol). $^1$H NMR (CDCl$_3$): δ 1.43 (s, 9H), δ 1.74–1.82 (m. 1H), δ 2.14–2.16 (m, 1H), δ 2.60–2.67 (m, 2H), δ 4.13–4.14 (d, 2H), δ 4.49–4.61 (m, 3H), δ 5.14–5.17 (d, 1H), δ 7.1–7.4(m, 10H).

(c) p-Toluenesulfonic acid hydrate (17.15 g, 90.16 mmol) was azeotroped with an isopropyl alcohol/toluene mixture (1:1) to provide anhydrous p-toluene sulfonic acid. The as sulfonic acid was dried under high vacuum and dissolved in a minimum of anhydrous ether. The solution of sulfonic acid was added to a solution of tert-butyl 3-benzyloxy-2-oxo-1-phenethylpropylcarbamate (17.15 g, 44.72 mmol) in a minimum of anhydrous ether under nitrogen to provide a precipitate. The mixture was stirred under nitrogen until the reaction was complete and then filtered. The precipitate was dried under vacuum to provide 3-amino-1-benzyloxy-5-phenylpentan-2-one p-toluenesulfonic acid salt (17.78 g, 38.9 mmol). $^1$H NMR (DMSO-d$_6$): δ 1.84–2.01 (m, 1H), δ 2.12–2.22 (m, 1H), δ 2.28 (s, 3H), δ 2.59–2.70 (m, 2H), δ 4.24–4.35 (m, 1H), δ 4.4 (d, 2H), δ 4.5–4.6 (m, 2H), δ 7.09–7.50 (m, 14H), δ 8.15–8.35 (s, 3H).

Proceeding as in Reference 2(a)–(b) or 2(a)–(c), provided the following compounds:

tert-butyl 1-benzyloxyacetylpentylcarbamate; $^1$H NMR (CDCl$_3$): δ 0.82–0.87 (m, 3H), δ 1.21–1.20 (m, 3H), δ 1.41 (s, 9H), δ 1.7–1.9 (m, 1H), δ 1.41 (d, 2H), δ 4.5–4.7 (m, 3H), δ 5.06–5.09 (d, 1H), δ 7.3–7.4 (m, 5H);

tert-butyl 3-benzyloxy-2-oxopropylcarbamate; $^1$H NMR (CDCl$_3$): δ 1.42 (s, 9H), δ 4.08–4.15 (m, 2H), δ 4.17–4.22 (d, 2H), δ 4.57 (s, 2H), δ 5.19 (m, 1H), δ 7.24–7.40 (m, 5H); and 3-amino-1-benzyloxyheptan-2-one p-toluenesulfonic acid salt; $^1$H NMR (DMSO-d$_6$): δ 0.8–0.9 (m, 3H), δ 1.15–1.40 (m, 4H), δ 1.6–1.72 (m, 1H), δ 1.72–1.9 (m, 1H), δ 2.28 (s, 3H), δ 4.15–4.3 (m, 1H), δ 4.35–4.45 (d, 2H), δ 4.5–4.6 (m, 2H), δ 7.09–7.12 (d, 2H), δ 7.25–7.5 (m, 7H), δ 8.0–8.2 (s, 3H);

1-amino-3-benzyloxypropan-2-one p-toluenesulfonic acid salt; $^1$H NMR (DMSO-d$_6$): δ 2.28 (s, 3H), δ 3.9–4.1 (m, 2H), δ 4.3 (s,2H), δ 4.55 (s, 2H), δ 7.05–7.15 (d, 2H), δ 7.25–7.50 (m, 7H), δ 7.9–8.15 (s, 3H);

3-amino-1-benzyloxy-5-(4-hydroxyphenyl)pentan-2-one p-toluenesulfonic acid salt; $^1$H NMR (DMSO-d$_6$): δ 1.80–1.95 (m, 1H), δ 2.0–2.2 (m, 1H), δ 2.28 (s, 3H), δ 4.2–4.3 (m, 1H), δ 4.37 (d, 2H), δ 4.48–4.58 (m, 2H), δ 6.66–6.69 (d, 2H), δ 6.95–6.98 (d, 2H), δ 7.09–7.12 (d, 2H), δ 7.28–7.41 (m, 4H), δ 7.45–7.48 (d, 2H), δ 8.1–8.3 (m, 3H);

2-amino-N-(3-benzyloxy-2-oxo-1-phenethylpropyl)-3-methylpentanamide p-toluenesulfonic acid salt; $^1$H NMR (CDCl$_3$): δ 0.87–0.95 (d, 6H), δ 1.16 (m, 1H), δ 1.48 (m, 1H), δ 1.79–1.84 (m, 1H), δ 2.08 (m, 1H), δ 2.28 (s, 3H), δ 2.56–2.60 (m, 2H), δ 3.75 (t, 1H), δ 4.29 (d, 1H), δ 4.33 (d, 1H), δ 4.50–4.54 (m, 3H), δ 7.12–7.33 (m, 12H), δ 7.48 (s, 2H), δ 8.10 (s, 3H), δ 8.78 (d, 1H); and 2-amino-N-(1-benzyloxyacetylpentyl)-3-methylpentanamide p-toluenesulfonic acid salt; $^1$H NMR (CDCl$_3$): δ 0.82–0.89 (m, 9H), δ 0.92–1.47 (m, 7H), δ 1.77–1.78 (m, 2H), δ 2.28 (s, 3H), δ 3.49 (s, 1H), δ 3.70 (t, 1H), δ 4.29 (d, 1H), δ 4.33 (d, 11H), δ 4.51–4.52 (m, 2H), δ 7.10–7.13 (d, 2H), δ 7.34–7.38 (m, 5H), δ 7.49 (d, 2H), δ 8.07 (s, 3H), δ 8.65 ppm (d, 1H).

Reference 3

(S)-3-Amino-1-nitro-5-phenylpentan-2-one p-Toluenesulfonic Acid Salt (a) A suspension comprised of sodium hydride (5.6 g of 60% dispersion in mineral oil, washed twice with hexane, 140 mmol) in THF (50 mL) was cooled under nitrogen to 0° C. and a solution comprised of nitromethane (10 mL, 180 mmol) in THF (50 mL) was added dropwise. The mixture was stirred at 0 to 20° C. for 2 hours and then cooled to −10° C. A solution comprised of (S)-2-tert-butoxycarbonylamino-4-phenylbutyric acid (12.5 g, 45 mmol) in THF (50 mL) was cooled to 0° C. and then 1,1'-carbonyldiimidazole (7.5 g, 46 mmol) was added. The butyric acid mixture was stirred for 30 minutes, while allowing it to warm to room temperature, and then added dropwise to the nitromethane mixture. The combined mixture was allowed to warm to room temperature and stirred under nitrogen for 14 hours. The reaction was quenched with a small amount of water added slowly and then the mixture was diluted with 1M aqueous hydrochloric acid (200 mL) and ethyl acetate (500 mL). The organic layer was separated, washed with saturated aqueous sodium chloride (2×250 mL), dried over anhydrous magnesium sulfate, filtered and concentrated in vacuo to provide a yellow solid (14 g). The residue was recrystallized from ethyl acetate-hexane to provide tert-butyl (S)-3-nitro-2-oxo-1-phenethylpropylcarbamate (9.2 g, 28.4 mmol) as a pale yellow solid. $^1$H NMR (270 MHz, CDCl$_3$): δ 1.44 (s, 9H), δ 1.85–1.98 (m, 1H), δ 2.15–2.25 (m, 1H), δ 2.61–2.74 (m, 2H), δ 4.16–4.23 (m, 1H), δ 4.94 (d, J=4.9 Hz, 1 NH), δ 5.30 (d, J=15.1 Hz, 1H), δ 5.44 (d, J=15.1 Hz, 1H), δ 7.15–7.32 (m, 5H); $^{13}$C NMR (CDCl$_3$): δ 28.29, 31.61, 31.89, 58.09, 81.33, 126.69, 128.45, 128.85, 139.86, 155.6, 196.24.

(b) A solution comprised of anhydrous p-toluenesulfonic acid (26 mmol) in ethyl ether (10 mL) was added to a suspension comprised of tert-butyl (S)-3-nitro-2-oxo-1-phenethylpropylcarbamate (4.5 g, 14 mmol) in dichloromethane (20 mL) and ethyl ether (150 mL). The mixture was stirred for 70 hours at room temperature and the filtered. The solid collected was washed thoroughly with ethyl ether and dried in vacuo to provide (S)-3-amino-1-nitro-5-phenylpentan-2-one p-toluenesulfonic acid salt (5.4 g, 13.7 mmol) as a white solid. $^1$H NMR (270 MHz, DMSO-d$_6$): δ 1.92–2.05 (m, 1H), δ 2.15–2.28 (m, 1H), δ 2.29 (s, 3H), δ 2.56–2.76 (m, 2H), δ 4.44 (br.s, 1H), δ 6.97 (d, J=16.1 Hz, 1H), δ 6.29 (d J=16.1 Hz, 1H), δ 7.12 (d, J=8.4 Hz, 2H), δ 7.20–7.35 (m, 5H), δ 7.49 (d, J=8.2 Hz, 1H), δ 8.46 (br.s, 3 NH).

Example 1

Benzyl 1S-(3-Hydroxy-2-oxo-1S-phenethylpropylcarbamoyl)-3-methylbutylcarbamate (Compound 1)

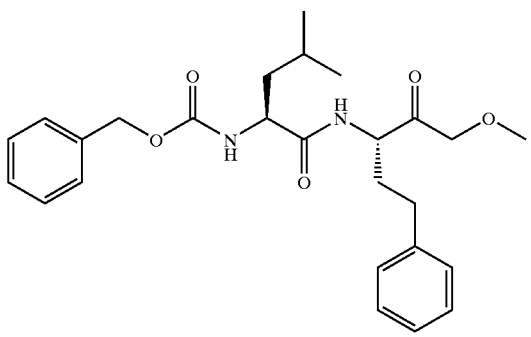

A mixture comprised of magnesium turnings (235 mg, 9.58 mmol) and mercuric chloride (3 5 mg, 0. 13 mmol) in dry THF under nitrogen was cooled to between –10 and 20° C. and chloromethoxymethane (0.75 mL, 9.58mmol) was added. The mixture was stirred for 6 hours while the temperature was allowed to warm to between –8 and 0° C. The mixture was then cooled to 780 C and stirred while a solution comprised of benzyl 1-[1-(N-methoxy-N-methylcarbamoyl)-3-phenethylpropylcarbamoyl]-3-methylbutylcarbamate (500 mg, 1.08 mmol) in anhydrous TBF (6 mL) was added. The mixture was allowed to warm slowly over approximately 12 hours and then the reaction was quenched with ammonium chloride solution and then extracted with ethyl acetate. The ethyl acetate was dried (MgSO$_4$), filtered and concentrated. Product was purified from the residue by flash column chromatography eluting with 33:1 ethyl acetate/hexanes to provide benzyl 1S-(3-hydroxy-2-oxo-1S-phenethylpropylcarbamoyl)-3-methylbutylcarbamate (374.8 mg, 0.824 mmol); $^1$H NMR (CDCl$_3$): δ 0.91–93 ppm (d, 6H), δ 1.55 ppm (s, 3H), δ 1.55–1.63 ppm (m, 1H), δ 1.8–1.95 ppm (m, 1H), δ 2.2–2.3 ppm (m, 1H), δ 2.57–2.63 ppm (t, 2H), δ 3.37 ppm (s, 3H), δ 4.06–4.15 ppm (m, 2H), δ 4.78–4.84 ppm (m, 1H), δ 5.1 ppm (s, 2H), δ 6.49–6.52 ppm (d, 1H), δ 7.12–7.31 ppm (m, 10H); LC/MS (455 M+H$^+$);

Proceeding as in Example 1 provided the following compounds of Formula I:

N-{1-[3-benzyloxy-2-oxo-1-(2-phenylcarbamoylethyl) propylcarbamoyl]-2-methylbutyl}naphthalene-2-carboxamide (Compound 2);

benzyl 3S-acetylamino-N-(3-benzyloxy-2-oxo-1-phenethylpropyl)succinamate (Compound 3);

2S-acetylamino-N$^1$-(3-benzyloxy-2-oxo-1-phenethylpropyl)-N$^4$-phenylsuccinamide (Compound 4);

tert-butyl 1-(3-benzyloxy-2-oxo-1-phenethylpropylcarbamoyl)-3-phenylpropylcarbamate (Compound 5); and 4-benzyloxy-N-(3-benzyloxy-2-oxo-1-phenethylpropyl) benzamide (Compound 6).

Example 2

3S-(2S-Benzyloxycarbonylamino-4-methylpentanoylamino)-2-oxo-5-phenylpentyl 2,5-Dichlorobenzoate (Compound 7)

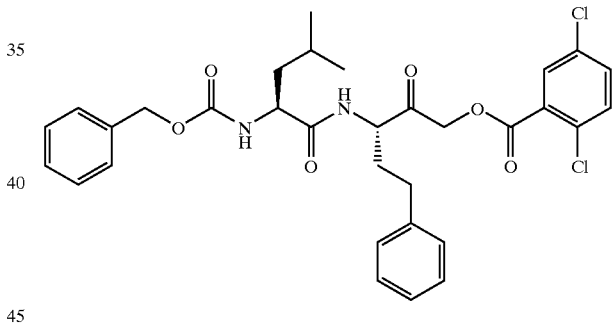

A solution comprised of (S)-2-benzyloxycarbonylamino-4-methylpentanoic acid (0.20 g, 0.76 mmol) in THF (5 mL) was cooled to –10° C. and then 4-methylmorpholine (84 μL, 0.76 mmol) and isobutyl chloroformate (99 μL, 0.76 mmol) were added. The mixture was stirred for 5 minutes and then (S)-3-amino-2-oxo-5-phenylpentyl 2,5-dichlorobenzoate toluenesulfonic acid salt (0.41 g, 0.76 mmol) and 4-methylmorpholine (84 μL, 0.76 mmol) were added sequentially. The mixture was stirred for 45 minutes and then ethyl acetate (30 mL) was added. The mixture was washed with 1M hydrochloric acid (5 mL), saturated aqueous sodium bicarbonate (5 mL) and brine (5 mL), dried (MgSO$_4$), filtered and concentrated. The residue was crystallized from CH$_2$Cl$_2$/ether to provide 3S-(2S-benzyloxycarbonylamino-4-methylpentanoylamino)-2-oxo-5-phenylpentyl 2,5-dichlorobenzoate (0.32 g, 0.52 mmol). $^1$H NMR (CDCl$_3$): δ 0.92 (6H, 2×d*, 2×CH$_3$, δ 1.46–1.78 (3H, m*, CH$_2$CH(CH$_3$)$_2$, δ 1.96 (1H, m, one CH$_2$CH$_2$C$_6$H$_5$, δ 2.55 (1H, m, other CH$_2$CH$_2$C$_6$H$_5$, δ 2.65 (2H, t, J=7.7 Hz, CH$_2$CH$_2$C$_6$H$_5$, δ 4.18 (1H, m, CHNH (Leu), δ 4.65 (1H, m, CHCH$_2$CH$_2$C$_6$H$_5$, δ 4.99 (2H, 2×d*, CH$_2$OOCC$_6$H$_3$Cl$_2$, δ

5.06 (2H, s*, C$_6$H$_5$CH$_2$O, δ 5.08 (1H, m*, CHNH(CBZ), δ 6.7 (1H, br., CHNH (amide), δ 7.14–7.48 (12H, m*, aromatic, δ 7.92 (1H, s, 6-CH (C$_6$H$_3$Cl$_2$).

Proceeding as in Example 5 provided the following compounds of Formula I:

tert-butyl 1S-(3-benzyloxy-2-oxo-1S-phenethylpropylcarbamoyl)-3-methylbutylcarbamate (Compound 8); $^1$H NMR (CDCl$_3$): δ 0.91–0.93 (d, 6H), δ 1.21–1.24 (t, 1H), δ 1.42–1.53 (m, 1H), δ 1.60–1.68 (m, 1H), δ 1.78–1.93 (m, 1H), δ 2.13–2.30 (m, 1H), δ 2.54–2.62 (m, 2H), δ 4.09–4.14 (m, 2H), δ 4.48–4.60 (q, 2H), δ 5.09 (s, 1H) δ 6.52–6.55 (d, 1H), δ 7.07–7.37 (m, 15H);

N-[1S-(3-benzyloxy-2-oxo-1S-phenethylpropylcarbamoyl)-3-methylbutyl] pyrrolidine-2-carboxamide (Compound 9); $^1$H NMR (CD$_3$OD): δ 0.88–1.0 (m, 6H), δ 1.15–1.19 (t, 1H), δ 2.5–2.8 (m, 4H), δ 1.9–2.25 (m, 4H), δ 2.40–2.80 (m, 3H), δ 3.45–3.70 (m, 1H), δ 4.20–4.40 (m, 2H), δ 4.50–4.70 (m, 2H), δ 7.16–7.40 (m, 10H); M+H$^+$ (494.4);

N-(3-benzyloxy-2-oxo-1S-phenethylpropyl)-2S-(2-1H-indol-3-ylacetylamino)-3-methylpentanamide (Compound 10); $^1$H NMR (CDCl$_3$): δ 0.93 (m, 6H), δ 1.21 (m, 1H), δ 1.66 (m, 1H), δ 2.01 (m, 1H), δ 2.54 (m, 3H), δ 4.06 (q, J=14 Hz, 7.2 Hz, 2H), δ 4.23 (m, 1H), δ 4.45 (m, 2H), δ 4.58 (m, 1H), δ 6.29 (d, J=8.8 Hz, 1H), δ 7.13 (m, 14H), 6 7.61 (m, 1H), δ 9.24 (br.s. 1H). LC-MS: 554.3 (M+H$^+$, 100%);

tert-Butyl 1S-(3-benzyloxy-2-oxo-1S-phenethylpropylcarbamoyl)-2-methylbutylcarbamate (Compound 11), $^1$H NMR (CDCl$_3$): δ 0.87–0.92 (m, 6H), δ 1.02–1.22 (m, 1H), δ 1.4–1.5 (s,m, 10H), δ 1.75–1.95 (m, 2H), δ 2.15–2.30 (m, 1H), δ 2.5–2.7 (m, 2H), δ 2.89–3.95 (t, 1H), δ 4.12 (s, 2H), δ 4.48–4.62 (q, 2H), δ 4.85–5.0 (m, 2H), δ 6.49–6.52 (d, 1H), δ 7.07–7.4 (m, 10H); M+H$^+$ (497.2);

N-(3-benzyloxy-2-oxo-1S-phenethylpropyl)-2S-(3,3-diphenylpropionylamino)-3-methylpentanamide (Compound 12); $^1$H NMR (CDCl$_3$): δ 0.72 (m, 6H), δ 1.12 (m, 1H), δ 1.45–1.56 (m, 4H), δ 1.77–1.86 (m, 1H), δ 2.12 (m, 1H), δ 2.49–2.56 (m, 2H), δ 2.93 (t, J=7.1 Hz, 2H), δ 4.09 (s, 2H), δ 4.12–4.18 (m, 1H), δ 4.51–4.56 (m, 3H), δ 4.80 (m, 1H), δ 5.85 (br.d., 1H), 66.24 (d, J=8.6 Hz), δ 7.08–7.40 (m, 20H). LC-MS: 605.3 (M+H$^+$, 100%);

N-[1S-(3-benzyloxy-2-oxo-1S-phenethylpropylcarbamoyl)-2-methylbutyl] naphthalene-2-carboxamide (Compound 13); LC-MS: 551.3 (M+H$^+$, 100%);

N-(3-benzyloxy-2-oxo-1S-phenethylpropyl)-2S-[3-(3-methoxyphenyl)ureido]-3-methylpentanamide (Compound 14); $^1$H NMR (CDCl$_3$): δ 0.88 (m, 6H), δ 1.04 (m, 1H), δ 1.50 (m, 1H), δ 1.74–1.83 (m, 2H), δ 2.04 (m, 1H), δ 2.41–2.60 (m, 2H), δ 3.59 (s, 3H), δ 4.19–4.32 (m, 4H), δ 4.53 (s, 2H), δ 6.48 (d, J=7.6 Hz, 1H), δ 6.84 (d, J=7.1 Hz, 1H), δ 7.19–7.51 (m, 14H). LC-MS: 546.3 (M+H$^+$, 100%);

N-(3-benzyloxy-2-oxo-1S-phenethylpropyl)-3-methyl-2S-[2-(3-nitrophenyl)acetylamino]pentanamide (Compound 15); $^1$H NMR (CDCl$_3$): δ 0.87 (m, 1H), δ 1.12 (m, 1H), δ 1.45–1.83 (m, 5H), δ 2.20 (m, 1H), δ 2.56 (m, 2H), δ 3.65 (m, 2H), δ 4.23 (m, 2H), δ 4.27 (t, J=8.3 Hz), δ 4.55 (q, J=14 Hz, 8.6 Hz), δ 4.89 (m, 1H), δ 6.22 (d, J=8.7 Hz, 1H), δ 6.33 (d, J=7.6 Hz, 1H), δ 7.05 (m, 1H), δ 7.19–7.41 (m, 10H), δ 7.62 (d, J=8.3 Hz, 1H), δ 8.07–8.15 (m, 2H). LC-MS: 560.3 (M+H$^+$, 100%);

N-(3-benzyloxy-2-oxo-1S-phenethylpropyl)-3-methyl-2S-(2-naphthalen-1-ylacetylamino)pentanamide (Compound 16); $^1$H NMR (CDCl$_3$): δ 0.99 (m, 6H), δ 1.06 (m, 1H), δ 1.55–1.65 (m, 2H), δ 1.72–2.02 (m, 2H), δ 2.22–2.30 (m, 1H), δ 2.60–2.72 (m, 1H), δ 4.08 (s, 2H), δ 4.49–4.65 (m, 3H), δ 4.93–5.01 (m, 1H), δ 6.53 (d, J=7.2 Hz, 1H), δ 6.64 (s, 1H), δ 7.08–7.61 (m, 13H), δ 7.72 (d, J=8.5 Hz, 1H), δ 7.80–8.01 (m, 2H), δ 8.29–8.32 (m, 1H). LC-MS: 551.1 (M+H$^+$, 100%);

N-(3-benzyloxy-2-oxo-1S-phenethylpropyl)-3-methyl-2S-(2-pyridin-4-ylacetylamino)pentanamide (Compound 17); $^1$H NMR (DMSO-d$_6$, mixture of diastereomers): δ 0.79 (m, 7H), (m, 1H), δ 1.42 (m, 1H), δ 1.73–1.78 (m, 2H), δ 2.11 (m, 1H), δ 2.40–2.53 (m, 3H), δ 3.44 (m, 2H), δ 4.03–4.10 (m, 2H), δ 4.34–4.51 (m, 3H), δ 4.79 (m, 1H), δ 6.79 (d, 1H), δ 7.00–7.29 (m, 13H), δ 8.48, 8.49 (d, 1H). LC-MS: M+1 (516.2);

tert-butyl 4-[1S-(3-benzyloxy-2-oxo-1S-phenethylpropylcarbamoyl)-3-methylbutylcarbamoyl] benzyl}carbamate (Compound 18); $^1$H NMR (DMSO-d$_6$): δ 0.95 (d, J=6 Hz, 6H), δ 1.42 (s, 9H), δ 1.53–1.86 (m, 4H), δ 2.21 (m, 1H), δ 2.57 (t, J=8.2 Hz, 2H), δ 4.13 (s, 2H), δ 4.35 (s, 2H), δ 4.53–4.68 (m, 3H), δ 4.84–4.92 (m, 1H), δ 6.47 (d, J=6.9 Hz; 1H), δ 6.68 (d, J=7.1 Hz, 1H), δ 7.16 (d, J=8.1 Hz, 1H), δ 7.16–7.40 (m, 11H), δ 7.71 (d, J=9.0 Hz, 2H). LC-MS: 630.2 (M+H$^+$, 100%);

4-aminomethyl-N-[1S-(3-benzyloxy-2-oxo-1S-phenethylpropylcarbamoyl)-3-methylbutyl]benzamide hydrochloride (Compound 19);

N-(3-benzyloxy-2-oxo-1S-phenethylpropyl)-3-methyl-2S-(2-pyridin-3-ylacetylamino)pentanamide (Compound 20); $^1$H NMR (DMSO-d$_6$,): δ 0.81–0.90 (m, 6H), δ 1.05 (m, 1H), δ 1.43 (m, 1H), δ 1.76–1.82 (m, 2H), δ 2.02 (m, 1H), δ 2.49–2.52 (m, 2H), δ 3.53 (s, 2H), δ 4.07–4.10 (m, 2H), δ 4.12–4.53 (m, 3H), δ 4.82 (m, 1H), δ 6.45 (t, 1H), δ 6.71 (d, 1H), δ 7.19–7.31 (m, 11H), 67.60 (d, 1H), δ 8.49 (m, 2H). LC-MS:M+1 (516.2);

2S-amino-N-(3-benzyloxy-2-oxo-1S-phenethylpropyl)-4-phenylbutyramide hydrochloride (Compound 21); $^1$H NMR (CDCl$_3$): δ 1.81–1.92 (m, 2H), δ 2.13–1.21 (m, 2H), δ 2.51–2.72 (m, 4H), δ 4.11 (s, 2H), δ 4.15–4.22 (m, 1H), δ 4.55 (q, J=14 Hz, 7.2 Hz, 2H), δ 4.86–4.92 (m, 2H), δ 6.69 (br.s; 1H), δ 7.02–7.40 (m, 15H). LC-MS: 445.3 (M+H$^+$, 100%);

N-[1S-(3-benzyloxy-2-oxo-1S-phenethylpropylcarbamoyl)-2-methylbutyl] nicotinamide (Compound 22); $^1$H NMR (DMSO-d$_6$): δ 0.93–0.97 (m, 6H), δ 1.23 (m, 1H), δ 1.57–1.63 (m, 2H), δ 1.85–1.93 (m, 1H), δ 2.25 (m, 1H), δ 2.56–2.61 (m, 2H), δ 3.84–3.85 (m, 2H), δ 4.51–4.57 (m, 3H), δ 4.91–4.94 (m, 1H), δ 6.52 (d, 1H), δ 7.18–7.36 (m, 12H), δ 8.09 (d, 1H), δ 8.72–8.73 (m, 1H), δ 9.03 (s, 1H). LC-MS: M+1 (502.3);

N-[1-(3-benzyloxy-2-oxo-1-phenethylpropylcarbamoyl)-2-methylbutyl]pyrazine-2-carboxamide (Compound 23); $^1$H NMR (DMSO-d$_6$): δ 0.90–0.98 (m, 6H), δ 1.22 (m, 1H0; 1.86–1.89 (m, 2H), δ 2.02 (m, 1H), δ 2.19 (m, 1H0; 2.53–2.61 (m, 2H), δ 4.13–4.21 (m, 2H), δ 4.55–4.56 (m, 3H), δ 4.90–4.92 (M, 1H), δ 6.52 (D, 1H), δ 7.17–7.32 (M, 10H), δ 8.29 (D, 1H), δ 8.55 (S, 1H), δ 8.75 (d, 1H), δ 9.37 (s, 1H). LC-MS: M+1 (503.3);

N-[1S-(3-benzyloxy-2-oxo-1S-phenethylpropylcarbamoyl)-2-methylbutyl]-3- cyanobenzamide (Compound 24); ¹H NMR (DMSO-d₆): δ 0.91–0.96 (m, 6H), δ 1.21 (m, 1H), δ 1.57 (m, 2H), δ 1.89 (m, 1H), δ 2.24 (m, 1H), δ 2.56–2.75 (m, 2H), δ 4.13 (s, 2H), δ 4.49–4.57 (m, 2H), δ 4.93–4.99 (m, 1H), δ 7.05 (d, 1H), δ 7.19–7.59 (m, 11H), δ 7.56–7.59 (d, 1H), δ 7.77–7.80 (m, 1H), δ 8.41 (m, 1H). LC-MS: M+1 (526.3);

N-{1S-[1-(3-benzyloxy-2-oxopropyl)pentylcarbamoyl]-2-methylbutyl}benzamide (Compound 25);

tert-butyl 4-[1S-(1S-benzyloxyacetylpentylcarbamoyl)-2-methylbutylcarbamoyl]benzylcarbamate (Compound 26); LC-MS: 582.3 (M+H⁺, 100%);

N-[1S-(3-benzyloxy-2-oxo-1S-phenethylpropylcarbamoyl)-2-methylbutyl] isophthalamide (Compound 27); ¹H NMR (CDCl₃): δ 0.80–1.05 (m, 6H), δ 1.20–1.35 (m, 1H), δ 1.6–1.7 (m, 1H), δ 1.80–1.95 (m, 1H), δ 2.00–2.30 (m, 2H), δ 2.52–2.60 (t, 2H), δ 4.08–4.25 (m, 2H), δ 4.48–4.65 (m, 2H), δ 4.80–4.90 (m, 1H), δ 6.50–6.60 (m, 1H), δ 6.80–6.90 (m, 1H), δ 7.0–7.4 (m, 9H), δ 7.48–7.51 (t, 1H), δ 7.87–7.90 (d, 1H), δ 8.04–8.20 (m, 2H), δ 8.59 (s, 1H), δ M+H⁺ (544.3);

N-[1S-(1S-benzyloxyacetylpentylcarbamoyl)-2-methylbutyl]isophthalamide (Compound 28); ¹H NMR (CDCl₃): δ 0.70–0.80 (m, 3H), δ 0.80–1.0 (m, 6H), δ 1.1–1.3 (m, 4H), δ 1.50–1.70 (m, 2H), δ 1.80–2.10 (m, 3H), δ 4.12–4.30 (q, 2H), δ 4.50–4.65 (m, 3H), δ 4.78–4.90 (m, 1H), δ 6.50–6.60 (m, 1H), δ 6.70–6.80 (m, 1H), δ 6.91–6.94 (d, 1H), δ 7.3–7.4 (m, 4H), δ 7.45–7.55 (t, 1H), δ 7.88–7.93 (t, 2H), δ 8.02–8.05 (d, 1H), δ 8.52 (s, 1H), δ M+H⁺ (496.2);

4-aminomethyl-N-[1S-(1S-benzyloxyacetylpentylcarbamoyl)-2-naphthalen-2-ylethyl]benzamide hydrochloride (Compound 29); ¹H NMR (DMSO-d₆): δ 0.76 (t, J=8.9 Hz, 3H), δ 1.06–1.27 (m, 4H), δ 1.54–1.77 (m, 2H), δ 3.23–3.41 (m, 2H), δ 4.04–4.19 (m, 4H), δ 4.75–4.82 (m, 2H), δ 7.21–7.86 (m, 13H), δ 8.49 (br.s, 4H), δ 8.72–8.85 (m, 2H). LC-MS: 566.2 (M+H⁺, 100%);

3-aminomethyl-N-[1S-(1S-benzyloxyacetylpentylcarbamoyl)-2-naphthalen-2-ylethyl]benzamide hydrochoride (Compound 30); ¹H NMR (DMSO-d₆): δ 0.83 (m, 3H), δ 1.10 (m, 1H), δ 1.26 (m, 3H), δ 1.54 (m, 1H), δ 1.75 (m, 1H), δ 3.26 (m, 2H), δ 4.03 (s, 2H), δ 4.36 (m, 2H), δ 4.36 (s, 2H), δ 4.90 (m, 1H), δ 7.45 (m, 4H), δ 7.83 (m, 5H), δ 8.21 (s, 2H), δ 8.61 (d, J=8.1 Hz, 1H), δ 8.74 (d, J=8.1 Hz, 1H). LC-MS: 476.2 (M+H⁺, 100%);

2S-(dibenzofur-2-ylsulfonylamino)-N-(3-benzyloxy-2-oxo-1S-phenethylpropyl)-3-methylpentanamide (Compound 31); ¹H NMR (CDCl₃): δ 0.79–0.88 (m, 6H), δ 1.0–1.14 (m, 1H), δ 1.51–1.71 (m, 1H), δ 1.68–1.80 (m, 1H), δ 2.0–2.20 (m, 1H), δ 2.35–2.50 (m, 2H), δ 3.59–3.65 (m, 2H), δ 3.76 (s, 1H), δ 4.26–4.40 (q, 2H), δ 4.44–4.47 (d, 1H), δ 4.52–4.60 (m, 1H), δ 5.20–5.23 (d, 1H), δ 6.49–6.51 (d, 1H), δ 6.79–6.81 (m, 1H), δ 6.95–6.98 (d, 2H), δ 7.10–7.18 (m, 2H), δ 7.20–7.45 (m, 4H), δ 7.50–7.65 (m, 4H), δ 7.90–8.0 (m, 3H), δ 8.44 (d, 1H), δ M+H⁺ (627.3);

N-[1S-(3-benzyloxy-2-oxo-1S-phenethylpropylcarbamoyl)-2-methylbutyl]-3-ureidobenzamide (Compound 32); ¹H NMR (DMSO-d₆): δ 0.93 (m, 1H), δ 1.12 (m, 1H), δ 1.50 (m, 1H), δ 1.81–2.2 (m, 5H), δ 2.51–2.58 (m, 2H), δ 4.25–4.61 (m, 6H), δ 5.89 (m, 1H), δ 7.15–7.62 (m, 10H), δ 7.71 (d, J=8.1 Hz, 1H), δ 7.80 (s, 1H), δ 8.28 (d, J=7.9 Hz, 1H), δ 8.51 (d, J=8.1 Hz, 1H), δ 8.67 (s, 2H). LC-MS: 559.2 (M+H⁺, 100%);

N-[1S-(3-benzyloxy-2-oxo-1S-phenethylpropylcarbamoyl)-2-methylbutyl]-3-fluorobenzamide (Compound 33); ¹H NMR (DMSO-d₆): δ 0.85–0.93 (m, 6H), δ 1.10–1.31 (m, 1H), δ 1.54 (m, 1H), δ 1.80–2.00 (m, 3H), δ 2.56–2.66 (m, 2H), δ 4.26–4.44 (m, 6H), δ 7.15–7.33 (m, 14H), δ 8.55–8.58 (d, 2H) LC-MS: M+1 (429.1);

tert-butyl 3-[1S-(3-benzyloxy-2-oxo-1S-phenethylpropylcarbamoyl)-2-methylbutylcarbamoyl] phenylcarbamate (Compound 34);

3-amino-N-[1S-(3-benzyloxy-2-oxo-1S-phenethylpropylcarbamoyl)-2-methylbutyl]benzamide (Compound 35);

N-[1S-(3-benzyloxy-2-oxo-1S-phenethylpropylcarbamoyl)-2-methylbutyl]-3-hydroxybenzamide (Compound 36);

tert-butyl 1-(3-benzyloxy-2-oxo-1-phenethylpropylcarbamoyl)-2-methylbutylcarbamate (Compound 37); ¹H NMR (CDCl₃): δ 0.87–0.92 (m, 6H), δ 1.02–1.22 (m, 1H), δ 1.4–1.5 (s, m, 10H), δ 1.75–1.95 (m, 2H), δ 2.15–2.30 (m, 1H), δ 2.5–2.7 (m, 2H), δ 2.89–3.95 (t, 1H), δ 4.12 (s, 2H), δ 4.48–4.62 (q, 2H), δ 4.85–5.0 (m, 2H), δ 6.49–6.52 (d, 1H), δ 7.07–7.4 (m, 10H), tert-butyl 1-(1-benzyloxyacetylpentylcarbamoyl)-2-methylbutylcarbamate (Compound 38); ¹H NMR (CDCl₃): δ 0.77–1.0 (m, 9H), δ 1.1–1.35 (m, 3H), δ 1.38–1.6 (s, m, 10H), δ 1.78–1.95 (m, 2H), δ 3.89–3.99 (t, 1H), δ 4.1–4.23 (m, 2H), δ 4.50–4.63 (q, 2H), δ 4.77–4.90 (m, 1H), δ 4.95–5.10 (d, 1H), δ 6.46–6.48 (d, 1H), δ 7.25–7.40 (m, 5H), tert-butyl 1-(3-benzyloxy-2-oxopropylcarbamoyl)-2-methylbutylcarbamate (Compound 39); ¹H NMR (CDCl₃): δ 0.80–1.0 (m, 6H), δ 1.02–1.22 (m, 1H), δ 1.4–1.5 (s, m, 10H), δ 1.80–2.0 (m, 1H), δ 3.90–4.10 (m, 1H), δ 4.11 (s, 2H), δ 4.30–4.32 (d, 2H), δ 4.58 (s, 2H), δ 4.90–5.10 (m, 1H), δ 6.50–6.70 (m, 1H), δ 7.24–7.50 (m, 5H), benzyl 2-naphthalen-2-yl-1S-(3-nitro-2-oxo-1S-phenethylpropylcarbamoyl)ethylcarbamate (Compound 40); ¹H NMR (300 MHz, DMSO-d₆): δ 1.72–1.86 (m, 1H), δ 1.98–2.10 (m, 1H), δ 2.39–2.62 (m, 2H), δ 3.00 (dd, 1H), δ 3.19 (dd, 1H), δ 4.21–4.32 (m, 1H), δ 4.38–4.48 (m, 1H), δ 4.90 (d, J=12.3 Hz, 1H), δ 4.95 (d, J=12.3 Hz, 1H), δ 5.50 (d, J=15.9 Hz, 1H), δ 5.57 (d, J=15.9 Hz, 1H), δ 7.12–7.26 (m, 10H), δ 7.41–7.46 (m, 3H), δ 7.78–7.84 (m, 5H), δ 8.74 (d, J=7.2 Hz, 1 NH); MS (ESI, m/z) 554.5 [M+H]⁺.

benzyl 3-methyl-1S-(3-nitro-2-oxo-1S-phenethylpropylcarbamoyl)butylcarbamate (Compound 41); ¹H NMR (270 MHz, CDCl₃) δ 0.91 (d, J=8.2 Hz, 3H), δ 0.93 (d, J=6.4 Hz, 3H), δ 1.40–1.50 (m, 1H), δ 1.56–1.66 (m, 2H), δ 1.90–2.00 (m, 1H), δ 2.16–2.29 (m, 1H), δ 2.55–2.70 (m, 2H), δ 4.06–4.14 (m, 1H), δ 4.43 (ddd, J=4.7, 7.1, 8.6 Hz, 1H), δ 4.96 (d, J=6.9 Hz, 1 NH), δ 5.06 (d, J=12.1 Hz, 1H), δ 5.11 (d, J=12.1 Hz, 1H), δ 5.21 (d, J=15.3 Hz, 1H), δ 5.37 (d, J=15.1 Hz, 1H), δ 6.59 (d, J=7.2 Hz, 1 NH), δ 7.10–7.32 (m, 10H); ¹³C NMR (CDCl₃, δ) 21.78, 22.96, 24.82, 31.34, 31.63, 40.31, 53.70, 56.99, 67.64, 81.25, 126.70, 128.32, 128.47, 128.60, 128.74, 128.95, 135.82, 139.98, 156.50, 172.93, 195.31; MS (ESI, m/z) 470.2 [M+H]⁺;

benzyl 2-naphthalen-2-yl-1-(1-nitroacetylpentylcarbamoyl)ethylcarbamate (Compound 42); ¹H NMR (DMSO-d₆): δ 0.81 (t, 3H), δ 1.19 (m, 4H), δ 1.53 (m, 1H), δ 1.73 (m, 1H), δ 2.97 (m, 1H), δ 3.13 (m, 1H), δ 4.34 (m, 2H), δ 4.93 (s, 2H), δ 5.56 (q, J=6.5 Hz, J=14 Hz, 2H), δ 7.23 (m, 5H), δ 7.47 (m, 3H), δ 7.82 (m, 5H), δ 8.63 (d, J=5.4 Hz, 1H); MS-CI 506.0 (M+H+, 80%); 401.2 (100%);

benzyl 2-methyl-1-(1-nitroacetylpentylcarbamoyl) butylcarbamate (Compound 43); ¹H NMR (DMSO-d₆): δ 0.88 (m, 9H), δ 1.16 (m, 3H), δ 1.59 (m, 4H), δ 1.97 (m, 2H), δ 3.99 (t, 1H), δ 4.47 (m, 1H), δ 5.09 (s, 2H), δ 5.14 (br.s, 1H), δ 5.56 (q, J=7.1 Hz, J=14 Hz, 2H), δ 6.43 (d, J=5.1 Hz, 1H), δ 7.34 (m, 5H); MS-CI 422.0 (M+H⁺, 100%), 2S-(3-benzylureido)-3-naphthalen-2-yl-N-(3-nitro-2-oxo-1S-phenethylpropyl)propionamide (Compound 44); ¹H NMR (270 MHz, DMSO-d₆): δ 1.77–1.88 (m, 1H), δ 1.98–2.10 (m, 1H), δ 2.39–2.62 (m, 2H), δ 3.00 (dd, J=8.9, 13.6 Hz, 1H), δ 3.18 (dd, J=5.7, 13.6 Hz, 1H), δ 4.16 (br.d, J=4.7 Hz, 2H), δ 4.22–4.30 (m, 1H), δ 4.56–4.64 (m, 1H), δ 5.48 (d, J=16.6 Hz, 1H), δ 5.57 (d, J=15.6 Hz, 1H), δ 6.39 (d, J=8.2 Hz, 1 NH), δ 6.53 (t, J=6.1 Hz, 1 NH), δ 7.11–7.28 (m, 10H), δ 7.43–7.51 (m, 3H), δ 7.76 (br.s, 1H), δ 7.79–7.88 (m, 4H), δ 8.76 (d, J=7.2 Hz, 1 NH); MS (ESI, m/z) 553.5 [M+H]⁺;

benzyl 2-methyl-1S-(3-nitro-2-oxo-1S-phenethylpropylcarbamoyl)butylcarbamate (Compound 45); ¹H NMR (300 MHz, DMSO-d₆): δ 0.77–0.88 (m, 6H), δ 1.06–1.22 (m, 1H), δ 1.36–1.48 (m, 1H), δ 1.69–1.86 (m, 2H), δ 1.98–2.12 (m, 1H), δ 2.4–2.7 (m, 2H), δ 3.87–3.93 (m, 1H), δ 4.22–4.30 (m, 1H), δ 5.00 (br.s, 2H), δ 5.71 (d, J=15.6 Hz, 1H), δ 5.81 (d, J=15.6 Hz, 1H), δ 7.14–7.30 (m, 10H), δ 7.50 (d, J=7.8 Hz, 1 NH), δ 8.66 (d, J=3.0 Hz, 1 NH); MS (ESI, m/z) 470.2 [M+H]⁺;

benzyl 1-nitroacetylpentylcarbamoyl)phenylmethylcarbamate (Compound 46); ¹H NMR (CDCl₃): δ 0.88 (m, 3H), δ 1.25 (m, 4H), δ 1.54 (m, 1H), δ 1.86 (m, 1H), δ 4.47 (m, 1H), δ 5.07 (q, J=5.7 Hz, J=13.5 Hz, 2H), δ 5.13–5.20 (m, 3H), δ 5.83 (d, J=6 Hz, 1H), δ 6.31 (br.d, 1H), δ 7.34 (m, 10H); MS-CI 442.0 (M+H⁺, 100%);

benzyl 5S-(2S-benzyloxycarbonylamino-3-naphthalen-2-ylpropionylamino)-7-nitro-6-oxoheptylcarbamate (Compound 47); ¹H NMR (DMSO): δ 1.21 (m, 5H), δ 1.76 (m, 1H), δ 2.97 (m, 3H), δ 3.17 (dd, 1H), δ 4.36–4.41 (m, 2H), δ 4.92 (s, 2H), δ 4.99 (s, 2H), δ 5.56 (d, 1H), δ 5.63 (d, 1H), δ 7.21–7.48 (14H), δ 7.78–7.88 (m, 5H), δ 8.66 (d, 1H); MS M+1 (655.3);

N-[3-methyl-1S-(3-nitro-2-oxo-1S-phenethylpropylcarbamoyl)butyl][1,4']bipiperidinyl-1'-carboxamide (Compound 48); ¹H NMR (270 MHz, DMSO-d₆): δ 0.88 (d, J=6.4 Hz, 3H), δ 0.92 (d, J=6.4 Hz, 3H), δ 1.35–2.12 (m, 15H), δ 2.47–2.72 (m, 4H), δ 2.83–2.96 (m, 2H), δ 3.25–3.52 (m, 3H), δ 4.08–4.22 (m, 4H), δ 5.74 (d, J=15.8 Hz, 1H), δ 5.83 (d, J=15.6 Hz, 1H), δ 6.67 (d, J=7.4 Hz, 1 NH), δ 7.15–7.31 (m, 5H), δ 8.63 (d, J=7.2 Hz, 1 NH), δ 8.99 (br.s, 1 NH); MS (ESI, m/z) 530.3 [M+H]⁺;

N-[3-methyl-1S-(3-nitro-2-oxo-1S-phenethylpropylcarbamoyl)butyl]-4-hydroxypiperidine-1-carboxamide (Compound 49); ¹H NMR (270 MHz, DMSO-d₆): δ 0.87 (d, J=6.4 Hz, 3H), δ 0.92 (d, J=6.4 Hz, 3H), δ 1.14–1.32 (m, 2H), δ 1.38–1.48 (m, 1H), δ 1.52–1.71 (m, 4H), δ 1.79–1.93 (m, 1H), δ 2.00–2.13 (m, 1H), δ 2.46–2.69 (m, 2H), δ 2.84–2.96 (m, 2H), δ 3.54–3.77 (m, 3H), δ 4.06–4.23 (m, 2H), δ 5.71 (d, J=15.6 Hz, 1H), δ 5.82 (d, J=15.8 Hz, 1H), δ 6.51 (d, J=7.4 Hz, 1 NH), 67.16–7.31 (m, 5H), δ 8.52 (d, J=6.9 Hz, 1 NH); MS (ESI, m/z) 463.2 [M+H]⁺;

benzyl 3-methyl-1S-(3-methyl-1S-nitroacetylbutylcarbamoyl)butylcarbamate (Compound 50); ¹H NMR (270 MHz, CDCl₃): δ 0.85–0.98 (m, 12H), δ 1.46–1.71 (m, 6H), δ 4.12–4.20 (m, 1H), δ 4.46–4.54 (m, 1H), δ 5.08 (br.s, 2H), δ 5.24–5.33 (m, 1H and 1 NH), δ 5.46 (d, J=15.3 Hz, 1H), δ 6.73 (d, J=6.2 Hz, 1 NH), δ 7.29–7.39 (m, 5H), δ ¹³C NMR (CDCl₃, δ) 21.48, 21.87, 22.93, 23.08, 24.79, 24.79, 38.58, 40.45, 53.69, 55.78, 67.56, 81.45, 128.20, 128.57, 128.74, 135.85, 156.54, 173.17, 196.00; MS (ESI, m/z) 470.2 [M+H]⁺;

benzyl 5S-[4-methyl-2S-(3-phenylpropionylamino)pentanoylamino]-7-nitro-6-oxoheptylcarbamate (Compound 51); ¹H NMR (DMSO-d₆): δ 0.811 (d, 3H), δ 0.86 (d, 3H), δ 1.23–1.79 (m, 7H), δ 2.49–2.50 (m, 4H), δ 2.76–2.79 (m, 2H), δ 2.96–2.98 (m, 2H), δ 4.21–4.26 (m, 2H), δ 4.99 (s, 1H), δ 5.78 (d, 1H), δ 5.73 (d, 1H), δ 7.19–7.33 (m, 11H), δ 8.06 (d, 1H), δ 8.48 (d, 1H); MS M+1 (569.3);

benzyl 2-methyl-1S-(3-nitro-2-oxo-1S-phenethylpropylsulfamoylmethyl)butylcarbamate (Compound 52); ¹H NMR (DMSO-d⁶): δ 0.75 (3H, d, J=7 Hz); 0.85 (3H, t, J=7 Hz); 1.00 (1H, m); 1.28 (1H, m); 1.5 (1H, m); 1.65 (1H, m); 1.95 (1H, m); 2.4–2.7 (3H, m*); 2.94 (2H, m); 3.96 (1H, m); 5.01 (2H, s); 6.49 (1H, s); 6.87 (1H, s, J=8 Hz); 7.15–7.35 (11H, m*). MS (M+1): 520;

benzyl 1S-(1S-nitroacetylpentylcarbamoyl)butylcarbamate (Compound 53);

benzyl 3-methyl-1R-(3-nitro-2-oxo-1S-phenethylpropylsulfamoylmethyl)butylcarbamate (Compound 54); ¹H NMR (DMSO-d⁶): δ 0.83 (6H, d, J=6 Hz); 1.38 (2H, m); 1.57 (1H, m*); 1.69 (1H, m*); 1.91 (1H, m); 2.63 (2H, m); 2.88–3.1 (2H, m); 3.99 (1H, m); 5.02 (2H, s); 5.99 and 6.56 (1H total 2×s, keto and enol form protons); 7.00 (1H, d, J=8 Hz) 7.16–1.34 (11H, m). MS (M+1): 520;

benzyl 3-methyl-1R-(1S-nitroacetylpentylsulfamoylmethyl)butylcarbamate (Compound 55); ¹H NMR (DMSO-d⁶): δ 0,75–0.87 (9H, m*); 1.2–1.65 (9H, m*); 2.83–3.3 (2H total, m, from keto and enol forms); 3.98 and 4.12 (1H, total, m, from keto and enol forms); 5.01 (2H, s); 5.94, 6.49 (1H, total, 2×s, from keto and enol forms); 1H, br.d); 7.32 (5H, m); 7.31, 7.83 (1H, total, 2×d). MS (M+1): 456;

tert-butyl 3-[2-methyl-1S-(1S-nitroacetylpentylcarbamoyl)butylcarbamoyl]benzylcarbamate (Compound 56); 3-aminomethyl-N-[2-methyl-1S-(1S-nitroacetylpentylcarbamoyl)butyl]benzamide (Compound 57); ¹H NMR (DMSO, d ppm) 0.85–0.92 (m, 9H), δ 1.26–1.95 (m, 9H), δ 4.06–4.07 (m 2H), δ 4.31–4.37 (m, 2H), δ 5.78 (d, 1H), δ 5.85 (d, 1H), δ 7.50–7.53 (m, 1H), δ 7.65 (d, 1H), δ 7.90 (d, 1H), δ 8.04 (s, 1H), δ 8.44–8.56 (m, 3H), δ 8.78 (d, 1H); MS M+1 (421.1);

benzyl 4S-(4-methyl-2S-piperidin-4-ylcarbonylaminopentanoylamino)-6-nitro-5-oxohexylcarbamate (Compound 58); ¹H NMR (DMSO): δ 0.81–0.86 (m, 7H), δ 1.43–1.80 (m, 10H), δ 2.84–2.99 (m, 2H), δ 3.21–3.54 (m, 10H), δ 5.00 (d, 21H), δ 7.27–7.66 (m, 6H), δ 8.63 (m, 1H), δ 9.07 (m, 1H); MS M+1 (534.3);

N-[2-naphthalen-2-yl-1S-(3-nitro-2-oxo-1S-phenethylpropylcarbamoyl)ethyl]piperidine-4-carboxyamide (Compound 59); $^1$H NMR (DMSO-d$_6$): δ 1.63–2.05 (m, 7H), δ 2.49–2.50 (m, 2H), δ 2.7502.78 (m, 2H), δ 3.04–3.23 (m, 5H), δ 4.52 (m, 1H), δ 5.57 (m, 1H), δ 7.10–7.49 (m, 7H), δ 7.72–7.83 (m, 6H), δ 8.35 (d, 1H), δ 8.66 (m, 1H), δ 9.08 (m, 1H); MS M+1 (531.2);

N-[3-methyl-1S-(3-nitro-2-oxo-1S-phenethylpropylcarbamoyl)butyl]piperidine-4-carboxamide (Compound 60);

benzyl 3-methyl-1S-(3-nitro-2-oxo-1S-benzylpropylcarbamoyl)butylcarbamate (Compound 61);

benzyl 1S-[1S-(1H-indol-3-ylmethyl)-3-nitro-2-oxopropylcarbamoyl]-3-methylbutylcarbamate (Compound 62);

benzyl 1S-(1S-benzyl-3-nitro-2-oxopropylcarbamoyl)-2-naphthalen-2-ylethylcarbamate (Compound 63);

benzyl ester N-[3-methyl-1S-(2-oxo-1S-phenethyl-3-phenoxypropylcarbamoyl)butyl]carbamate (Compound 64);

N-[3-methyl-1S-(2-oxo-1S-phenethyl-3-phenoxypropylcarbamoyl)butyl]-4-methylpiperazine-1-carboxamide (Compound 65);

tert-butyl 4-{1S-[3-(2,5-dichlorobenzoyloxy)-2-oxo-1S-phenethylpropylcarbamoyl]-3-methylbutylcarbamoyl}piperidine-1-carboxylate (Compound 66);

7-benzyloxycarbonylamino-3S-(2S-benzyloxycarbonylamino-4-methylpentanoylamino)-2-oxoheptyl 2,5-dichlorobenzoic acid (Compound 67);

benzyl 4-methyl-2-(2-oxo-1-phenethyl-3-phenoxypropylsulfamoyl)pentylcarbamate (Compound 68);

benzyl 1-(3-benzyloxy-2-oxopropylcarbamoyl)-2-methylbutylcarbamate (Compound 69);

benzyl 3-methyl-1-(2-oxo-3-phenoxypropylcarbamoyl) butylcarbamate (Compound 70);

N-[2-methyl-1-(2-oxo-3-phenoxypropylcarbamoyl)butyl] nicotinamide (Compound 71);

2-acetylamino-3-cyclohexyl-N-(2-oxo-3-phenoxypropyl) propionamide (Compound 72); and benzyl 1-(2-oxo-3-phenoxypropylcarbamoyl)-2-phenylethylcarbamate (Compound 73).

Example 3

Benzyl 1S-(3-Hydroxy-2-oxo-1S-phenethylpropylcarbamoyl)-3-methylbutylcarbamate (Compound 74)

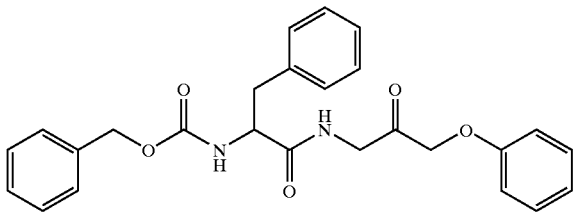

Potassium carbonate (31 mg, 0.225 mmol) was added to a solution comprised of the 3S-(2S-benzyloxycarbonylamino-4-methylpentanoylamino)-2-oxo-5-phenylpentyl 2,5-dichlorobenzoate (0.92 g, 1.5 mmol), provided as in Example 2, in 1:1 methanol/TBF (40 mL). The mixture was stirred for 60 minutes and then 1M hydrochloric acid (2 mL) was added. The mixture was concentrated in vacuo at room temperature and the residue was dissolved in ethyl acetate (40 mL). The solution was washed with 1M hydrochloric acid (5 mL) and saturated aqueous sodium bicarbonate (5 mL), dried (MgSO$_4$), filtered and concentrated. Product was purified from the residue by flash chromatography (50% CH$_2$Cl$_2$/ethyl acetate) to provide benzyl 1S-(3-hydroxy-2-oxo-1S-phenethylpropylcarbamoyl)-3-methylbutylcarbamate (0.37 g, 0.84 mmol) in approximately a 3:1 mixture of (S,S)- to (S,R)-diastereomers. $^1$H NMR (CDCl$_3$): 0.89 (2×d*, 6H, 2×CH$_3$), 1.43–1.6 (3H, m*, (CH$_3$)$_2$CHCH$_2$, δ 1.86 (1H, m, one CH$_2$CH$_2$C$_6$H$_5$, δ 2.12 (1H, m, other CH$_2$CH$_2$C$_6$H$_5$, δ 2.58 (2H, t, J=7.7 Hz, CH$_2$CH$_2$C$_6$H$_5$, δ 3.0 (1H, m*, OH), δ 4.2 (1H, CHNH (Leu)), δ 4.29 (2H, m*, CH$_2$OH), δ 4.61 (1H, m*, NHCHCOCH$_2$OH), δ 5.07 (2H, s*, C$_{6H5}$CH$_2$O), δ 5.29–4.58 (1H, 2×d, approx. 3:1 ratio (S,S:S,R diastereomers), CBZ-NH), δ 6.9 (1H, d, NHCHCOCH$_2$OH), δ 7.03–7.31 (10H, m*, aromatic CH). MS: 441 (M+1).

Proceeding as in Example 3 provided the following compounds of Formula I:

benzyl 5S-(2S-benzyloxycarbonylamino-4-methylpentanoylamino)-7-hydroxy-6-oxoheptylcarbamate as an approximately 2:1 diastereomeric mixture for L,L:L,D (Compound 75); MS (M+) 541: $^1$H NMR (DMSO-d$_6$): δ 0.87 (6H, 2×d, J=5 Hz); 1.15–1.57 (9H, m*); 3.1 (2H, m); 3.5–3.65 (1H, 2×m, 2:1 ratio); 4.3 (3H, m, CH$_2$OH and CHNH (Leu)); 4.55 (1H, m); 5.03 (4H, 2×AB, 2×C$_6$H$_5$CH$_2$O); 5.51 (1H, br.d); 5.68–5.76 (1H, 2×br.d, ~2:1 ratio); 7.2–7.25 (11H, aromatic CH, amide NH);

N-[1S-(3-hydroxy-2-oxo-1S-phenethylpropylcarbamoyl)-3-methylbutyl]-4-methylpiperazine-1-carboxamide as an approximately 9:1 diasteromeric mixture for L,L:L,D (Compound 76); $^1$H NMR (CDCl$_3$): δ 0.93 (3H, 2×d (appears as t), J=6 Hz); 1.51 (1H, m); 1.67 (2H. m); 1.91 (1H, m); 2.16 (1H, m); 2.31 (3H, s); 2.33 (4H, dd, appears as t, J=5.7 Hz); 2.62 (2H, m); 3.37 (4H, dd, appears as t, J=5.2 Hz); 4.30 (2H, 2×d (AB)); 4.36 (1H, m); 4.51 (1H, m); 4.89 (1H, d, J=8 Hz); 7.12–7.24 (6H, m); MS 433 (M+1);

5 N-[1S-(3-hydroxy-2-oxo-1R-phenethylpropylcarbamoyl)-3-methylbutyl]-4-methylpiperazine-1-carboxamide as an approximately 3:1 diasteromeric mixture for L,L:L,D (Compound 77); MS: 433 (M+1); $^1$H NMR (CDCl$_3$): δ 0.93 (3H, 2×d (appears as t), J=6 Hz); 1.62 (1H, m); 1.67 (2H. m); 1.91 (1H, m); 2.16 (1H, m); 2.28 (3H, s); 2.33 (4H, dd, appears as t, J=5.7 Hz); 2.62 (2H, m); 3.37 (4H, dd, appears as t, J=5.2 Hz); 4.30(2H, 2×d (AB)); 4.36(11H, m); 4.51 (1H, m); 5.11 (1H, d, J=8 Hz); 7.12–7.24 (5H, m); 7.44 (11H, m, J=8 Hz);

tert-butyl 4-[1S-(3-hydroxy-2-oxo-1S-phenethylpropylcarbamoyl)-3-methylbutylcarbamoyl] piperazine-1-carboxylate (Compound 78);

N-[1S-(3-hydroxy-2-oxo-1-phenethylpropylcarbamoyl)-3-methylbutyl]piperazine-1-carboxamide (Compound 79);

benzyl 1S-(1-benzyloxymethyl-3-hydroxy-2-oxopropylcarbamoyl)-3-methylbutylcarbamate (Compound 80); $^1$H NMR (CDCl$_3$): δ 0.91 (6H, 2×d, J=6 Hz); 1.52 (1H, m); 1.64 (2H, m); 3.12 (1H, m); 3.57

(1H, m); 3.84 (1H, m); 4.22 (1H, m); 4.30 (2H, br.s); 4.43 (2H, 2×d (AB)); 4.74 (1H, m); 5.08 (2H, 2×d (AB)); 5.32–5.43 (1H, 2×d, J=8 Hz, 1:1 ratio, L,L; L,D isomers); 7.04–7.17 (H, 2×d 1:1 ratio, L,L; L,D isomers); 7.24–7.37 (10H, m); MS (M+1): 457;

benzyl 1S-[3-hydroxy-1S-(1H-indol-3-ylmethyl)-2-oxopropylcarbamoyl]-3-methylbutylcarbamate (Compound 81); $^1$H NMR (CDCl$_3$): δ 0.84 (6H, m); 1.25–1.65 (3H, m); 3.13 (2H, m); 4.09 (2H, 2×d (AB), J=19 Hz); 4.25 (1H, m); 4.84 (1H, m); 5.00 (2H, 2×d (AB), J=11 Hz); 5.49–5.69 (1H, 2×d, J=8 Hz, approx. 4:1 ratio, L,L to L,D isomers); 6.81 (H, d, J=2 Hz); 7.04–7.29 (9 H, m); 7.5 (1H, d, J=7.6 Hz); 8.48 (1H, s); MS (M+1): 466;

benzyl 1S-(3-hydroxy-2-oxo-1S-phenethylpropylcarbamoyl)-2-methylpropylcarbamate as an approximately 2.5:1 diastereomeric mixture of L,L: L,D (Compound 82); $^1$H (CDCl$_3$): δ (6H, 2×d, J=6.7 Hz); 1.89 (1H, m); 2.12 (2H, m); 2.60 (2H, t, J=7.5 Hz); 3.98 (1H, m); 4.30 (2H, 2×s, ~2.5:1 ratio); 4.65 (1H, m); 5.90 (2H, s); 5.30 (1H, 2×d, ~2.5:1 ratio); 6.6 (1H, 2×br.d, ~2.5:1 ratio); 7.08–7.3 (10H, m); MS (M+1) 427;

N-[1S-(3-hydroxy-2-oxo-1S-phenethylpropylcarbamoyl)-3-methylbutyl]morpholine-4-carboxamide (Compound 83); $^1$H NMR (CDCl$_3$): δ 0.87 (6H, 2×d, J=7 Hz); 1.49–1.69 (3H, m); 1.82 (1H, m); 2.08 (1H, m); 2.55 (1H, m); 3.30 (4H, m); 3.56 (4H, m); 4.30 (2H, 2×d (AB), J=19 Hz); 4.37–4.5 (2H, m); 5.35 (1H, d, J=8 Hz); 7.04–7.27 (5H, m); 7.73 (1H, d, J=7 Hz); MS (M+1): 420;

benzyl 1-(3-hydroxy-2-oxo-1-phenethylpropylcarbamoyl)-2-naphthalen-2-ylethylcarbamate (Compound 84); $^1$H NMR (CDCl$_3$): δ 1.63 (m, 1H), δ 2.01 (m, 1H), δ 2.41 (m, 2H), δ 3.17 (m, 2H), δ 4.21 (q, J=13.1 Hz, J=6.3 Hz, 2H), δ 4.52 (m, 2H), δ 5.06 (s, 2H), δ 5.19 (m, 1H), δ 6.27 (br.s., 1H), δ 6.81 (d, J=7.1 Hz, 1H), δ 6.98 (d, J=7.3 Hz, 1H), δ 7.28 (m, 10H), δ 7.44 (m. 2H), δ 7.60 (m, 1H), δ 7.78 (m, 2H). LC-MS: 525.1 (M+H$^+$, 33%), 349 (40%), 305 (100%);

benzyl 1S-(3-hydroxy-2-oxo-1S-phenethylpropylcarbamoyl)-2-methylbutylcarbamate (Compound 85); $^1$H NMR (CDCl$_3$): δ 0.89 (3H, t, J=7 Hz); 0.91 (3H, d, J=7 Hz); 1.1 (1H, m); 1.47 (1H, m); 1.84 (2H, m); 2.13 (1H, m); 2.60 (2H, dd, J=7, 8 Hz); 4.01 (1H, m); 4.30 (2H, 2×s, 5:1 ratio, L,L:L,D isomers); 4.63 (1H, m); 5.09 (2H, s); 5.25–5.35 (1H, 2×d*, J=8.7 Hz, ~5:1 ratio); 6.57 (1H, d, J=7 Hz); 7.05–7.31 (10H, m); MS (M+1): 441;

benzyl 1S-[1S-(3-hydroxy-2-oxo-1S-phenethylpropylcarbamoyl)-3-methylbutylcarbamoyl]-3-methylbutylcarbamate (Compound 86); $^1$H NMR (CDCl$_3$): δ 0.85 (12H, m); 1.44–1.75 (6H, m); 1.82 (1H, m); 2.10 (1H, m); 2.57 (1H, m); 4.2–4.38 (2H, m); 4.45–4.61 (2H, m); 4.9 (1H, m); 5.05 (2H, 2×d (AB); 7.05–7.35 (10H, m); MS (M+1): 554;

N-[1S-(3-hydroxy-2-oxo-1S-phenethylpropylcarbamoyl)-3-methylbutyl]-1-methylpiperidine-4-carboxamide (Compound 87);

benzyl 2-hydroxy-1-(3-hydroxy-2-oxo-1-phenethylpropylcarbamoyl)propylcarbamate (Compound 88); $^1$H NMR (CDCl$_3$): δ 1.18 (d, J=8.1 Hz, 3H), δ 1.87 (m, 1H), δ 2.12 (m, 1H), δ 2.58 (m, 3H), δ 4.13 (m, 1H), δ 4.28 (m, 3H), δ 4.52 (m, 1H), δ 5.16 (s, 2H), δ 5.77 (br.d., 1H), δ 7.10 (d, J=7.1 Hz, 2H), δ 7.28 (m, 8H). LC-MS: 429.1 (M+H$^+$, 100%);

benzyl 1-(3-hydroxy-2-oxo-1-phenethylpropylcarbamoyl)pentylcarbamate (Compound 89); $^1$H NMR (CDCl$_3$,): δ 0.90 (t, J=8.5 Hz, 3H), δ 1.30 (m, 4H), δ 1.59 (m, 2H), δ 1.84 (m, 2H), δ 2.15 (m, 1H), δ 2.60 (t, J=7.4 Hz, 2H), δ 4.09 (m, 1H), δ 4.29 (s, 2H), δ 4.58 (m, 1H), δ 5.1 (s, 2H), δ 5.18 (br.s., 1H), δ 6.51 (br.d., 1H), δ 7.12 (m, 2H), δ 7.26 (m, 8H). LC-MS: 441.2 (M+H$^+$, 100%);

benzyl 5-(2-benzyloxycarbonylaminohexanoylamino)-7-hydroxy-6-oxoheptylcarbamate (Compound 90); $^1$H NMR (CDCl$_3$): δ 0.90 (t, J=8.5 Hz, 3H), δ 1.26 (m, 6H), δ 1.47 (m, 2H), δ 1.61 (m, 3H), δ 1.80 (m, 2H), δ 3.12 (m, 2H), δ 4.14 (m, 1H), δ 4.31 (s, 2H), δ 4.57 (m, 1H), δ 5.12 (s, 4H), δ 5.15 (br.s. 1H), δ 5.34 (br.s., 1H), δ 6.85 (br.d. 1H), δ 7.13 (m, 15H). LC-MS: 542.1 (M+H$^+$, 33%), 221 (40%), 157 (100%);

benzyl 1-[3-hydroxy-2-oxo-1-(2-phenylcarbamoylethyl)propylcarbamoyl]pentylcarbamate (Compound 91); $^1$H NMR (DMSO-d$_6$,): 0.90 (m, 3H), δ 1.30 (m, 3H), δ 1.59 (m, 3H), δ 2.15 (m, 2H), δ 2.40 (t, J=7.4 Hz, 2H), δ 4.09 (m, 2H), δ 4.17 (m, 1H), δ 4.36 (m, 1H), δ 4.68 (m, 1H), δ 5.1 (s, 2H), δ 5.18 (br.s., 1H), δ 6.51 (br.d., 1H), δ 7.12 (m, 2H), δ 7.26 (m, 8H). LC-MS: 484.2 (M+H$^+$, 100%);

benzyl 1S-(1S-hydroxyacetylpentylcarbamoyl)-3-methylbutylcarbamate (Compound 92);

benzyl 1S-[1S-(1S-hydroxyacetylpentylcarbamoyl)-3-methylbutylcarbamoyl]-3-methylbutylcarbamate (Compound 93); $^1$H NMR (CDCl$_3$): δ 0.81–0.9 (15H, m), δ 1.24 (4H, m), δ 1.4–1.8 (8H, m), δ 4.23 (1H, m), δ 4.34 (2H, 2×d (AB), J=19 Hz), δ 4.57 (2H, m), δ 5.04 (2H, 2×d (AB), J=12 Hz), δ 5.75 (1H, m), δ 7.18 (1H, m), δ 7.24–7.29 (6H, m);

tert-butyl 4-benzyloxycarbonylamino-4S-(3-hydroxy-2-oxo-1S-phenethylpropylcarbamoyl)butyrate (Compound 94); $^1$H NMR (CDCl$_3$, mixture of diastereomers): δ 1.44 (s, 9H), δ 1.83–1.96 (m, 2H), δ 1.98–2.25 (m, 2H), δ 2.26–2.52 (m, 2H), δ 2.58–2.65 (m, 2H), δ 4.16–4.23 (q, 1H), δ 4.30 and 4.31 (s and s, 2H), δ 4.54–4.63 (m, 1H), δ 5.62 and 5.74 (d and d, J=6.7 and 7.4 Hz, 1 NH), δ 6.93 and 7.01 (d and d, 1 NH), δ 7.10–7.33 (m, 10H); MS (ESI, m/z) 513.3 [M+H]$^+$;

benzyl 1-(1-hydroxyacetylpentylcarbamoyl)-2-naphthalen-2-ylethylcarbamate (Compound 95); $^1$H NMR (CDCl$_3$): 0.82 (m, 3H), δ 1.18 (m, 3H), δ 1.38 (m, 1H), δ 1.68 (m, 3H), δ 3.24 (m, 2H), δ 4.18 (m, 2H), δ 4.54 (m, 2H), δ 5.06 (s, 2H), δ 5.37 (br.s., 1H), δ 6.30 (br.s., 1H), δ 7.29 (m, 7H), δ 7.47 (m, 2H), δ 7.60 (m, 1H), δ 7.77 (m, 2H) MS: 477.2 (M+H$^+$, 100%);

benzyl 1-(1-hydroxyacetylpentylcarbamoyl)pentylcarbamate (Compound 96); $^1$H NMR (CDCl$_3$): 0.87 (m, 6H), δ 1.28 (m, 8H), δ 1.57 (m, 2H), δ 1.81 (m, 3H), δ 4.12 (m, 1H), δ 4.35 (s, 2H), δ 4.60 (m, 1H), δ 5.09 (s, 2H), δ 5.21 (br.d., 1H), δ 6.57 (br.d., 1H), δ 7.29 (m, 5H). LC-MS: 393.1 (M+H$^+$, 100%);

benzyl 1-[3-hydroxy-1-(4-methoxybenzyl)-2-oxopropylcarbamoyl]-2-naphthalen-2-ylethylcarbamate (Compound 97); $^1$H NMR (CDCl$_3$): δ 2.87 (q, J=14 Hz, J=7.1 Hz, 2H), δ 3.15 (m, 2H), δ 3.73 (s, 3H), δ 4.49 (m, 1H), δ 4.68 (s, 2H), δ 4.73 (m, 1H), δ 5.04 (s, 2H), δ 5.34 (br.d., 1H), δ 6.31 (br.d., 1H), δ 6.68 (d, J=7.5 Hz, 2H), δ 6.87 (d, J=8.10 Hz, 2H), δ 7.25 (m, 4H), δ 7.41 (m, 4H), δ 7.61 (s, 1H), δ 7.75 (m, 2H), δ 7.85 (m, 1H). LC-MS: 541.2 (M+H$^+$, 100%);

benzyl 1-[3-hydroxy-1-(4-methoxybenzyl)-2-oxopropylcarbamoyl]pentylcarbamate (Compound 98); $^1$H NMR (CDCl$_3$): 0.87 (m, 3H), δ 1.25 (m, 4H), δ 1.59 (m, 1H), δ 1.75 (m, 2H), δ 2.97 (m, 2H), δ 3.74 (s, 3H), δ 4.14 (m, 2H), δ 4.19 (m, 1H), δ 4.78 (m, 1H), δ 5.08 (s, 2H), δ 5.18 (br.s., 1H), δ 6.54 (br.s., 1H), δ 6.81 (d, J=8.1 Hz, 2H), δ 6.99 (d, J=7.7 Hz, 2H), δ 7.33 (m, 5H). LC-MS: 457.2 (M+H$^+$, 100%);

benzyl 1-[3-hydroxy-1-(4-methoxybenzyl)-2-oxopropylcarbamoyl]-2-phenylethylcarbamate (Compound 99); $^1$H NMR (CDCl$_3$): 2.75 (m, 2H), δ 3.01 (m, 2H), δ 3.73 (s, 3H), δ 3.81 (br.s, 1H), δ 4.07 (m, 2H), δ 4.36 (m, 1H), δ 4.70 (m, 1H), δ 5.05 (s, 2H), δ 5.24 (br.s., 1H), δ 6.34 (br.d., 1H), δ 6.74 (m, 2H), δ 6.87 (m, 2H), 7.26 (m, 2H), δ 7.38 (m, 8H). LC-MS: 491.2 (M+H$^+$, 100%);

1-tert-butoxymethyl-N-[1S-(3-hydroxy-2-oxo-1S-phenethylpropylcarbamoyl)-2-naphthalen-2-ylethyl]-piperidine-4-carboxamide (Compound 100); $^1$H NMR (CDCl$_3$): δ 1.43 (s, 9H), δ 1.5–1.7 (m, 6H), δ 1.99–2.11 (m, 1H), δ 2.12–2.28 (m, 1H), δ 2.43–2.49 (m, 2H), δ 2.62–2.75 (m, 2H), δ 3.10–3.30 (m, 2H), δ 4.02–4.22 (m, 4H), δ 4.42–4.52 (m, 1H), δ 4.66–4.74 (m, 1H), δ 6.09 (d, J=7.2 Hz, 1 NH), δ 6.32 (d, J=7.4 Hz, 1 NH), δ 6.98–7.02 (m, 2H), δ 7.16–7.26 (m, 3H), δ 7.32–7.36 (m, 1H), δ 7.42–7.49 (m, 2H), δ 7.63 (s, 1H), δ 7.73–7.83 (m, 3H); MS (ESI, m/z) 602.4 [M+H]$^+$;

N-[1S-(3-hydroxy-2-oxo-1S-phenethylpropylcarbamoyl)-2-naphthalen-2-ylethyl]piperidine-4-carboxyamide (Compound 101); $^1$H NMR (DMSO-d$_6$, (mixture of diastereomers): δ 1.4–2.1 (m, 6H), δ 2.25–2.65 (m, 3H), δ 2.70–2.90 (m, 2H), δ 2.95–3.30 (m, 4H), δ 4.05–4.32 (m, 3H), δ 4.65–4.76 (m, 1H), δ 6.98–7.30 (m, 5H), δ 7.38–7.52 (m, 3H), δ 7.70–7.88 (m, 4H), δ 8.2–8.5 (m, 2 NH), δ 8.5–8.8 (m, 2 NH); MS (ESI, m/z) 502.3 [M+H]$^+$;

benzyl 1-(3-hydroxy-2-oxo-1-phenethylpropylcarbamoyl)-4-methylpentylcarbamate (Compound 102); $^1$H NMR (CDCl$_3$): 0.91–0.93 (d, 6H), δ 1.21–1.24 (t, 1H), δ 1.42–1.53 (m, 1H), δ 1.60–1.68 (m, 1H), δ 1.78–1.93 (m, 1H), δ 2.13–2.30 (m, 1H), δ 2.54–2.62 (m, 2H), δ 4.09–4.14 (m, 2H), δ 4.48–4.60 (q, 2H), δ 5.09 (s, 1H), δ 6.52–6.55 (d, 1H), δ 7.07–7.37(m, 15H), δ M+H$^+$ (531.4);

N-[1S-(3-hydroxy-2-oxo-1S-phenethylpropylcarbamoyl)-2-phenylethyl]pyrrolidine-2-carboxamide hydrochoride (Compound 103); $^1$H NMR (DMSO-d$_6$): 1.6–2.1 (m, 4H), δ 2.20–2.70 (m, 2H), δ 3.0–3.30 (m, 3H), δ 3.56 (s, 1H), δ 4.04–4.19 (m, 2H), δ 4.20–4.40 (m, 1H), δ 4.63–4.70 (m, 1H), δ 7.07–7.40 (m, 10H), δ 8.66–8.75 (m, 1H), δ 8.89–8.92 (d,d, 1H), δ M+H$^+$ (438.2);

benzyl 3-carbamoyl-1S-(3-hydroxy-2-oxo-1S-phenethylpropylcarbamoyl)propylcarbamate (Compound 104); $^1$H NMR (CDCl$_3$, mixture of diastereomers): δ 1.8–2.1 (m, 2H), δ 2.1–2.2 (m, 2H), δ 2.3–2.5 (m, 2H), δ 2.6–2.7 (m, 2H), δ 4.2–4.4 (m, 3H), δ 4.6–4.7 (m, 1H), δ 5.8–6.0 (m, 2 NH) 6.1 and 6.2 (br.s and br.s, 1 NH), δ 7.1–7.4 (m, 10H), δ 7.7 (br.s, 1 NH); MS (ESI, m/z) 456.2 [M+H]$^+$;

benzyl 5-(2-benzyloxycarbonylamino-3-methylhexanoylamino)-7-hydroxy-6-oxoheptylcarbamate (Compound 105); $^1$H NMR (CDCl$_3$): δ 0.86 (m, 6H), δ 1.10 (m, 2H), δ 1.43 (m, 3H), δ 1.61 (m, 3H), δ 1.80 (m, 1H), δ 3.12 (m, 2H), δ 4.10 (m, 1H), δ 4.34 (s, 2H), δ 4.57 (m, 1H), δ 5.12 (s, 4H), δ 5.15 (m. 1H), δ 5.34 (br.s., 1H), δ 6.85 (br.d, 1H), δ 7.13 (m, 10H). LC-MS: 542.3 (M+H$^+$, 100%);

benzyl 4-carbamoyl-1S-(3-hydroxy-2-oxo-1R-phenethylpropylcarbamoyl)butylcarbamate (Compound 106); ESI-MS m/z 456.3 (M+H$^+$);

tert-butyl 2-[1S-(3-benzyloxy-2-oxo-1S-phenethylpropylcarbamoyl)-3-methylbutylcarbamoyl]pyrrolidine-1-carboxylate (Compound 107); $^1$H NMR (CDCl$_3$): 0.80–1.0 (m, 6H), δ 1.42 (s, 9H), δ 1.50–1.70 (m, 3H), δ 1.80–2.0 (m, 3H), δ 2.1–2.3 (m, 2H), δ 2.55–2.60 (t, 2H), δ 3.32–3.44 (m, 2H), δ 4.11–4.24 (m, 3H), δ 4.3–4.4 (m, 1H), δ 4.48–4.60 (q, 2H), δ 4.65–4.70 (m, 1H), δ 7.00–7.40 (m, 10H), δ M+H$^+$ (594.4);

2S-(3-benzylureido)-N-(3-hydroxy-2-oxo-1S-phenethylpropyl)-4-methylpentanamide (Compound 108); $^1$H NMR (DMSO-d$_6$, mixture of diastereomers): δ 0.89–0.94 (m, 6H), δ 1.34–1.49 (m, 2H), δ 1.59–1.69 (m, 1H), δ 1.71–1.84 (m, 1H), δ 1.91–2.08 (m, 1H), δ 2.44–2.66 (m, 2H), δ 4.10–4.35 (m, 6H), δ 5.07 (br.s, 1H), δ 6.18 (d, J=8.4 Hz, 1 NH), δ 6.46 (t, J=5.3 Hz, 1 NH), δ 7.14–7.30 (m, 10H), δ 8.41 and 8.51 (d and d, J=7.6 and 7.9 Hz, 1 NH); MS (ESI, m/z) 440.2 [M+H]$^+$;

tert-butyl 4-[1S-(5-benzyloxycarbonylamino-1S-hydroxyacetylpentylcarbamoyl)-2-naphthalen-2-ylethylcarbamoyl]piperidine-1-carboxylate (Compound 109); $^1$H NMR (DMSO-d$_6$, mixture of diastereomers): δ 1.35 (s, 9H), δ 1.01–1.80 (m, 10H), δ 2.24–2.36 (m, 1H), δ 2.52–2.76 (m, 2H), δ 2.81–2.98 (m, 3H), δ 3.06–3.22 (m, 1H), δ 3.64–3.90 (m, 2H), δ 4.11–4.20 (m, 2H), δ 4.28–4.38 (m, 1H), δ 4.60–4.70 (m, 1H), δ 4.89 and 5.00 (br.s and br.s, 2H), δ 5.02–5.10 (m, 1H), δ 7.17–7.38 (m, 6H), δ 7.42–7.50 (m, 3H), δ 7.70–7.88 (m, 5H), δ 8.12–8.17 (m, 1 NH), δ 8.31–8.36 (m, 1 NH); MS (ESI, m/z) 703.4 [M+H]$^+$;

benzyl 1S-(1S-hydroxyacetylpentylcarbamoyl)-2-methylbutylcarbamate (Compound 110); $^1$H NMR (DMSO-d$_6$): δ 0.78–0.85 (m, 9H), δ 1.1401.24 (m, 7H), δ 1.41–1.69 (m, 2H), δ 4.15 (t, 1H), δ 4.17–4.19 (m, 2H), δ 4.35 (m, 1H), δ 5.02–5.10 (m, 3H), δ 7.34–7.68 (m, 5H), δ 8.17 (d, 1H); MS M+1 (393.1);

tert-butyl 2-[1-(3-hydroxy-2-oxo-1-phenethylpropylcarbamoyl)-2-methylbutylcarbamoyl]-ethylcarbamate (Compound 1H); $^1$H NMR (CDCl$_3$): 0.92 (m, 6H), δ 1.11 (m, 1H), δ 1.42 (s, 9H), δ 1.84 (m. 4H), δ 2.44 (m, 2H), δ 2.63 (m, 2H), δ 3.39 (t, J=8.6 Hz, 2H), δ 4.24 (m, 1H), δ 4.31 (s, 2H), δ 4.62 (m, 2H), δ 6.19 (br.s., 1H), δ 6.50 (br.d., 1H), δ 7.24 (m, 5H). LC-MS: 478.1 (M+H$^+$, 20%); 378 (100%);

2-(3-aminopropionylamino)-N-(3-hydroxy-2-oxo-1-phenethylpropyl)-3-methylpentanamide hydrochloride (Compound 112); $^1$H NMR (MeOH-d$_4$, d ppm): 0.92 (m, 6H), δ 1.11 (m, 1H), δ 1.84 (m. 4H), δ 2.44 (m, 2H), δ 2.63 (m, 2H), δ 3.39 (t, J=8.6 Hz); 4.24 (m, 1H), δ 4.31 (s, 2H), δ 4.62 (m, 2H), δ 6.19 (br.s., 1H), δ 6.50 (br.d., 1H), δ 7.24 (m, 5H). LC-MS: 378.1 (M+H$^+$, 100%);

tert-butyl 3-[1-(3-hydroxy-2-oxo-1-phenethylpropylcarbamoyl)-2-methylbutylcarbamoyl]propylcarbamate (Compound 113); $^1$H NMR (CDCl$_3$): 0.92 (m, 6H), δ 1.11 (m, 1H), δ 1.42 (s, 9H), δ 1.84 (m. 4H), δ 2.23 (m, 2H), δ 2.61 (m, 2H), δ 3.08 (m, 2H), δ 4.39 (m, 3H), δ 4.58 (m, 1H), δ 4.95 (br.s., 1H), δ 7.20 (m, 5H). LC-MS: 492.1 (M+H$^+$, 20%); 392 (100%);

2-(4-aminobutyrylamino)-N-(3-hydroxy-2-oxo-1-phenethylpropyl)-3-methylpentanamide hydrochloride (Compound 114); ¹H NMR (MeOH-d₄): 0.92 (m, 6H), δ 1.11 (m, 1H), δ 1.84 (m. 4H), δ 2.23 (m, 2H), δ 2.61 (m, 2H), δ 3.08 (m, 2H), δ 4.39 (m, 3H), δ 4.58 (m, 1H), δ 4.95 (br.s. 1H), δ 7.20 (m, 5H). LC-MS: 392.1 (M+H⁺, 100%);

tert-butyl 5-[1-(3-hydroxy-2-oxo-1-phenethylpropylcarbamoyl)-2-methylbutylcarbamoyl]pentylcarbamate (Compound 115); ¹H NMR (CDCl₃): 0.92 (m, 6H), δ 1.13 (m, 1H), δ 1.34 (m, 1H), δ 1.42 (s, 9H), δ 1.48–1.53 (m, 5H), δ 1.64 (m, 1H), δ 1.84–2.00 (m. 4H), δ 2.23 (m, 2H), δ 2.62 (m, 2H), δ 3.08 (m, 2H), δ 4.24 (m, 1H), δ 4.33 (m, 2H), δ 4.61 (m, 1H), δ 6.01 (br.s. 1H), δ 6.60 (br.s. 1H), δ 7.24 (m, 5H). LC-MS: 520.1 (M+H⁺, 20%); 420.1 (20%); 392 (100%);

6-amino-N-[1-(3-hydroxy-2-oxo-1-phenethylpropylcarbamoyl)-2-methylbutyl]hexanamide hydrochloride (Compound 116);

N-[1S-(3-hydroxy-2-oxo-1S-phenethylpropylcarbamoyl)-2-methylbutyl][1,4'bipiperidinyl-1'-carboxamide (Compound 117); ¹H NMR (DMSO-d₆): δ 0.80–0.87 (m, 6H), δ 1.23–1.64 (m, 15H), δ 2.46–2.61 (m, 10H), δ 3.99–4.19 (m, 6H), δ 6.37 (d, 1H), δ 7.16–7.23 (m, 5H), δ 8.29 (d,1H); MS M+1 (501.4);

N-[1S-(3-hydroxy-2-oxo-1S-phenethylpropylcarbamoyl)-2-methylbutyl]-4-methylpiperazine-1-carboxamide (Compound 118); ¹H NMR (DMSO-d₆, mixture of diastereomers): δ 0.80–0.87 (m, 6H), δ 1.15 (m, 1H), δ 1.77 (m, 1H), δ 1.79–2.22 (m, 10H), δ 2.55–2.58 (m, 2H), δ 3.31–3.40 (m, 6H), δ 4.00–4.26 (m, 3H), δ 6.35 (m, 1H), δ 7.15–7.23 (m, 5H), δ 8.29, 8.31 (d, 1H); MS M+1 (433.2);

N-(3-hydroxy-2-oxo-1S-phenethylpropyl)-3-methyl-2S-phenylacetylaminopentanamide (Compound 119); ¹H NMR (CDCl₃). 0.79–0.86 (6H, d, t, J=7 Hz); 1.0 (1H, m); 1.24–1.38 (2H, m); 1.79 (2H, m); 2.07 (1H, m); 2.53 (2H, m); 3.55 (2H, s); 4.28 (2H, s); 4.32 (1H, m); 4.51 (1H, m); 6.16 (1H, d, J=8.6 Hz); 7.05–7.26 (11H, m); MS (M+1): 425;

tert-butyl 2-benzyloxycarbonylamino-2-(3-hydroxy-2-oxo-1-phenethylpropylcarbamoyl)ethylcarbamate (Compound 120); ¹H NMR (CDCl₃): 1.42 (s, 9H), δ 1.87 (m, 1H), δ 2.17 (m, 1H), δ 2.62 (m, 2H), δ 4.28 (m, 3H), δ 4.54 (m, 1H), δ 5.13 (s, 2H), δ 5.17 (m, 1H), δ 6.26 (br.s., 1H), δ 6.39 (br.s. 1H), δ 2.30 (m, 10H). LC-MS: 514.2 (M+H⁺, 100%);

tert-butyl 1-[1-(3-hydroxy-2-oxo-1-phenethylpropylcarbamoyl)-2-methylbutylcarbamoyl]-2-phenylethylcarbamate (Compound 121); ¹H NMR (CDCl₃): 0.92 (m, 6H), δ 1.11 (m, 1H), δ 1.24 (m, 2H), δ 1.42 (s, 9H), δ 1.98 (m. 4H), δ 2.63 (m, 2H), δ 3.31 (m, 2H), δ 4.21 (m, 1H), δ 4.30 (s, 2H), δ 4.56 (m, 1H), δ 5.00 (br.s.), δ 6.00 (br.s., 1H), δ 6.31 (br.d., 1H), δ 7.24 (m, 10H). LC-MS: 554.2 (M+H⁺, 20%); 422.9 (30%); 317 (33%); 275.9 (100%);

tert-butyl 1-(3-hydroxy-2-oxo-1-phenethylpropylcarbamoyl)-2-methylbutylcarbamoylmethylcarbamate (Compound 122);

benzyl 2-biphenyl-4-yl-1-(3-hydroxy-2-oxo-1-phenethylpropylcarbamoyl)ethylcarbamate (Compound 123); ¹H NMR (CDCl₃): 1.85 (m, 2H), δ 2.12 (m, 2H), δ 2.49 (m, 2H), δ 3.08 (m, 2H), δ 4.21 (m, 2H), δ 4.40 (m, 1H), δ 4.56 (m, 1H), δ 5.04 (s, 2H), δ 5.14 (br.s, 1H), δ 6.32 (br.s, 1H), δ 7.02 (m, 2H), δ 7.24–7.51 (m, 16H). LC-MS: 551.2 (M+H⁺, 100%);

benzyl 1-(3-hydroxy-2-oxo-1-phenethylpropylcarbamoyl)-2-(4-nitrophenyl)ethylcarbamate (Compound 124); ¹H NMR (CDCl₃, mix. of diastereomers): 1.85 (m, 2H), δ 2.12 (m, 2H), δ 2.56 (m, 2H), δ 3.06 (m, 1H), δ 3.21 (m, 1H), δ 4.29 (m, 2H), δ 4.37 (m, 1H), δ 4.62 (m, 1H), δ 5.04 (s, 2H), δ 5.14 (br.s. 1H), δ 6.39. 6.59 (br.s., 1H), δ 7.23 (d, J=8.1 Hz, 2H), δ 7.28 (m, 10H), δ 8.08 (d J=8.3 Hz, 2H). LC-MS: 520.2 (M+H⁺, 100%);

methyl N-[1S-(3-hydroxy-2-oxo-1S-phenethylpropylcarbamoyl)-2-methylbutyl]succinamate (Compound 125); ¹H NMR (CDCl₃): 0.94 (6H, d, t, J=7 Hz); 1.12 (1H, m); 1.47 (1H, m); 1.98 (2H, m); 2.20 (1H, m); 2.46 (2H, m); 2.55–2.9 (4H, m); 3.61 (3H, s); 4.30 (2H, s); 4.31 (2H, m); 4.61 (1H, m); 5.97 (1H, d, J=8 Hz); 6.89 (1H, d, J=7 Hz); 7.14–7.27 (5H); MS (M+1): 421;

2-(2-aminoacetylamino)-N-(3-hydroxy-2-oxo-1-phenethylpropyl)-3-methylpentanamide hydrochloride (Compound 126); ¹H NMR (MeOH-d₄): 0.91 (m, 6H), δ 1.11 (m, 1H), δ 1.96 (m. 5H), δ 2.63 (m, 2H), δ 3.78 (m, 2H), δ 4.21 (m, 1H), δ 4.30 (m, 2H), δ 4.62 (m, 1H), δ 5.10 (br.s. 1H), δ 6.39 (br.s., 1H), δ 6.50 (br.s., 1H), δ 7.24 (m, 5H). LC-MS: 364.2 (M+H⁺, 100%);

2-(2-amino-3-phenylpropionylamino)-N-(3-hydroxy-2-oxo-1-phenethylpropyl)-3-methylpentanamide hydrochloride (Compound 127);

benzyl 2-amino-1-(3-hydroxy-2-oxo-1-phenethylpropylcarbamoyl)ethylcarbamate hydrochloride (Compound 128); ¹H NMR (MeOH-d₄): 1.87 (m, 1H), δ 2.17 (m, 1H), δ 2.62 (m, 2H), δ 4.28 (m, 3H), δ 4.54 (m, 1H), δ 5.13 (s, 2H), δ 5.17 (m, 1H), δ 6.26 (br.s., 1H), δ 6.39 (br.s. 1H), δ 2.30 (m, 10H). LC-MS: 414.2 (M+H⁺, 100%).

N-(3-hydroxy-2-oxo-1-phenethylpropyl)-3-methyl-2-(naphthalen-2-ylsulfonylamino)pentanamide (Compound 129); ¹H NMR (CDCl₃): 0.91 (m, 6H), δ 1.11 (m, 1H), δ 1.58–1.77 (m, 4H), δ 2.30 (t, J=7.9 Hz, 2H), δ 3.58 (m, 1H), δ 4.21 (m, 2H), δ 4.42 (m, 1H), δ 5.14 (d, J=7.9 Hz, 1H), δ 6.28 (d, J=7.3 Hz, 1H), δ 6.94 (d, J=8.2 Hz, 2H), δ 7.24 (m, 3H), δ 7.55 (m, 2H), δ 7.81 (m, 2H), δ 7.93 (m, 2H), δ 8.41 (m, 1H). LC-MS: 497.2 (M+H⁺, 100%);

N-[1-(3-hydroxy-2-oxo-1-phenethylpropylcarbamoyl)-2-methylbutyl]naphthalene-2-carboxamide (Compound 130); ¹H NMR (DMSO-d₆): 0.93 (m, 6H), δ 1.21 (m, 1H), δ 1.64 (m, 1H), δ 2.05 (m, 3H), δ 2.63 (m, 2H), δ 4.30 (m, 2H), δ 4.63 (m, 2H), δ 6.82–7.37 (m, 6H), δ 7.55 (m, 1H), δ 7.86 (m, 4H), δ 8.37 (m, 1H). LC-MS: 461.2 (M+H⁺, 100%);

2S-(3-benzylureido)-N-(3-hydroxy-2-oxo-1S-phenethylpropyl)-3-methylpentanamide (Compound 131); ¹H NMR (DMSO-d₆, mixture of diastereomers): δ 0.83–0.89 (m, 6H), δ 1.02–1.14 (m, 1H), δ 1.40–1.52 (m, 1H), δ 1.65–1.84 (m, 2H), δ 1.94–2.06 (m, 1H), δ 2.48–2.68 (m, 2H), δ 4.10–4.36 (m, 6H), δ 5.08 (br.s, 1H), δ 6.16 (d, J=9.1 Hz, 1 NH), δ 6.50–6.54 (m, 1 NH), δ 7.14–7.32 (m, 10H), δ 8.41 and 8.51 (d and d, J=7.4 and 7.4 Hz, 1 NH); MS (ESI, m/z) 440.1 [M+H]⁺;

tert-butyl 3-[1S-(3-hydroxy-2-oxo-1S-phenethylpropylcarbamoyl)-2-methylbutylcarbamoyl]benzylcarbamate (Compound 132); ¹H NMR (CDCl₃): 0.89 (3H, t, J=7 Hz); 0.93 (3H, d, 7 Hz); 1.2 (1H, m); 1.42 (9H, s); 1.62 (1H, m); 1.97 (1H, m); 2.05 (2H, m); 2.48–2.63 (2H, m, 2 isomers, LL, LD at Ile-HpH), δ 4.23 (2H, m); 4.33 (2H, d, 2: J=8 Hz); 4.57 (1H, m);

4.64 (1H, m); 5.10 (1H, m); 7.09 (1H, m); 7.14–7.8 (9H, m). MS: 540 (M+1);

benzyl 7-hydroxy-5S-[3-naphthalen-1-yl-2S-(piperidin-4-ylcarbonylamino)propionylamino]-6-oxoheptylcarbamate (Compound 133); $^1$H NMR (DMSO-d$_6$, mixture of diastereomer): δ 1.0–1.8 (m, 10H), δ 2.35–2.48 (m, 1H), δ 2.7–3.5 (m, 8H), δ 4.09–4.18 (m, 2H), δ 4.18–4.36 (m, 1H), δ 4.62–4.71 (m, 1H), δ 4.92–5.10 (m, 3H), δ 7.16–7.50 (m, 5H), δ 7.40–7.50 (m, 3H), δ 7.71–7.87 (m, 5H), δ 8.1–8.7 (br.m, 4 NH); MS (ESI, m/z) 603.3 [M+H]$^+$;

benzyl 3-(3-hydroxy-2-oxo-1-phenethylpropylcarbamoyl)-3,4-dihydro-1H-isoquinoline-2-carboxyate (Compound 134); $^1$H NMR (CDCl$_3$): 1.55 (m, 2H), δ 1.88 (m, 2H), δ 3.10 (m, 1H), δ 3.29 (m, 1H), δ 4.08 (m, 1H), δ 4.17 (m, 1H), δ 4.40 (m, 1H), δ 4.62 (m, 2H), δ 4.88 (m, 1H), δ 5.22 (s, 2H), δ 6.90 (br.s, 1H), δ 7.21 (m, 13H). LC-MS: 487.2 (M+H$^+$, 100%);

benzyl cyclohexyl-(1S-hydroxyacetylpentylcarbamoyl) methylcarbamate (Compound 135); $^1$H NMR (CDCl$_3$): δ 1.26 (m, 8H), δ 1.62 (m, 9H), δ 4.18 (m, 1H), δ 4.35 (s, 2H), δ 4.58 (m, 2H), δ 5.03 (br.s., 1H), δ 5.10 (s, 2H), δ 6.47 (br.s, 1H), δ 7.33 (m, 10H). LC-MS: 419.2 (M+H$^+$, 100%);

N-[1S-(3-hydroxy-2-oxo-1S-phenethylpropylcarbamoyl)-2S-methylbutyl] isonicotinamide (Compound 136); $^1$H NMR (DMSO-d$_6$, mixture of diastereomers): δ 0.86–1.02 (m, 6H), δ 1.17–1.31 (m, 1H), δ 1.51–1.66 (m, 1H), δ 1.90–2.08 (m, 2H), δ 2.08–2.23 (m, 1H), δ 2.50–2.67 (m, 2H), δ 3.65 and 3.71 (s, and s, 2H), δ 4.49–4.66 (m, 2H), δ 6.68 and 6.84 (d and d, J=7.9 Hz, 1 NH), δ 7.00–7.30 (m, 6H), δ 7.62–7.67 (m, 2H), δ 8.68–8.78 (m, 2H); MS (ESI, m/z) 412.2 [M+H]$^+$;

N-(3-hydroxy-2-oxo-1S-phenethylpropyl)-3-methyl-2S-(3-phenylpropionylamino)pentanamide (Compound 137); $^1$H NMR (DMSO-d$_6$): δ 0.76–0.84 (m, 6H), δ 1.06 (m, 1H), δ 1.36 (m, 1H), δ 1.69–1.98 (m, 2H), δ 2.45–3.00 (m, 6H), δ 4.15–4.25 (m, 4H), δ 5.08 (t, 1H), δ 7.17–7.26 (m, 10H), δ 7.99 (d, 1H), δ 8.38 (d, 1H); MS: M+1 (439.2);

tert-butyl 4-[1S-(1S-benzyloxymethyl-3-hydroxy-2-oxopropylcarbamoyl)-2-naphthalen-2-ylethylcarbamoyl]piperidine-1-carboxylate (Compound 138); $^1$H NMR (DMSO-d$_6$, mixture of diastereomers): δ 1.35 (s, 9H), δ 1.23–1.56 (m, 4H), δ 2.22–2.34 (m, 1H), δ 2.50–2.75 (m, 2H), δ 2.88–3.26 (m, 2H), δ 3.62–3.86 (m, 4H), δ 4.1–4.3 (m, 2H), δ 4.35–4.55 (m, 2H), δ 4.62–4.78 (m, 2H), δ 5.14–5.20 (m, 1H), δ 7.25–7.35 (m, 5H), δ 7.40–7.50 (m, 3H), δ 7.70–7.87 (m, 4H), δ 8.15–8.19 (m, 1 NH), δ 8.43 and 8.48 (d and d, J=7.2 Hz, 1 NH); MS (ESI, m/z) 618.3 [M+H]$^+$;

N-(3-hydroxy-2-oxo-12-phenethylpropyl)-2S-(2-1H-indol-3-ylacetylamino)-3-methylpentanamide (Compound 139); $^1$H NMR (CDCl$_3$): 0.93 (m, 6H), δ 1.21 (m, 1H), δ 1.34 (m, 1H), δ 1.43 (m, 1H), δ 1.73 (m, 2H), δ 1.96 (m, 1H), δ 2.05 (m, 3H), δ 2.54 (m, 2H), δ 3.58 (m, 2H), δ 4.15 (m, 2H), δ 4.28 (m, 2H), δ 6.82 (m, 1H), δ 6.91 (m, 1H), δ 7.37 (m, 5H), δ 7.56 (m, 1H), δ 7.98 (m, 1H), δ 8.50 (m, 1H), δ 10.85 (s, 1H). LC-MS: 464.2 (M+H$^+$, 100%);

N-(3-hydroxy-2-oxo-1S-phenethylpropyl)-2S-(3,3-diphenylpropionylamino)-3-methylpentanamide (Compound 140); $^1$H NMR (CDCl$_3$): 0.65 (m, 6H), δ 0.85–1.00 (m, 3H), δ 1.57–1.94 (m, 4H), δ 2.58–2.78 (m, 2H), δ 3.10 (m, 1H), δ 3.19 (m, 2H), δ 4.13 (s, 1H), δ 4.22–4.46 (m, 2H), δ 6.91–7.41 (m, 15H), δ 7.97 (s, 1H), δ 8.34 (s, 1H). LC-MS: 515.2 (M+H$^+$, 100%);

N-[1S-(3-hydroxy-2-oxo-1S-phenethylpropylcarbamoyl)-2-methylbutyl] naphthalene-1-carboxamide (Compound 141); $^1$H NMR (DMSO-d$_6$): 0.93 (m, 6H), δ 1.24 (m, 1H), δ 1.59 (m, 1H), δ 1.81 (m, 1H), δ 2.05 (m, 2H), δ 2.63 (m, 2H), δ 4.15 (m, 2H), δ 4.22 (m, 1H), δ 4.55 (m, 1H) 5.08 (m, 1H), δ 7.19 (m, 5H), δ 7.60 (m, 2H), δ 7.98 (m, 4H), δ 8.56 (m, 3H). LC-MS: 461.2 (M+H$^+$, 100%);

2S-(3-benzylureido)-N-(3-hydroxy-2-oxo-1S-phenethylpropyl)-3-naphthalen-2-ylpropionamide (Compound 142); $^1$H NMR (DMSO-d$_6$, mixture of diastereomers): δ 1.74–1.88 (m, 1H), δ 1.95–2.10 (m, 1H), δ 2.48–2.65 (m, 2H), δ 2.89–3.28 (m, 2H), δ 4.03–4.39 (m, 5H), δ 4.61–4.69 (m, 1H), δ 6.25–6.33 (m, 1 NH), δ 6.49–6.54 (m, 1 NH), δ 6.94–7.28 (m, 10H), δ 7.41–7.50 (m, 3H), δ 7.74 (br.s, 1H), δ 7.79–7.89 (m, 4H), δ 8.53 (d, J=7.7 Hz, 1 NH); MS (ESI, m/z) 524.3 [M+H]$^+$;

N-(3-hydroxy-2-oxo-1S-phenethylpropyl)-3-methyl-2S-(2-pyridin-4-ylacetylamino)pentanamide (Compound 143); $^1$H NMR (DMSO-d$_6$, mixture of diastereomers): δ 0.67–0.98 (m, 6H), δ 1.15–1.57 (m, 2H), δ 1.83–2.11 (m, 3H), δ 2.53–2.66 (m, 2H), δ 3.72 (s, 2H), δ 4.26–4.30 (m, 4H), δ 7.12–7.17 (m, 5H), δ 7.45–7.47 (m, 2H), δ 8.32, 8.41(m, 4H); MS: M+1 (426.1);

N-[1S-(3-hydroxy-2-oxo-1S-phenethylpropylcarbamoyl)-2-methylbutyl]benzamide (Compound 144);

tert-butyl 4-[1S-(3-hydroxy-2-oxo-1S-phenethylpropylcarbamoyl)-3-methylbutylcarbamoyl] benzylcarbamate (Compound 145); $^1$H NMR (DMSO-d$_6$): 0.93 (m, 6H), δ 1.38 (s, 9H), δ 1.56 (m, 1H), δ 1.73 (m, 2H), δ 1.81 (m, 1H), δ 2.63 (m, 2H), δ 4.15 (m, 2H), δ 4.22 (m, 1H), δ 5.08 (m, 1H), δ 7.19 (m, 4H), δ 7.32 (m, 1H), δ 7.88 (m, 2H), δ 8.56 (m, 2H). LC-MS: 540.1 (M+H$^+$, 100%);

4-aminomethyl-N-[1S-(3-hydroxy-2-oxo-1S-phenethylpropylcarbamoyl)-3-methylbutyl]benzamide hydrochoride (Compound 146); $^1$H NMR (DMSO-d$_6$): 0.93 (m, 6H), δ 1.56 (m, 1H), δ 1.73 (m, 2H), δ 1.81 (m, 1H), δ 2.63 (m, 2H), δ 4.15 (m, 2H), δ 4.22 (m, 3H), δ 5.08 (m, 1H), δ 7.19 (m, 4H), δ 7.32 (m, 1H), δ 7.88 (m, 2H), δ 8.56 (m, 2H). LC-MS: 440.1 (M+H$^+$, 100%);

N-(3-hydroxy-2-oxo-1S-phenethylpropyl)-3-methyl-2S-(2-pyridin-3-ylacetylamino)pentanamide (Compound 147); $^1$H NMR (DMSO-d$_6$): δ 0.78–0.86 (m, 6H), δ 1.15 (m, 1H), δ 1.44 (m, 1H), δ 1.72–1.77 (m, 3H), δ 2.50–2.59 (m, 2H), δ 3.48–3.62 (m, 2H), δ 4.14–4.26 (m, 4H), δ 5.08 (m, 1H), δ 7.14–7.67 (m, 6H), δ 7.65 (m, 1H), δ 8.35–8.46 (m, 4H); MS: M+1 (426.1);

tert-butyl 4-[1S-(1S-hydroxyacetylpentylcarbamoyl)-2-methylbutylcarbamoyl]benzylcarbamate (Compound 148); $^1$H NMR (DMSO-d$_6$): 0.88 (m, 9H), δ 1.23 (m, 5H), δ 1.42 (s, 9H), δ 1.56 (m, 1H), δ 1.69 (m, 2H), δ 1.81 (m, 1H), δ 4.19 (m, 5H), δ 4.36 (m, 1H), δ 5.08 (t, J=8.3 Hz, 1H), δ 7.32 (m, 2H), δ 7.45 (t, J=8.0 Hz, 1H), δ 7.83 (d, J=8.1 Hz, 1H), δ 8.30 (d, J=7.5 Hz, 1H). LC-MS: 492.3 (M+H$^+$, 100%);

4-aminomethyl-N-[1S-(1S-hydroxyacetylpentylcarbamoyl)-2-methylbutyl] benzamide hydrochloride (Compound 149);

N-[1S-(3-hydroxy-2-oxo-1S-phenethylpropylcarbamoyl)-2-methylbutyl]isophthalamide (Compound 150); $^1$H NMR (DMSO-d$_6$): 0.80–1.0 (m, 6H), δ 1.19–1.3 (m, 1H), δ 1.50–1.60 (m, 1H), δ 1.70–1.85 (m, 1H), δ 1.90–2.10 (m, 1H), δ 3.60–3.70 (m, 1H), δ 4.17–4.19 (d, 2H), δ 4.29–4.35 (m, 1H), δ 4.40–4.45 (t, 1H), δ 5.0–5.10 (m, 1H), δ 7.14–7.30 (m, 4H), δ 7.50–7.60 (m, 1H), δ 8.0–8.10 (m, 2H), δ 8.37 (s, 1H), δ 8.50–8.53 (d, 1H), δ M+H$^+$ (454.2);

4-benzyloxycarbonylamino-4S-(3-hydroxy-2-oxo-1S-phenethylpropylcarbamoyl)butyric acid (Compound 151); $^1$H NMR (DMSO-d$_6$) 1.70–2.05 (m, 4H), δ 2.31 (t, J=7.7 Hz, 2H), δ 2.5–2.7 (m, 2H), δ 4.03–4.3 (m, 4H), δ 5.04 (br.s, 2H), δ 7.12–7.35 (m, 10H), δ 7.75 (d, J=7 Hz, 1 NH), δ 8.36 (d, J=7.4 Hz, 1 NH), δ 12.2 (br.s, 1);

N-[1S-(1S-hydroxyacetylpentylcarbamoyl)-2-methylbutyl]isophthalamide (Compound 152); $^1$H NMR (CD$_3$OD): 0.80–1.10 (m, 9H), δ 1.30–1.35 (m, 6H), δ 1.51–1.71 (m, 2H), δ 1.80–1.90 (m, 1H), δ 1.90–2.10 (m, 1H), δ 4.34 (s, 2H), δ 4.44–4.61 (m, 2H), δ 7.54–7.60 (t, 1H), δ 7.97–8.04 (m, 2H), δ 8.33 (s, 1H), δ M+H$^+$ (406.1);

4-aminomethyl-N-[1S-(1S-hydroxyacetylpentylcarbamoyl)-2-naphthalen-2-ylethyl]benzamide hydrochloride (Compound 153); $^1$H NMR (DMSO-d$_6$): 0.72 (s, 3H), δ 1.10 (m, 1H), δ 1.25–1.31 (m, 3H), δ 1.54 (m, 1H), δ 1.75 (m, 1H), δ 3.26–3.31 (m, 2H), δ 4.04 (s, 2H), δ 4.25–4.58 (m, 6H), δ 4.90 (br.s., 1H), δ 7.31–7.72 (m, 10H), δ 7.83–7,92 (m, 5H), δ 8.21 (br.s, 2H), δ 8.56 (d, J=8.1 Hz, 1H), δ 8.74 (d, J=8.1 Hz, 1H). LC-MS: 566.3 (M+H$^+$, 100%);

3-aminomethyl-N-[1S-(1S-hydroxyacetylpentylcarbamoyl)-2-naphthalen-2-ylethyl]benzamide hydrochloride (Compound 154); MS: 476.2 (M+H$^+$, 100%);

tert-butyl 4-[1-(3-hydroxy-2-oxo-1-phenethylpropylcarbamoyl)-2S-methylbutylcarbamoyl]piperidine-1-carboxylate (Compound 155); $^1$H NMR (DMSO-d$_6$, mixture of two less polar diastereomers) 0.79–0.87 (m, 6H), δ 1.02–1.18 (m, 1H), δ 1.38 (s, 9H), δ 1.3–1.5 (m, 3H), δ 1.56–1.78 (m, 3H), δ 1.85–2.00 (m, 2H), δ 2.4–2.8 (m, 5H), δ 3.58 and 3.59 (br.s and br.s, 2H), δ 3.92 (br.d, J=12 Hz, 2H), δ 4.08–4.30 (m, 2H), δ 7.15–7.28 (m, 5H), δ 7.83 and 7.92 (d and d, J=8.9 Hz, 1 NH), δ 8.44 and 8.47 (d and d, J=7.4 and 7.9 Hz, 1 NH); MS (ESI, m/z) 518.3 [M+H]$^+$;

tert-butyl 4-[1-(3-hydroxy-2-oxo-1-phenethylpropylcarbamoyl)-2S-methylbutylcarbamoyl]piperidine-1-carboxylate (Compound 156); $^1$H NMR (DMSO-d$_6$, mixture of two more polar diastereomers): δ 0.80–0.87 (m, 6H), δ 1.04–1.18 (m, 1H), δ 1.38 (s, 9H), δ 1.3–1.5 (m, 3H), δ 1.556–1.82 (m, 4H), δ 1.90–2.05 (m, 1H), δ 2.4–2.8 (m, 5H), δ 3.58 and 3.59 (br.s and br.s, 2H), δ 3.92 (br.d, J=12 Hz, 2H), δ 4.08–4.30 (m, 2H), δ 7.15–7.28 (m, 5H), δ 7.83 and 7.92 (d and d, J=8.9 Hz, 1 NH), δ 8.44 and 8.47 (d and d, J=7.4 and 7.9 Hz, 1 NH); MS (ESI, m/z) 518.3 [M+H]$^+$;

3-fluoro-N-[1S-(3-hydroxy-2-oxo-1S-phenethylpropylcarbamoyl)-2-methylbutyl]benzamide (Compound 157); $^1$H NMR (DMSO-d$_6$): δ 0.84–0.95 (m, 6H), δ 1.20–2.00 (m, 5H), δ 2.50–2.60 (m, 2H), δ 4.16–4.37 (m, 4H), δ 5.06–5.08 (m, 1H), δ 7.15–7.75 (m, 9H), δ 8.52–8.59 (m, 2H); MS: M+1 (429.1);

2S-(dibenzofuran-2-sulfonylamino)-N-(3-hydroxy-2-oxo-1S-phenethylpropyl)-3-methylpentanamide (Compound 158); $^1$H NMR (CD$_3$OD): 0.76–0.98 (m, 6H), δ 1.0–1.20 (m, 2H), δ 1.40–1.60 (m, 1H), δ 1.65–1.81 (m, 2H), δ 1.95–2.10 (m, 1H), δ 2.40–2.60 (m, 1H), δ 3.68–3.80 (m, 2H), δ 4.02 (s, 2H), δ 4.29–4.34 (m, 1H), δ 6.81–6.82 (m, 1H), δ 7.08–7.21 (m, 4H), δ 7.35–7.75 (m, 4H), δ 8.00–8.19 (m, 4H), δ 7.95–8.15 (m, 2H), δ 8.58 (m, 1H), δ M+H$^+$ (537.2);

N-[1-(3-hydroxy-2-oxo-1-phenethylpropylcarbamoyl)-2S-methylbutyl]piperidine-4-carboxamide (Compound 159); $^1$H NMR (DMSO-d$_6$, mixture of two less polar diastereomers): δ 0.80–0.88 (m, 6H), δ 1.06–1.16 (m, 1H), δ 1.36–1.52 (m, 1H), δ 1.66–2.02 (m, 7H), δ 2.5–2.7 (m, 3H), δ 2.76–2.92 (m, 2H), δ 3.21–3.33 (m, 2H), δ 3.58 and 3.59 (br.s and br.s, 2H), δ 4.07–4.32 (m, 2H), δ 7.15–7.32 (m, 5H), δ 8.01–8.09 (m, 1 NH), δ 8.52 and 8.58 (d and d, J=7.4 and 7.2 Hz, 1 NH), δ 8.5–8.65 (br, 1 NH), δ 8.9–9.0 (br, 1 NH); MS (ESI, m/z) 418.2 [M+H]$^+$;

N-[1-(3-hydroxy-2-oxo-1-phenethylpropylcarbamoyl)-2S-methylbutyl]piperidine-4-carboxamide (Compound 160); $^1$H NMR (DMSO-d$_6$, mixture of two less polar diastereomers): δ 0.80–0.88 (m, 6H), δ 1.06–1.18 (m, 1H), δ 1.36–1.50 (m, 1H), δ 1.66–2.04 (m, 7H), δ 2.5–2.7 (m, 3H), δ 2.75–2.91 (m, 2H), δ 3.2–3.3 (m, 2H), δ 3.56 (s, 2H), δ 4.07–4.32 (m, 2H), δ 7.14–7.32 (m, 5H), δ 8.05–8.16 (m, 1 NH), δ 8.47 and 8.57 (d and d, J=7.4 and 7.2 Hz, 1 NH), δ 8.5–8.65 (br, 1 NH), δ 8.9–9.05 (br, 1 NH); MS (ESI, m/z) 418.2 [M+H]$^+$;

N-[1-(3-hydroxy-2-oxo-1-phenethylpropylcarbamoyl)-2-methylbutyl]-3-ureido-benzamide (Compound 161); $^1$H NMR (DMSO-d$_6$): δ 0.93 (m, 6H), δ 1.11 (m, 1H), δ 1.56 (m, 2H), δ 1.81 (m, 1H), δ 2.00 (m, 2H), δ 2.51 (m, 2H), δ 4.17 (m, 2H), δ 4.37 (m, 2H), δ 5.06 (s, 1H), δ 1.68 (s, 2H), δ 7.25 (m, 5H), δ 7.61 (m, 1H), δ 7.82 (s, 1H), δ 8.30 (br.d, 1H), δ 8.43 (br.d, 1H), δ 8.70 (s, 1H). LC-MS: 469.1 (M+H$^+$, 100%);

tert-butyl 3-[1S-(3-hydroxy-2-oxo-1S-phenethylpropylcarbamoyl)-2-methylbutylcarbamoyl]phenylcarbamate (Compound 162);

3-amino-N-[1S-(3-hydroxy-2-oxo-1S-phenethylpropylcarbamoyl)-2-methylbutyl]benzamide (Compound 163);

3-hydroxy-N-[1S-(3-hydroxy-2-oxo-1S-phenethylpropylcarbamoyl)-2-methylbutyl]benzamide (Compound 164); and benzyl 1S-(3-hydroxyacetyl-3,4-dihydro-1H-isoquinolin-2-ylcarbonyl)-3-methylbutylcarbamate (Compound 165).

Example 4

Benzyl 1-(3-Hydroxy-3-methyl-2-oxo-1-phenethylbutylcarbamoyl)-3-methylbutylcarbamate (Compound 166)

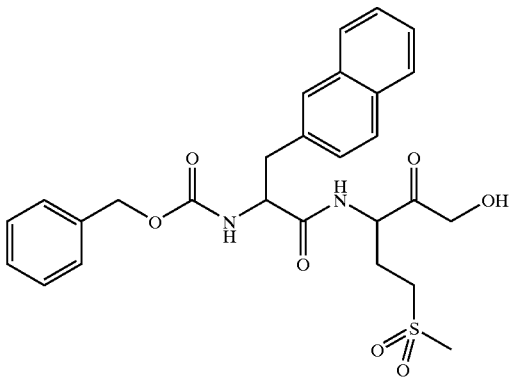

(a) A solution comprised of isopropyltriphenylphosphonium iodide (13.02 g, 30.1 mmol) in TBF (80 mL) was cooled to −78° C. and then n-butyllithium (12.44 mL, 2.5M in hexane) was added. The mixture was stirred for 5 minutes, heated to room temperature and stirred for an additional 25 minutes. Benzyl 1-(1-formyl-3-phenylpropylcarbamoyl)-3-methylbutylcarbamate (4.12 g, 10.04 mmol), prepared as in the procedure set forth in Synthesis, 1983, pp 676–678, was dissolved in THF (40mL) and the solution was added dropwise. The mixture was stirred for 18 hours at room temperature and then diluted with water (5 mL) and ethyl acetate (250 mL). The organic layer was washed with 1M hydrochloric acid, saturated aqueous sodium bicarbonate and brine, dried ($MgSO_4$) and concentrated to dryness in vacuo. Product was purified from the residue by column chromatography using 20% ethyl acetate/hexane to provide benzyl 3-methyl-1-(3-methyl-1-phenethylbut-2-enylcarbamoyl)butylcarbamate (0.75 g, 1.68 mmol) as a clear oil.

(b) A solution comprised of benzyl 3-methyl-1-(3-methyl-1-phenethylbut-2-enylcarbamoyl)butylcarbamate (0.750 g, 1.72 mmol) in acetonitrile (10 mL) was cooled in an ice bath and then 4-methylmorpholine N-oxide (0.403 g, 3.44 mmol) and osmium tetroxide (2.0 mL, 4% by weight solution in water) were added. The mixture was stirred, while continually cooled in the ice bath, for 18 hours and then diluted with 1M hydrochloric acid and ethyl acetate. The mixture was washed with saturated aqueous sodium bicarbonate, dried ($MgSO_4$) and concentrated to dryness in vacuo. Product was purified from the residue by column chromatography in 20% ethyl acetate/methylene chloride to provide benzyl 1-(2,3-dihydroxy-3-methyl-1-phenethylbutylcarbamoyl)-3-methylbutylcarbamate (0.25 g, 0.53 mmol) as a white solid.

(c) A solution comprised of benzyl 1-(2,3-dihydroxy-3-methyl-1-phenethylbutylcarbamoyl)-3-methylbutylcarbamate (0.250 g, 0.532 mmol) and Dess-Martin Periodate (0.451 g, 1.06 mmol) in dry methylene chloride (27 mL) was stirred vigorously and then a mixture of wet methylene chloride (20 mL, 95 mL of dry methylene chloride and 95 μL of water) was added by a separatory funnel. The mixture was stirred 18 hours at room temperature and concentrated to dryness in vacuo. The residue was dissolved in ethyl acetate and the solution was washed with saturated aqueous sodium bicarbonate and brine, dried ($MgSO_4$) and concentrated to dryness in vacuo. Product was purified from the residue by prep HPLC using 100% water to 20% water/acetonitrile over a 60 minute period. The desired fractions were collected and lyophilized to dryness to provide benzyl 1-(3-hydroxy-3-methyl-2-oxo-1-phenethylbutylcarbamoyl)-3-methylbutylcarbamate (0.05 g, 0.11 mmol) as a white solid. $^1$H NMR ($CDCl_3$): 0.89–0.91 (m, 6H), δ 1.23–1.32 (2×s, 6H), δ 1.42–4.65 (m, 2H), δ 1.86–1.89 (m, 1H), δ 2.05–2.15 (m, 1H), δ 2.58–2.63 (m, 2H), δ 4.12 (m, 1H), δ 5.09–5.21 (m, 4H), δ 6.52 (d, 1H), δ 7.12–7.31 (m, 10H).

Example 5 tert-Butyl 1S-(3-Hydroxy-2-oxo-1S-phenethylpropylcarbamoyl)-1-methylbutylcarbamate (Compound 167)

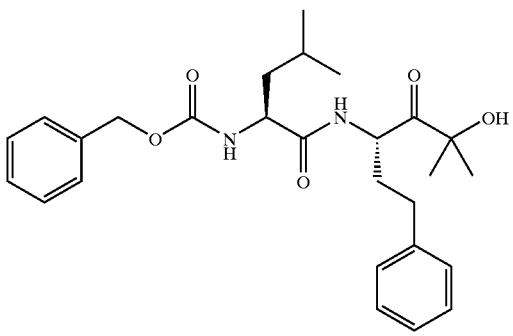

A mixture comprised of tert-butyl 1S-(3-benzyloxy-2-oxo-1S-phenethylpropylcarbamoyl)-1-methylbutylcarbamate (200 mg, 0.4 mmol), provided as in Example 1, cyclohexene (4.2 mL, 41.46 mmol) and a catalytic amount of 20% palladium hydroxide on carbon (44 mg) in 6 mL ethanol was heated at reflux until the reaction was complete. The mixture then was cooled to room temperature and filtered through celite. The filtrate was concentrated to provide tert-butyl 1S-(3-hydroxy-2-oxo-1S-phenethylpropylcarbamoyl)-2-methylbutylcarbamate (161 mg, 0.4 mmol); $^1$H NMR ($CDCl_3$): 0.80–0.95 (m, 6H), δ 1.0–1.32 (m, 2H), δ 1.42 (s, 9H), δ 1.75–2.05 (m, 2H), δ 2.10–2.35 (m, 1H), δ 2.59–2.65 (m, 2H), δ 3.88–3.94 (t, 1H), δ 4.32 (s, 2H), δ 4.55–4.75 (m, 1H), δ 5.02–5.05 (m, 1H), δ 6.72–6.75 (d, 1H), δ 7.10–7.4 (m, 5H).

Proceeding as in Example 8 provided the following compounds of Formula I:

N-[1S-(1S-hydroxyacetylpentylcarbamoyl)-2-methylbutyl]benzamide (Compound 168); $^1$H NMR ($CDCl_3$): 0.78 (3H, t, J=6 Hz); 0.92 (3H, t, J=7 Hz); 0.98 (3H, d, J=7 Hz); 1.1–1.35 (5H, br.m); 1.45–1.7 (2H, m); 1.81 (1H, m); 1.99 (1H, m); 3.15 (<1H, br.m*, $CH_2OH$), δ 4.39 (2H, s, $CH_2OH$), δ 4.6 (2H, m, 2×CHNH), δ 6.87 (1H, d, J=8 Hz); 7.02 (1H, d, J=7 Hz); 7.41–5.51 (3H, m); 7.76 (2H, m); MS (M+1): 363;

tert-butyl 4-(1S-{3-hydroxy-1-[2S-(4-hydroxyphenyl)ethyl]-2-oxopropylcarbamoyl}-2-methylbutylcarbamoyl)piperidine-1-carboxylate (Compound 169); $^1$H NMR ($CDCl_3$): 0.87–0.91 (6H, 2×d, J=7 Hz); 1.42 (9H, s); 1.5–1.8 (7H, m*); 2.01 (1, m); 2.22 (1H, m); 2.4–2.67 (6H, m*); 4.00–4.1 (2H, m*); 4.29 (2H, s); 4.51 (2H, m*); 6.47 (1H, d, J=9 Hz); 6.68 (2H, d, J=8 Hz); 6.84 (2H, d, J=8 Hz); 7.37 (1H, d, J=7 Hz); MS (M+1): 534;

N-(3-hydroxy-2-oxo-1S-phenethylpropyl)-3-methyl-2S-(2-phenoxyacetylamino)pentanamide (Compound 170); ¹H NMR (CDCl₃): 0.88 (3H, t, J=7 Hz); 0.92 (3H, d, J=7 Hz); 1.09 (1H, m); 1.44 (1H, m); 1.63 (1H, m); 1.91 (2H, m); 2.18 (1H, m); 2.60 (2H, dd, J=7, 8 Hz); 4.31 (1H, m*); 4.34 (2H, s); 4.53 (2H, 2×d (AB), J=15 Hz); 4.59 (1H, m); 6.51 (1H, m); 6.9–7.3 (11H, m); MS (M+1): 441;

N-{1-[3-hydroxy-2-oxo-1-(2-phenylcarbamoylethyl) propylcarbamoyl]-2-methylbutyl}naphthalene-2-carboxamide (Compound 171);

N-[1-(2-hydroxyacetylpyrrolidin-1-ylcarbonyl)-2-methylbutyl]naphthalene-2-carboxamide (Compound 172);

N-(1-hydroxyacetylpentyl)-2,2-dimethyl-propionamide (Compound 173); and benzyl 1-[3-hydroxy-1-(2-methanesulfonylethyl)-2-oxopropylcarbamoyl]-2-naphthalen-2-ylethylcarbamate (Compound 174); ¹H NMR (CDCl₃): δ 0.05 ppm (s, 1H), δ 0.85–0.9 ppm (t, 4H), δ 1.20 ppm (s, 10H), δ 1.1–1.2 ppm (m, 1H), δ 1.5–1.75 ppm (m, 4H), δ 1.75–1.8 ppm (m, 1H), δ 4.36 ppm (s, 2H), δ 4.58–4.65 (m, 1H), δ 6.07 (m, 1H); LC/MS (229.8 M+H⁺).

Example 6

3-Aminomethyl-N-[1S-(3-hydroxy-2-oxo-1S-phenethylpropylcarbamoyl)-2-methylbutyl] benzamide Hydrochloride (Compound 175)

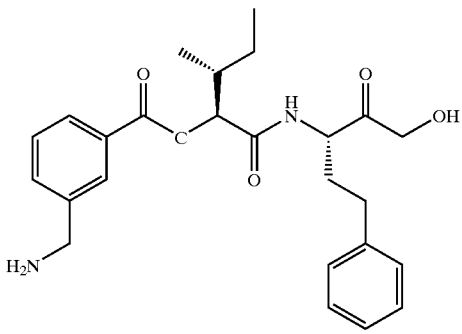

A solution comprised of tert-butyl 3-[1S-(3-hydroxy-2-oxo-1S-phenethylpropylcarbamoyl)-2-methylbutylcarbamoyl]benzylcarbamate (0.135 g, 0.25 mmol) in methylene chloride (2 mL) was combined with a solution of hydrogen chloride in dioxane (0.625 mL, 4.0 M). The mixture was stirred at room temperature for 3 hours and then ether (100 mL) was added to provide a precipitate. The precipitate was collected by filtering and washed with ether (2×30 mL) and hexane (2×30 mL) and dried in vacuo to provide 3-aminomethyl-N-[1S-(3-hydroxy-2-oxo-1S-phenethylpropylcarbamoyl)-2-methylbutyl]benzamide hydrochloride (95 mg, 0.2 mmol). ¹H NMR (DMSO-d⁶): δ 0.86 (3H, t, J=7 Hz); 0.94 (3H, d, J=7 Hz); 1.24 (1H, m); 1.57 (1H, m); 1.8 (1H, m); 1.98 (2H, m); 2.6–2.75 (2H, m); 4.07 (2H, br.q, J=6 Hz); 4.17 (2H, 2×d(AB)); 4.3 (1H, m); 4.42 (1H, m); 7.12–7.31 (5H, m); 7.52 (1H, t, J=8 Hz); 7.65 (1H, d, J=8 Hz); 7.95 (1H, d, J=8 Hz); 8.07 (1H, s); 8.42 (3H, br.s); 8.48 (1H, d); 8.65 (0.7H, d) 8.7 (0.3H, d). LC/MS indicated an approximately 3:1 ratio of diastereomers (L,L:L,D) regardless of synthetic route. MS: (M+1, 440).

Proceeding in a fashion analogous to the procedures exemplified above provided the following compounds of Formula I:

N-(1S-{3-hydroxy-1-[2S-(4-hydroxyphenyl)ethyl]-2-oxopropylcarbamoyl}-2-methylbutyl)piperidine-4-carboxylamide (Compound 176); MS (M+1): 434. ¹H NMR (DMSO-d⁶): 0.99 (6H, 2×d, J=6 Hz); 1.4–2 (9H, m*); 2.3–2.5 (5H, m, incl. DMSO); 2.84 (2H, m); 3.2–3.7 (3H, m*); 3.6 (1H, s); 4.1–4.3 (2H, 2×d* (AB)); 4.2 (1H, m*); 4.33 (1H, m*); 6.65 (2H, d, J=8 Hz); 6.95 (2H, d, J=8 Hz); 8.19 (1H, d, J=8 Hz); 8.37 (1H, d, J=7 Hz); 8.64 (1H, br.); 9.05 (1H, br.); 9.22 (1H, br.); MS (M+1): 434;

N-[3-methyl-1S-(2-oxo-1S-phenethyl-3-phenoxypropylcarbamoyl)butyl]-piperidine-4-carboxamide (Compound 177);

3S-(4-methyl-2S-piperidin-4-ylcarbonylaminopentanoylamino)-2-oxo-5-phenylpentyl 2,5-dichlorobenzoate (Compound 178);

benzyl 3-methyl-1S-(3-methyl-1S-phenoxyacetylbutylcarbamoyl)butylcarbamate (Compound 179);

N-[2-naphthalen-2-yl-1S-(2-oxo-1S-phenethyl-3-phenoxypropylcarbamoyl)ethyl]piperidine-4-carboxamide (Compound 180);

benzyl 1S-(3-ethoxy-2-oxo-1S-phenethylpropylcarbamoyl)-3-methylbutylcarbamate (Compound 181); ¹H NMR (CDCl₃): δ 0.91–93 ppm (d, 6H), δ 1.17–1.22 ppm (t, 3H), δ 1.40–1.7 ppm (m, 4H), δ 1.75–1.9 ppm (m, 2H), δ 2.2–2.3 ppm (m, 1H), δ 2.55–2.65 ppm (t, 2H), δ 3.45–3.6 ppm (q,m, 3H), δ 4.09–4.11 ppm (m, 2H), δ 4.84.9 ppm (m, 1H), δ 5.1 ppm (s, 2H), δ 6.48–6.52 ppm (d, 1H), δ 7.11–7.32 ppm (m, 10H); LC/MS (469.2 M+H⁺);

N-[3-methyl-1S-(2-oxo-1S-phenethyl-3-phenoxypropylcarbamoyl)butyl]piperidine-4-carboxamide (Compound 182);

benzyl 1S-(3-hydroxy-2-oxo-1S-phenethylpropylcarbamoyl)ethylcarbamate (Compound 183);

tert-butyl 2-[1S-(3-hydroxy-2-oxo-1S-phenethylpropylcarbamoyl)-3-methylbutylcarbamoylpyrrolidine-1-carboxylate (Compound 184);

N-[1-(2-benzyloxyacetylpyrrolidin-1-ylcarbonyl)-3-methylbutyl]naphthalene-2-carboxamide (Compound 185);

N-[1S-(3-benzyloxy-2-oxo-1S-phenethylpropylcarbamoyl)-2-methylbutyl]benzamide (Compound 186);

4-aminomethyl-N-[1S-(1S-benzyloxyacetylpentylcarbamoyl)-2-methylbutyl] benzamide (Compound 187);

N-[1S-(3-hydroxy-2-oxo-1S-phenethylpropylcarbamoyl)-2-methylbutyl]pyrazine-2-carboxamide (Compound 188);

tert-butyl 3-[1S(3-methoxy-2-oxo-1Sphenethylpropylcarbamoyl)-2-methylbutylcarbamoyl]benzylcarbamate (Compound 189); ¹H NMR (CDCl₃): δ 0.85–1.01 ppm (m, 6H), δ 1.23 ppm (m. 1H), δ 1.44 ppm (s, 9H), δ 1.8–2.0 ppm (m, 2H), δ 2.15–2.3 ppm (m, 1H), δ 2.58–2.63 ppm (t, 2H), δ 3.34 ppm (s, 1H), δ 3.38 ppm (s, 2H), δ 4.04–4.11 ppm (m, 2H); δ 4.32–4.34 ppm (m, 2H), δ 4.5–4.65 ppm (m, 1H), δ 4.8–5.0 ppm (m, 2H), δ 6.49–6.51 ppm (d, 1H), δ 6.70–6.73 ppm (d, 1H), δ 7.1–7.5 ppm (m, 7 H), δ 7.65–7.69 ppm (m, 2H); LC/MS (554.3 M+H⁺);

3-aminomethyl-N-[1-(3-methoxy-2-oxo-1-phenethylpropylcarbamoyl)-2-methylbutyl]benzamide (Compound 190); ¹H NMR (CDCl₃): δ 0.85–1.0 ppm (m, 6H), δ 1.1–1.3 ppm (m, 1H), δ 1.52–1.58 ppm (m, 1H), δ 1.8–2.0 ppm (m, 2H), δ 2.1–2.2 ppm (m, 1H), δ 3.19 ppm (m, 3H), δ 3.67 ppm (s, 2H), δ 4.18–4.20 ppm (m, 2H), δ 4.3–4.4 ppm (m, 3H), δ 7.1–7.35 ppm (m, 5H), δ 7.5–7.65 ppm (m, 2H), δ 7.75–7.8 ppm (m, 2H); LC/MS (454.1 M+H⁺);

tert-butyl 3-[2-methyl-1S-(2-oxo-1S-phenethyl-3-phenoxypropylcarbamoyl)butylcarbamoyl]benzylcarbamate (Compound 191);

tert-butyl 2-naphthalen-2-yl-1S-(2-oxo-1S-phenethyl-3-phenoxypropylcarbamoyl)ethylcarbamate (Compound 192);

3-aminomethyl-N-[2-naphthalen-2-yl-1S-(2-oxo-1S-phenethyl-3-phenoxypropylcarbamoyl)ethylbenzamide (Compound 193);

3-aminomethyl-N-[2-methyl-1S-(2-oxo-1S-phenethyl-3-phenoxypropylcarbamoyl)butylbenzamide (Compound 194);

tert-butyl 3-[2-naphthalen-2-yl-1S-(2-oxo-1S-phenethyl-3-phenoxypropylcarbamoyl)ethylcarbamoyl]benzylcarbamate (Compound 195);

N-(3-benzyloxy-2-oxo-1S-phenethylpropyl)-3-methyl-2-(2-phenoxyacetylaimino)pentanamide (Compound 196);

2S-acetylamino-N-(3-benzyloxy-2-oxo-1S-phenethylpropyl)-3-methylpentanamide (Compound 197);

benzyl 1S-(3-benzyloxy-2-oxo-1S-phenethylpropylsulfamoylmethyl)-2-methylbutylcarbamate (Compound 198);

benzyl 1S-(1S-benzyloxyacetylpentylsulfamoylmethyl)-2-methylbutylcarbamate (Compound 199);

2S-acetylamino-N-(3-hydroxy-2-oxo-1S-phenethylpropyl)-3-methylpentanamide (Compound 200);

methyl N-[1S-(3-benzyloxy-2-oxo-1S-phenethylpropylcarbamoyl)-2-methylbutylisophthalamate (Compound 201); ¹H NMR (CDCl₃): δ 0.9–0.97 ppm (m, 6H), 8 1.2–1.3 ppm (m, 2H), δ 1.8–2 ppm (m, 2H), δ 2.2–2.3 ppm (m, 1H), δ 2.55–2.62 ppm (t, 2H), δ 3.9 ppm (s, 3H), δ 4.13 ppm (m, 2H), δ 4.45–4.65 ppm (m, 3H), δ 4.87–4.93 ppm (m, 1H), δ 6.43–6.46 ppm (d, 1H), δ 6.78–6.82 ppm (d, 1H), δ 7.04–7.06 ppm (d, 2H), δ 7.15–7.4 ppm (m, 13H), δ 7.5–7.6 ppm (t, 1H), δ 8.00–8.03 ppm (d, 1H), δ 8.15–8.18 ppm (d, 1H), δ 8.40 ppm (m, 1H); LC/MS (559.3 M+H⁺);

benzyl 2-methyl-1S-(2-oxo-1S-phenethyl-3-phenoxypropylsulfamoylmethyl)butylcarbamate (Compound 202);

2S-acetylamino-N⁴-(3-aminomethylphenyl)-N¹-(3-benzyloxy-2-oxo-1-phenethylpropyl)succinamide (Compound 203);

methyl N-[1S-(3-hydroxy-2-oxo-1S-phenethylpropylcarbamoyl)-2-methylbutylisophthalamate (Compound 204); ¹H NMR (CDCl₃): δ 0.91–1.04 ppm (m, 6H), δ 1.5–1.7 ppm (m, 2H), δ 1.85–2.05 ppm (m, 2H), δ 2.1–2.25 ppm (m, 1H), δ 2.58–2.64 ppm (t, 2H), δ 3.92 ppm (s, 3H), δ 4.35 ppm (s, 2H), δ 4.46–4.52 ppm (t, 1H), δ 4.6–4.7 ppm (m, 1H), δ 6.65–6.68 ppm (d, 1H), δ 6.82–6.85 ppm (d, 1H), δ 7.06–7.08 ppm (d, 1H), δ 7.1–7.24 ppm (m, 8H), δ 7.48–7.54 ppm (t, 1H), δ 8.00–8.03 ppm (d, 1H), δ 8.15–8.18 ppm (d, 1H), δ 8.40 ppm (m, 1H); LC/MS (469.2 M+H⁺);

N-[1S-(3-benzyloxy-2-oxo-1S-phenethylpropylcarbamoyl)-2-methylbutyl]-3-[N',N''-di(tert-butoxycarbonyl)guanidino]benzamide (Compound 205);

N-[1S-(3-benzyloxy-2-oxo-1S-phenethylpropylcarbamoyl)-2-methylbutyl]-3-guanidinobenzamide (Compound 206);

benzyl 1S-(3-benzyloxy-2-oxo-1S-phenethylpropylsulfamoylmethyl)pentylcarbamate (Compound 207);

benzyl 1S-(1S-benzyloxyacetylpentylsulfamoylmethyl)-3-phenylpropylcarbamate (Compound 208);

tert-butyl 1S-(3-benzyloxy-2-oxo-1S-phenethylpropylsulfamoylmethyl)-3-phenylpropylcarbamate (Compound 209);

N-[1S-(3-hydroxy-2-oxo-1S-phenethylpropylcarbamoyl)-2-methylbutyl]-3-[N',N''-di(tert-butoxycarbonyl)guanidino]benzamide (Compound 210);

N-[1S-(3-hydroxy-2-oxo-1S-phenethylpropylcarbamoyl)-2-methylbutyl]-3-guanidinobenzamide (Compound 211);

tert-butyl 3-[1S-(3-benzyloxy-1S-methyl-2-oxopropylcarbamoyl)-2-methylbutylcarbamoyl]benzylcarbamate (Compound 212); ¹H NMR (CDCl₃): δ 0.92–0.97 ppm (m, 6H), δ 1.34–1.36 ppm (d. 3H), δ 1.44 ppm (s, 9H), 64.19–4.2 ppm (d, 2H), δ 4.33–4.35 ppm (d, 2H), δ 4.58–4.61 ppm (d, 2H), δ 4.8–5 ppm (m, 1H), δ 6.47–6.49 ppm (d, 1H), δ 6.75–6.8 ppm (d, 1H), δ 7.3–7.42 ppm (m, 6H), δ 7.64–7.69 ppm (m, 2H); LC/MS (540.2 M+H⁺);

tert-butyl 3-[1S-(3-hydroxy-1S-methyl-2-oxopropylcarbamoyl)-2-methylbutylcarbamoyl]benzylcarbamate (Compound 213); ¹H NMR (CDCl₃): δ 0.88–1.00 ppm (m, 6H), δ 1.23 ppm (m. 2H), δ 1.36–1.38 ppm (d, 2H), δ 1.48 ppm (s, 9H), δ 3.47 ppm (s, 1H), δ 4.33–4.35 ppm (d, 2H), δ 4.4–4.41 ppm (m, 1H), δ 4.45–4.5 ppm (t, 1H), δ 4.57–4.64 ppm (m, 1H), δ 4.9 ppm (m, 1H), δ 6.57 ppm (m, 1H), δ 6.69–6.72 ppm (d, 1H), δ 7.37–7.5 ppm (m, 2H), δ 7.64–7.69 ppm (m, 2H); LC/MS (450.1 M+H⁺);

3-aminomethyl-N-[1S-(3-benzyloxy-1S-methyl-2-oxopropylcarbamoyl)-2-methylbutyl]benzamide (Compound 214); ¹H NMR (DMSO): δ 0.82–0.91 ppm (m, 6H), δ 1.19–1.21 ppm (d.m 2H), δ 1.4–1.6 ppm (m, 1H), δ 1.8–2.0 ppm (m, 1H), δ 4.01–4.1 ppm (m, 2H), δ 4.3–4.4 ppm (m, 2H), δ 4.46–4.47 ppm (m, 2H), δ 7.26–7.37 ppm (m, 5H), δ 7.5–7.59 ppm (m, 1H), δ 7.6–7.63 ppm (m, 1H), δ 7.88–7.95 ppm (m, 1H), δ 7.99 ppm (s, 1H), δ 8.2–8.4 ppm (m, 3H), δ 8.55–8.59 ppm (t, 1H); LC/MS (440.1 M+H⁺);

3-aminomethyl-N-[1S-(3-hydroxy-1S-methyl-2-oxopropylcarbamoyl)-2-methylbutyl]benzamide (Compound 215); ¹H NMR (DMSO): δ 0.82–0.90 ppm (m, 6H), δ 1.19–1.21 ppm (d. 2H), δ 1.4–1.6 ppm (m, 1H), δ 1.95–2.0 ppm (m, 1H), δ 4.01–4.1 ppm (m, 2H), δ 4.19 ppm (s, 1H), δ 4.3–4.4 ppm (m, 1H), δ 7.5–7.55 ppm (t, 1H), δ 7.59–7.61 ppm (m, 1H), δ 7.89–7.91 ppm (m, 1H), δ 7.98 ppm (s, 1H), δ 8.1–8.4 ppm (m, 3H); LC/MS (350 M+H⁺);

benzyl 1S-(3-benzyloxy-1S-methyl-2-oxopropylcarbamoyl)-2-methylbutylcarbamate (Compound 216); ¹H NMR (CDCl₃): δ 0.90–0.92 ppm (d, 6H), δ 1.30–1.33 ppm (d. 3H), δ 4.10–4.2 ppm (m, 3H), δ 4.57–4.59 ppm (d, 2H), 64.75–4.85 ppm (m, 1H), δ 5.09–5.12 ppm (s, 3H), δ 6.54–6.57 ppm (d, 1H), δ 7.32–7.38 ppm (m, 10H); LC/MS (441 M+H⁺);

benzyl 3-methyl-1S-(2-oxo-1S-phenethyl-3-phenoxypropylsulfamoylmethyl)butylcarbamate (Compound 217);

benzyl 3-methyl-1R-(2-oxo-1S-phenethyl-3-phenoxypropylsulfamoylmethyl)butylcarbamate (Compound 218);

tert-butyl 1S-(2-oxo-1S-phenethyl-3-phenoxypropylsulfamoylmethyl)-3-phenylpropylcarbamate (Compound 219);

benzyl 2-methyl-1S-(2-oxo-1R-phenethyl-3-phenoxypropylsulfamoylmethyl)butylcarbamate (Compound 220);

benzyl 5-(2S-benzyloxycarbonylamino-3-methylpentane-1-sulfonylamino)-6-oxo-7-phenoxyheptylcarbamate (Compound 221);

benzyl 5S-(2S-benzyloxycarbonylamino-3-methylpentan-1-ylsulfonylamino)-7-(4-methoxyphenoxy)-6-oxoheptylcarbamate (Compound 222);

tert-butyl 2-methyl-1S-(2-oxo-1S-phenethyl-3-phenoxypropylsulfamoylmethyl)butylcarbamate (Compound 223);

2S-amino-3-methylpentane-N-(2-oxo-1S-phenethyl-3-phenoxypropyl)-1-sulfonamide (Compound 224);

N-[3-methyl-1-(2-oxo-1-phenethyl-3-phenoxypropylsulfamoylmethyl)butyl]nicotinamide (Compound 225);

benzyl 1S-[3-(3-methoxyphenoxy)-2-oxo-1S-phenethylpropylsulfamoylmethyl]-2-methylbutylcarbamate (Compound 226);

benzyl 1S-(3-benzo[1,3]dioxol-5-yloxy-2-oxo-1S-phenethylpropylsulfamoylmethyl]-2-methylbutylcarbamate (Compound 227);

tert-butyl 1S-(3-benzo[1,3]dioxol-5-yloxy-2-oxo-1S-phenethylpropylsulfamoylmethyl)-2-methylbutylcarbamate (Compound 228);

tert-butyl 1S-[3-(3-methoxyphenoxy)-2-oxo-1S-phenethylpropylsulfamoylmethyl]-2-methylbutylcarbamate (Compound 229);

benzyl 1S-[3-(3-dimethylaminophenoxy)-2-oxo-1S-phenethylpropylsulfamoylmethyl]-2-methylbutylcarbamate (Compound 230);

3S-(2S-benzyloxycarbonylamino-3-hydroxybutyralamino)-5-methanesulfonyl-2-oxopentyl 2,5-dichlorobenzoate (Compound 231);

benzyl 1S-[3-(4-methoxyphenoxy)-2-oxo-1S-phenethylpropylsulfamoylmethyl]-2-methylbutylcarbamate (Compound 232);

benzyl 1S-(3-benzyloxy-1S-methyl-2-oxo-propylcarbamoyl)-2-hydroxypropylcarbamate (Compound 233); ¹H NMR (CDCl₃): δ 1.14–1.17 ppm (d, 3H), δ 1.30–1.32 ppm (d, 2H), δ 4.17–4.18 ppm (d, 2H), δ 4.57–4.60 ppm (d, 2H), δ 4.76–4.82 ppm (m, 1H), δ 5.11–5.14 ppm (m, 2H), δ 5.66–5.69 ppm (d, 1H), δ 6.94–6.97 ppm (d, 1H), δ 7.28–7.4 ppm (m, 10H);

benzyl 1S-[3-(4-chlorophenoxy)-2-oxo-1S-phenethylpropylsulfamoylmethyl]-2-methylbutylcarbamate (Compound 234);

benzyl 2-methyl-1S-[2-oxo-1S-phenethyl-3-(4-sulfamoylphenoxy)propylsulfamoylmethyl]butylcarbamate (Compound 235);

benzyl 2-methyl-1S-[2-oxo-1S-phenethyl-3-(4-carbamoylphenoxy)propylsulfamoylmethyl]butylcarbamate (Compound 236);

4-dimethylamino-N-[3-methyl-1-(2-oxo-3-phenoxypropylcarbamoyl)butyl]benzamide (Compound 237);

benzyl 2-methyl-1-{3-methyl-1-[1-(2-oxo-3-phenoxypropylcarbamoyl)-2-phenylethylcarbamoyl]butylcarbamoyl}propyl)carbamate (Compound 238);

2-(3-aminomethylphenyl)oxazole-N-(3-hydroxy-2-oxo-1-phenethylpropyl)-4-carboxamide (Compound 239);

benzyl 1-[3-(4-imidazol-1-ylphenoxy)-2-oxo-1-phenethylpropylsulfamoylmethyl]-2-methylbutylcarbamate (Compound 240);

2-(3-aminomethylphenyl)-N-(3-hydroxy-2-oxo-1-phenethylpropyl)oxazole-4-carboxamide (Compound 241);

2-amino-N-(3-benzyloxy-2-oxo-1-phenethylpropyl)-4-phenylbutyramide (Compound 242);

N-(2-oxo-1-phenethyl-3-phenoxypropyl)dibenzofuran-2-sulfonamide (Compound 243); ESI-MS m/z 500.2 (M+H⁺);

tert-butyl 4-[1-(3-hydroxy-2-oxo-1-phenethylpropylsulfamoylmethyl)-3-methylbutylcarbamoyl]piperidine-1-carboxylate (Compound 244);

tert-butyl 1-(3-benzyloxy-1-methyl-2-oxopropylsulfamoylmethyl)-3-methylbutylcarbamate (Compound 245); and N-(1-benzyloxyacetylpentyl)-2,2-dimethylpropionamide (Compound 246); ¹H NMR (CDCl₃): δ 0.82–0.87 ppm (m, 3H), δ 1.21–1.20 ppm (m, 3H), δ 1.41 ppm (s, 9H), δ 1.7–1.9 ppm (m, 1H), δ 4.1 ppm (d, 2H), δ 4.5–4.7 (m, 3H), δ 5.06–5.09 (d, 1H), δ 7.3–7.4 ppm (m, 5H); LC/MS (320 M+H⁺).

Example 7

Cathepsin B Assay

Solutions of test compounds in varying concentrations were prepared in 10 μL of dimethyl sulfoxide (DMSO) and then diluted into assay buffer (40 μL, comprising: N,N-bis (2-hydroxyethyl)-2-aminoethanesulfonic acid (BES), 50 mM (pH 6); polyoxyethylenesorbitan monolaurate, 0.05%; and dithiothreitol (DTT), 2.5 mM). Human cathepsin B (0.025 pMoles in 25 μL of assay buffer) was added to the dilutions. The assay solutions were mixed for 5–10 seconds on a shaker plate, covered and incubated for 30 minutes at room temperature. Z-FR-AMC (20 nMoles in 25 μL of assay buffer) was added to the assay solutions and hydrolysis was followed spectrophotometrically at (λ 460 nm) for 5 minutes. Apparent inhibition constants ($K_i$) were calculated from the enzyme progress curves using standard mathematical models.

Compounds of the invention were tested by the above-described assay and observed to exhibit cathepsin B inhibitory activity.

Example 8

Cathepsin K Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin K (0.0906 pMoles in 25 μL of assay buffer) was added to the dilutions. The assay solutions were mixed for 5–10 seconds on a shaker plate, covered and incubated for 30 minutes at room temperature. Z-Phe-Arg-AMC (4 nMoles in 25 μL of assay buffer) was added to the assay solutions and hydrolysis was followed spectrophotometrically at ($\lambda$ 460 nm) for 5 minutes. Apparent inhibition constants ($K_i$) were calculated from the enzyme progress curves using standard mathematical models.

Compounds of the invention were tested by the above-described assay and observed to exhibit cathepsin K inhibitory activity.

Example 9

Cathepsin L Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin L (0.05 pMoles in 25 μL of assay buffer) was added to the dilutions. The assay solutions were mixed for 5–10 seconds on a shaker plate, covered and incubated for 30 minutes at room temperature. Z-Phe-Arg-AMC (1 nMoles in 25 μL of assay buffer) was added to the assay solutions and hydrolysis was followed spectrophotometrically at ($\lambda$ 460 nm) for 5 minutes. Apparent inhibition constants ($K_i$) were calculated from the enzyme progress curves using standard mathematical models.

Compounds of the invention were tested by the above-described assay and observed to exhibit cathepsin L inhibitory activity.

Example 10

Cathepsin S Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM). Human cathepsin S (0.158 pMoles in 25 μL of assay buffer) was added to the dilutions. The assay solutions were mixed for 5–10 seconds on a shaker plate, covered and incubated for 30 minutes at room temperature. Z-Val-Val-Arg-AMC (9 nMoles in 25 μL of assay buffer) was added to the assay solutions and hydrolysis was followed spectrophotometrically at ($\lambda$ 460 nm) for 5 minutes. Apparent inhibition constants ($K_i$) were calculated from the enzyme progress curves using standard mathematical models.

Compounds of the invention were tested by the above-described assay and observed to exhibit cathepsin S inhibitory activity.

Example 11

Representative Pharmaceutical Formulations Containing a Compound of Formula I

| ORAL FORMULATION | |
|---|---|
| Compound of Formula I | 10–100 mg |
| Citric Acid Monohydrate | 105 mg |
| Sodium Hydroxide | 18 mg |
| Flavoring | |
| Water | q.s. to 100 mL |
| INTRAVENOUS FORMULATION | |
| Compound of Formula I | 0.1–10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |
| TABLET FORMULATION | |
| Compound of Formula I | 1% |
| Microcrystalline Cellulose | 73% |
| Stearic Acid | 25% |
| Colloidal Silica | 1% |

The resulting tablets are useful for administration in accordance with the methods of this invention for treating or preventing a cathepsin mediated disease state, such as osteoporosis, juvenile onset diabetes, multiple sclerosis, pemphigus vulgaris, Graves' disease, myasthenia gravis, systemic lupus erythemotasus, rheumatoid arthritis, Hashimoto's thyroiditis, asthma, organ transplant or tissue graft rejections, chronic obstructive pulmonary disease, bronchiolitis, excessive airway elastolysis in asthma and bronchitis, pneumonities, plaque rupture, atheroma and systemic amyloidosis.

We claim:

1. A process for preparing a compound of Formula II:

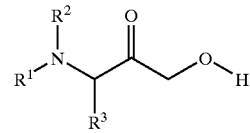

II which process comprises hydrogenating a compound of Formula 9:

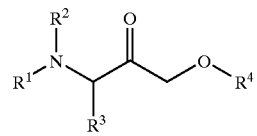

9 in which $R^1$ is peptidyl, $R^2$ is hydrogen or $(C_{1-6})$alkyl, $R^3$ is an amino acid side chain and $R^4$ is $(C_{1-6})$alkyl or $(C_{6-12})$aryl$(C_{1-6})$alkyl, in the presence of a catalytic amount of 20% palladium hydroxide on carbon.

2. The process of claim 1 in which the hydrogenation is effected with cyclohexene in a 1:2 volume:volume mixture of cyclohexene:ethanol.

3. The process of claim 2 for preparing an individual (R)- or (S)-isomer of the compound of Formula II.

4. A compound of Formula I:

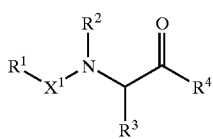

in which:
X¹ is a divalent group of Formula (a):

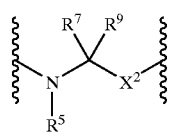

wherein:
X² is —C(O)— or —CH₂S(O)₂—;
R⁵ is hydrogen or as defined below;
R⁷ is (i) butyl, ethyl, methyl, 1-methylethyl, 1-methylpropyl, or 2-methylpropyl, optionally substituted with —OR¹⁰, —C(O)OR¹⁰, —NR¹⁰R¹⁰, —NR¹⁰C(O)OR¹⁰ or —C(O)NR¹⁰R¹⁰, wherein R¹⁰ is hydrogen or (C₁₋₆)alkyl, or (ii) benzyoxycarbonylmethyl, biphenyl-4-ylmethyl, cyclohexyl, cyclohexylmethyl, naplth-2-ylmethyl, phenylcarbamoylmethyl or phenylethyl or (iii) together with R⁵ is phenylenedimethylene; wherein within R⁷ any aromatic ring system present may be substituted further by 1 to 3 radicals independently selected from nitro and amino; and
R⁹ at each occurrence is hydrogen; and
R¹ is hydrogen, acetyl, 3-aminobenzoyl, 4-aminobutyryl, 3-aminopropionyl, 6-aminohexanoyl, 3-aminomethylbenzoyl, 4-aminomethylbenzoyl, benzoyl, benzylcarbamoyl, 4-benzyloxybenzoyl, benzyloxycarbonyl, tert-butoxycarbonyl, 3-tert-butoxycarbonylaminobenzoyl, 4-tert-butoxycarbonylaminobutyryl, 6-tert-butoxycarbonylaminohexanoyl, 3-tert-butoxycarbonylaminomethylbenzoyl, 4-tert-butoxycarbonylaminomethylbenzoyl, 1-tert-butoxycarbonylpiperidin-4-ylcarbonyl, 1-tert-butoxycarbonylpyrrolidin-2-ylcarbonyl, 3-carbamoylbenzoyl, 3-cyanobenzoyl, dibenzofur-2-ylsulfonyl, 3-[N',N''-di(tert-butoxycarbonyl)guanidino]benzoyl, 4-dimethylaminobenzoyl, 2,2-dimethylpropionyl, 3-diphenylpropionyl, 3-fluorobenzoyl, 3-guanidinobenzoyl, 3-hydroxybenzoyl, 1H-indol-3-ylacetyl, 3-methoxycarbonylbenzoyl, 3-methoxycarbonylpropionyl, 3-methoxyphenylcarbamoyl, 4-methylpiperazin-1-ylcarbonyl, morpholin-4-ylcarbonyl, naphth-1-ylcarbonyl, naphth-2-ylcarbonyl, naphth-2-ylsulfonyl, 3-nitrophenylacetyl, phenoxyacetyl, phenylcarbamoyl, 3-phenylpropionyl, piperidin-4-ylcarbonyl, 1-piperidin-1-ylpiperidin-1-ylcarbonyl, pyrid-3-ylacetyl, pyrid-4-ylacetyl, pyrid-3-ylcarbonyl, pyrid-4-ylcarbonyl, pyrrolidin-2-ylcarbonyl, pyrazinylcarbonyl or 3-ureidobenzoyl;
R² is hydrogen or as defined below,
R³ is hydrogen, 2-benzyloxyethyl, 4-benzyloxycarbonylaminobutyl, benzyloxymethyl, 2-(4-hydroxyphenyl)ethyl, 1H-indol-3-ylmethyl, 4-methoxybenzyl, methyl, 2-methylsulfonylethyl, 2-methylpropyl, phenethyl, 2-phenylcarbamoylethyl or together with R² forms tetramethylene or phenylenedimethylene; and
R⁴ is acetoxymethyl, benzo[1,3]dioxol-5-yloxy, benzyloxymethyl, 4-carbamoylphenoxymethyl, 4-chlorophenoxymethyl, 2,5-dichlorobenzoyloxymethyl, 2,6-dichlorobenzoyloxymethyl, 3-dimethylaminophenoxymethyl, ethoxymethyl, hydroxymethyl, 1-hydroxy-1-methylethyl, 4-(1H-imidazol-1-yl)phenoxymethyl, methoxymethyl, 3-methoxyphenoxymethyl, 4-methoxyphenoxymethyl, 4-sulfamoylphenoxymethyl or phenoxymethyl; and the N-oxide derivatives, prodrug derivatives, protected derivatives, individual isomers and mixtures of isomers; and the pharmaceutically acceptable salts thereof.

5. The compound of claim 4 in which R⁵ is hydrogen and R⁷ is butyl, 1-methylethyl, 1-methylpropyl, 2-methylpropyl or naphth-2-ylmethyl; R¹ is 3-aminobenzoyl, 3-aminomethylbenzoyl, 4-aminomethylbenzoyl, benzoyl, benzylcarbamoyl, benzyloxycarbonyl, tert-butoxycarbonyl, 3-tert-butoxycarbonylaminobenzoyl, 4-tert-butoxycarbonylaminomethylbenzoyl, 3-[N',N''-di(tert-butoxycarbonyl)guanidino]benzoyl, 4-dimethylaminobenzoyl, 3-guanidinobenzoyl 4-methylpiperazin-1-ylcarbonyl, naphth-1-ylcarbonyl, naphth-2-ylcarbonyl or piperidin-4-ylcarbonyl; R² is hydrogen; R³ is hydrogen, 4-benzyloxycarbonylaminobutyl or phenethyl; and R⁴ is benzyloxymethyl, hydroxymethyl, 2,5-dichlorobenzoyloxymethyl, ethoxymethyl, 1-hydroxy-1-methylethyl or phenoxymethyl; and the N-oxide derivatives, prodrug derivatives, protected derivatives, individual isomers and mixtures of isomers; and the pharmaceutically acceptable salts thereof.

6. A pharmaceutical composition comprising a therapeutically effective amount of a compound of claim 4 in combination with one or more pharmaceutically acceptable excipient(s).

7. The composition of claim 6 which further comprises one or more active ingredient(s) selected from the group consisting of (i) a therapeutically effective amount of a bisphosphonic acid or acid ester thereof or a pharmaceutically acceptable salt thereof and (ii) a therapeutically effective amount of an estrogen receptor agonist or a pharmaceutically acceptable salt thereof.

8. The composition of claim 7 wherein the bisphosphonic acid is selected from the group consisting of 1,1-dichloromethylene-1,1-diphosphonic acid, 1-hydroxy-3-pyrrolidin-1-ylpropylidene-1,1-bisphosphonic acid, 1-hydroxyethylidene-1,1-diphosphonic acid, 1-hydroxy-3-(N-methyl-N-pentylamino)propylidene-1,1-bisphosphonic acid, 6-amino-1-hydroxyhexylidene-1,1-bisphosphonic acid, 3-(dimethylamino)-1-hydroxypropylidene-1,1-bisphosphonic acid, 3-amino-1-hydroxypropylidene-1,1-bisphosphonic acid, 2-pyrid-2-ylethylidene-1,1-bisphosphonic acid, 1-hydroxy-2-pyrid-3-ylethylidene-1,1-bisphosphonic acid, 4-chlorophenylthiomethylenebisphosphonic acid and 1-hydroxy-2-(1H-imidazol-1-yl)ethylidene-1,1-bisphosphonic acid or acid ester thereof or a pharmaceutically acceptable salt thereof.

9. The composition of claim 8 wherein the bisphosphonic acid is 1,1-dichloromethylene-1,1-diphosphonic acid or a pharmaceutically acceptable salt thereof.

10. The composition of claim 9 which comprises 1,1-dichloromethylene-1,1-diphosphonate monosodium trihydrate.

11. A method of treating a disease in an animal in which cysteine protease activity contributes to the pathology and/or symptomatology of the disease, which method comprises administering to the animal a therapeutically effective amount of compound of claim 4; or a N-oxide derivative, prodrug derivative, protected derivative, individual isomer and mixtures of isomers; or pharmaceutically acceptable salt thereof.

12. The method of claim 11 wherein the disease is osteoporosis.

13. The method of claim 12 wherein the animal is a human.

14. The method of claim 13 wherein the human is a post-menopausal woman.

15. The method of claim 14 wherein the cysteine protease is cathepsin K.

16. The method of claim 11 in which the cysteine protease is cathepsin S.

17. The method of claim 16 in which the disease is an autoimmune disorder, allergic disorder, allogeneic immune response, a disorder involving excessive elastolysis, cardiovascular disorders or a disorder involving fibril formation.

18. The method of claim 17 in which the disorder is selected from juvenile onset diabetes, multiple sclerosis, pemphigus vulgaris, Graves' disease, myasthenia gravis, systemic lupus erythemotasus, rheumatoid arthritis, Hashimoto's thyroiditis, asthma, organ transplant or tissue graft rejections, chronic obstructive pulmonary disease, bronchiolitis, excessive airway elastolysis in asthma and bronchitis, pneumonities, plaque rupture, atheroma and systemic amyloidosis.

* * * * *